US008617867B2

(12) United States Patent
Roiz et al.

(10) Patent No.: US 8,617,867 B2
(45) Date of Patent: *Dec. 31, 2013

(54) METHODS OF AND COMPOSITIONS FOR INHIBITING THE PROLIFERATION OF MAMMALIAN CELLS

(75) Inventors: Levava Roiz, Kiryat-Ono (IL); Betty Schwartz, Rechovot (IL); Patricia Smirnoff, Rehovot (IL); Oded Shoseyov, Karmei Yosef (IL)

(73) Assignee: Yissum Research Develpment Company of the Hebrew University of Jerusalem, Jerusalem (IL)

( * ) Notice: Subject to any disclaimer, the term of this patent is extended or adjusted under 35 U.S.C. 154(b) by 16 days.

This patent is subject to a terminal disclaimer.

(21) Appl. No.: 13/342,067

(22) Filed: Jan. 1, 2012

(65) Prior Publication Data
US 2012/0100128 A1    Apr. 26, 2012

Related U.S. Application Data

(63) Continuation of application No. 12/890,762, filed on Sep. 27, 2010, now Pat. No. 8,236,543, which is a continuation of application No. 10/952,495, filed on Sep. 29, 2004, now Pat. No. 7,811,981, which is a continuation-in-part of application No. 10/069,454, filed as application No. PCT/IL00/00514 on Aug. 29, 2000, now Pat. No. 7,101,839, which is a continuation-in-part of application No. 09/385,411, filed on Aug. 30, 1999, now abandoned.

(51) Int. Cl.
C12N 9/22    (2006.01)

(52) U.S. Cl.
USPC ........................................................ 435/199

(58) Field of Classification Search
USPC ........................................................ 435/199
See application file for complete search history.

(56) References Cited

U.S. PATENT DOCUMENTS

| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,879,219 A | 11/1989 | Wands et al. |
| 5,011,771 A | 4/1991 | Bellet et al. |
| 5,281,521 A | 1/1994 | Trojanowski et al. |
| 5,786,457 A | 7/1998 | Nett et al. |
| 6,590,075 B2 | 7/2003 | Ruben et al. |
| 7,101,839 B1 * | 9/2006 | Roiz et al. ................ 514/19.3 |
| 7,811,981 B2 * | 10/2010 | Roiz et al. ................ 424/94.61 |
| 8,236,543 B2 * | 8/2012 | Roiz et al. ................ 435/199 |
| 2005/0113327 A1 | 5/2005 | Roiz et al. |
| 2008/0013419 A1 | 1/2008 | Lee et al. |
| 2011/0008314 A1 | 1/2011 | Roiz et al. |

FOREIGN PATENT DOCUMENTS

| AU | 769011 | 3/2001 |
| EP | 1207755 | 5/2002 |
| JP | 2003-508411 | 3/2003 |
| JP | 4808346 | 11/2011 |
| WO | WO 99/33981 | 7/1999 |
| WO | WO 01/15531 | 3/2001 |
| WO | WO 2006/035439 | 4/2006 |

OTHER PUBLICATIONS

Requisition by the Examiner Dated Mar. 1, 2012 From the Canadian Intellectual Property Office Re.: Application No. 2,382,303.
Communication Under Rule 71(3) EPC Dated Apr. 27, 2012 From the European Patent Office Re.: Application No. 08168000.1.
Communication Under Rules 71(3) EPC Dated Mar. 4, 2012 From the European Patent Office Re. Application No. 10183935.5.
Communication Pursuant to Article 94(3) EPC Dated Aug. 21, 2012 From the European Patent Office Re.: Application No. 05789520.3.
Response Dated Sep. 14, 2011 to Examination Report of Jul. 5, 2011 From the Instituto Mexicano de la Propriedad Industrial Re. Application No. MX/a/2007/003766.
Translation of Notice of Reason for Rejection Dated Dec. 20, 2011 From the Japanese Patent Office Re. Application No. 2007-534175.
Official Action Dated Jan. 5, 2009 From the US Patent and Trademark Office Re.: U.S. Appl. No. 10/952,495.
Official Action Dated Mar. 13, 2007 From the US Patent and Trademark Office Re.: U.S. Appl. No. 10/952,495.
Official Action Dated Nov. 20, 2007 From the US Patent and Trademark Office Re.: U.S. Appl. No. 10/952,495.
Appellant's Brief on Appeal Under 37 CFR § 41.37 Dated Mar. 22, 2010 in the US Patent and Trademark Office Re.: U.S. Appl. No. 10/952,495.
Communication Pursuant to Article 94(3) EPC Dated Feb. 2, 2011 From the European Patent Office Re.: Application No. 08168000.1.
Communication Pursuant to Article 94(3) EPC Dated Feb. 12, 2010 From the European Patent Office Re.: Application No. 05789520.3.
Communication Pursuant to Article 96(2) EPC Dated Jul. 27, 2006 From the European Patent Office, Re.: Application No. 00954879.3.
Communication Pursuant to Rules 70(2) and 70a(2) and Reference to Rule 39(1) EPC Dated Mar. 21, 2011 From the European Patent Office Re. Application No. 10183935.5.
European Search Report and the European Search Opinion Dated Feb. 9, 2011 From the European Patent Office Re. Application No. 10183935.5.
European Search Report and the European Search Opinion Dated Feb. 12, 2010 From the European Patent Office Re.: Application No. 08168000.1.

(Continued)

Primary Examiner — Karen Cochrane Carlson

(57) ABSTRACT

A method of preventing, inhibiting and/or reversing cell motility, actin filament assembly or disassembly, proliferation, colonization, differentiation, accumulation and/or development of abnormal cells in a subject is disclosed. The method is effected by administering to the subject a therapeutically effective amount of a ribonuclease of the T2 family having actin binding activity.

13 Claims, 46 Drawing Sheets
(14 of 46 Drawing Sheet(s) Filed in Color)

(56) References Cited

OTHER PUBLICATIONS

Examination Report Dated Feb. 5, 2008 From the Instituto Mexicano de la Propriedad Industrial Re.: Application No. PA/2007/330.
Examination Report Dated Jul. 5, 2011 From the Instituto Mexicano de la Propriedad Industrial Re. Application No. MX/a/2007/003766 and Its Summary in English.
Examination Report Dated Jan. 17, 2011 From the Instituto Mexicano de la Propriedad Industrial Re. Application No. MX/a/2007/003766.
Examination Report Dated Nov. 20, 2006 From the Government of India, Patent Office Re.: Application No. IN/PCT/2002/441/CHE.
Examiner's Report dated Sep. 16, 2009 From the Australian Government, IP Australia Re.: Application No. 2005288527.
Examiner's Report Dated Oct. 25, 2010 From the Australian Government, IP Australia Re. Application No. 2005288527.
International Preliminary Report on Patentability Dated Sep. 25, 2007 From the International Preliminary Examining Authority Re.: Application No. PCT/IL05/010141.
International Search Report Date May 1, 2007 From the International Searching Authority Re.: Application No. PCT/IL05/01041.
International Search Report Dated Jan. 9, 2001 From the International Searching Authority Re.: Application No. PCT/IL00/00514.
Invitation to Pay Additional Fees Dated Oct. 27, 2006 From the International Searching Authority Re.: Application No. PCT/IL05/01041.
Notice of Acceptance Dated Jan. 19, 2011 From the Australian Government, IP Australia Re. Application No. 2005288527.
Notice of Allowance Dated Jun. 10, 2010 From the US Patent and Trademark Office Re. U.S. Appl. No. 10/952,495.
Notice of Allowance Dated Apr. 13, 2011 From the Israel Patent Office Re.: Application No. 193006.
Notice of Allowance Dated May 17, 2011 From the US Patent and Trademark Office Re.: U.S. Appl. No. 11/664,132.
Notice of Allowance Dated Oct. 19, 2011 From the US Patent and Trademark Office Re. U.S. Appl. No. 12/890,762.
Notice of Appeal in Response Dated Jan. 26, 2010 to Official Action of Aug. 5, 2009 From the US Patent and Trademark Office Re.: U.S. Appl. No. 10/952,495.
Office Action Dated Aug. 5, 2009 From the Israeli Patent Office Re.: Application No. 182323 and Its Translation Into English.
Office Action Dated Dec. 7, 2009 From the Israel Patent Office Re.: Applicaiton No. 199252 and Its Translation Into English.
Office Action Dated Oct. 13, 2010 From the Israel Patent Office Re.: Application No. 193006 and Its Translation Into English.
Office Action Dated Feb. 16, 2010 From the Israel Patent Office Re.: Application No. 182323 and Its Translation Into English.
Office Action Dated Feb. 16, 2010 From the Israel Patent Office Re.: Application No. 199252 and Its Translation Into English.
Office Action Dated Sep. 18, 2007 From the Israeli Patent Office Re.: Application No. 148345.
Office Action Dated Mar. 25, 2010 From the Israel Patent Office Re.: Applicaiton No. 193006 and Its Translation Into English.
Official Action Dated Jan. 3, 2011 From the US Patent and Trademark Office Re.: U.S. Appl. No. 11/664,132.
Official Action Dated Mar. 3, 2010 From the US Patent and Trademark Office Re.: U.S. Appl. No. 11/664,132.
Official Action Dated Aug. 5, 2009 From the US Patent and Trademark Office Re.: U.S. Appl. No. 10/952,495.
Official Action Dated Nov. 5, 2003 From the US Patent and Trademark Office Re.: U.S. Appl. No. 10/069,454.
Official Action Dated Jan. 8, 2007 From the US Patent and Trademark Office Re.: U.S. Appl. No. 10/952,495.
Official Action Dated Jan. 12, 2005 From the US Patent and Trademark Office Re.: U.S. Appl. No. 10/069,454.
Official Action Dated Sep. 12, 2003 From the US Patent and Trademark Office Re.: U.S. Appl. No. 10/069,454.
Official Action Dated Jun. 13, 2011 From the US Patent and Trademark Office Re. U.S. Appl. No. 12/890,762.
Official Action Dated Jun. 18, 2004 From the US Patent and Trademark Office Re.: U.S. Appl. No. 10/069,454.
Official Action Dated Jun. 22, 2010 From the US Patent and Trademark Office Re.: U.S. Appl. No. 11/664,132.
Official Communication Dated Apr. 3, 2009 From the Instituto Mexican, de la Propriedad Industrial Re.: Application No. PA/a/2002/002162.
Requisition by the Examiner Dated Sep. 7, 2010 From the Canadian Intellectual Property Office Re.: Application No. 2,382,303.
Requisition by the Examiner Dated Dec. 22, 2008 From the Canadian Intellectual Property Office Re.: Application No. 2,382,303.
Response Dated Mar. 1, 2011 to Requisition by the Examiner of Sep. 7, 2010 From the Canadian Intellectual Property Office Re.: Application No. 2,382,303.
Response Dated Feb. 3, 2011 to Office Action of Oct. 13, 2010 From the Israel Patent Office Re.: Application No. 193006.
Response Dated May 3, 2011 to Official Action of Jan. 3, 2011 From the US Patent and Trademark Office Re.: U.S. Appl. No. 11/664,132.
Response Dated Jul. 7, 2010 to European Search Report and the European Search Opinion Dated Feb. 12, 2010 From the European Patent Office Re.: Application No. 08168000.1.
Response Dated Jun. 9, 2010 to Communication Pursuant to Article 94(3) EPC of Feb. 12, 2010 From the European Patent Office Re.: Application No. 05789520.3.
Response Dated Sep. 13, 2011 to Official Action of Jun. 13, 2011 From the US Patent and Trademark Office Re. U.S. Appl. No. 12/890,762.
Response Dated Dec. 14, 2010 to Notice of Reason for Rejection of Oct. 5, 2010 From the Japanese Patent Office Re. Application No. 2001-519760.
Response Dated Sep. 14, 2011 to Communication Pursuant to Rules 70(2) and 70a(2) and Reference to Rule 39(1) EPC of Mar. 21, 2011 From the European Patent Office Re. Application No. 10183935.5.
Response Dated Jun. 16, 2010 to Office Action of Feb. 16, 2010 From the Israel Patent Office Re.: Application No. 182323.
Response Dated Nov. 16, 2010 to Examiner's Report of Sep. 16, 2009 From the Australian Government, IP Australia Re.: Application No. 2005288527.
Response Dated Mar. 17, 2011 to Examination Report of Jan. 17, 2011 From the Instituto Mexicano de la Propriedad Industrial Re. Application No. MX/a/2007/003766.
Response Dated Apr. 19, 2004 to Official Action of Nov. 5, 2003 From the US Patent and Trademark Office Re.: U.S. Appl. No. 10/069,454.
Response Dated Oct. 21, 2010 to Official Action of Jun. 22, 2010 From the US Patent and Trademark Office Re.: U.S. Appl. No. 11/664,132.
Response Dated Dec. 22, 2011 to Summons to Attend Oral Proceedings Pursuant to Rule 115(1) EPC of Aug. 22, 2011 From the European Patent Office Re.: Application No. 08168000.1.
Response Dated Jun. 23, 2011 to Notice of Reason for Rejection of Mar. 8, 2011 From the Japanese Patent Office Re. Application No. 2001-519760.
Response Dated Jul. 24, 2011 to Notice of Reason for Rejection of May 27, 2011 From the Japanese Patent Office Re. Application No. 2007-534175.
Response Dated Jul. 25, 2010 to Office Action Dated Mar. 25, 2010 From the Israel Patent Office Re.: Application No. 193006.
Response Dated Aug. 26, 2010 to Examiner's Report of Sep. 16, 2009 From the Australian Government, IP Australia Re.: Application No. 2005288527.
Response Dated Jan. 26, 2010 to Official Action of Aug. 5, 2009 From the US Patent and Trademark Office Re.: U.S. Appl. No. 10/952,495.
Response Dated May 29, 2011 to Communication Pursuant to Article 94(3) EPC of Feb. 2, 2011 From the European Patent Office Re.: Application No. 08168000.1.
Response Dated Mar. 31, 2010 to Official Action of Mar. 3, 2010 From the US Patent and Trademark Office Re.: U.S. Appl. No. 11/664,132.
Summons to Attend Oral Proceedings Pursuant to Rule 115(1) EPC Dated Aug. 22, 2011 From the European Patent Office Re.: Application No. 08168000.1.
Supplementary European Search Report and the European Search Opinion Dated Nov. 17, 2009 From the European Patent Office Re.: Application No. 05789520.3.

(56) References Cited

OTHER PUBLICATIONS

Supplementary Partial European Search Report Dated Sep. 15, 2004 From the European Patent Office Re.: EP 00954879.
Translation of Notice of Reason for Rejection Dated Oct. 5, 2010 From the Japanese Patent Office Re. Application No. 2001-519760.
Translation of Notice of Reason for Rejection Dated Mar. 8, 2011 From the Japanese Patent Office Re. Application No. 2001-519760.
Translation of Notice of Reason for Rejection Dated May 27, 2011 From the Japanese Patent Office Re. Application No. 2007-534175.
Translation of the Official Communication Dated Dec. 12, 2006 From the Instituto Mexicano de la Propriedad Industrial Re.: Application No. PA/a/2002/002162.
Written Opinion Dated May 1, 2007 From the International Searching Authority Re.: Application No. PCT/Il05/01041.
Acquati et al. "Cloning and Characterization of a Senescence Inducing and Class II Tumor Suppressor Gene in Ovarian Carcinoma at Chromosome Region 6q27", Oncogene, XP002552567, 20(8): 980-988, Feb. 22, 2001.
Acquati et al. "Tumor and Metastasis Suppression by the Human RNASET2 Gene", International Journal of Oncology, XP009068627, 26(5): 1159-1168, May 2005.
Bradford "A Rapid and Sensitive Method for the Quantitation of Microgram Quantities of Protein Utilizing the Principle of Protein-Dye Binding", Analytical Biochemistry, 72: 248-254, 1976.
Branden et al. "Prediciton, Engineering, and Design of Protein Structures", Introduction to Protein Structure, Chap.16: 247, 1991.
Broothaerts et al. "Petunia Hybrida S-Proteins: Ribonuclease Activity and the Role of Their Glycan Side Chains in Self-Incompatibility", Sexual Plant Reproduction, 4: 258-266, 1991.
Brown et al. "Barley Aleurone Layers Secrete a Nuclease in Response to Gibberellic Acid", Plant Physiology, 82: 801-806, 1986.
Castro et al. "Gene Therapy for Parkinson's Disease: Recent Achievements and Remaining Challenges", Histology and Histopathology, 16: 1225-1238, 2001.
Deshpande et al. "Ribonucleases From T2 Family", Critical Reviews in Microbiology, XP008009078, 28(2): 79-122, Jun. 1, 2002.
Eck et al. "Gene-Based Therapy", Goodman & Gilman's The Pharmacological Basis of Therapeutics, 9(Chap.5): 77-101, 1996.
Fett et al. "Isolation and Characterization of Angiogenin, An Angiogenic Protein From Human Carcinoma Cells", Biochemistry, XP002618087, 24(20): 5480-5486, Sep. 24, 1985.
Garrett et al. "Discovering Novel Chemotherapeutic Drugs for the Third Millenium", European Journal of Cancer, 35(14): 2010-2030, 1999.
Guo et al., "Protein Tolerance to Random Amino Acid Change", Proc. Natl. Acad. Sci. USA, PNAS, 101(25): 9205-9210, Jun. 22, 2004.
Gura "Systems for Identifying New Drugs Are Often Faulty", Science, 278: 1041-1042, Nov. 7, 1997.
Hamman et al. "Oral Delivery of Peptide Drugs. Barrier and Developments", Biodrugs, 19(3): 165-177, 2005.
Han et al. "Inhibitory Effects of Bevacizumab on Angiogenesis and Corneal Neovascularization", Graefe's Archive for Clinical and Experimental Ophthalmology, 247(4): 541-548, Oct. 25, 2009.
Heslop-Harrison et al. "Dynamic Aspects of Apical Zonation in the Angiosperm Pollen Tube", Sexual Plant Reproduction, 3: 187-194, 1990.
Horitsu et al. Agr. Biol. Chem., 38: 933-940, 1974.
Hu et al. "Actin Is a Binding Protein for Angiogenin", Proc. Natl. Acad. Sci. USA, 90: 1217-1221, Feb. 1993.
Hu et al. "An Angiogenin-Binding Protein From Endothelial Cells", Proc. Natl. Acad. Sci. USA, 88: 2227-2231, 1991.
Hu et al. "Technology to Obtain Sustained Release Characteristics of Drugs After Delivered to the Colon", Journal of Drug Targeting, 6(6): 439-448, 1999. Abstract.
Ide et al. "The Complete Amino Acid Sequence of Ribonuclease From Seeds of Bitter Gourd (*Momortia charantia*)", FEBS Letters, 284(2): 161-164, 1991.
Irie et al. "Role of Histidine 46 in the Hydrolysis and the Reverse Transphosphorylation Reaction of RNase Rh From *Rhizopus niveus*", Journal of Biochemistry, 121: 849-853, 1997.
Irie et al. "Site of Alkylation of the Major Ribonuclease From *Aspergillus saitoi* With Lodoacetate", Journal of Biochemistry, 99(3): 627-633, 1986.
Irie et al. "Structure-Function Relationships of Acid Ribonucleases: Lysosomal, Vacuolar and Periplasmic Enzymes", Pharmacological Therapy, XP002935746, 81(2): 77-89, Jan. 1, 1999. p. 79, Claims 15, 20.
Ishibashi et al. "Evaluation of Colonic Absorbability of Drugs in Dogs Using a Novel Colon—Targeted Delivery Capsule (CTDC)", Journal of Control Release, 59(3): 361-376, 1999. Abstract.
Kao et al. "A Small-Molecule Inhibitor of the Ribonucleolytic Activity of Human Angiogenin That Possesses Antitumor Activity", Proc. Natl. Acad. Sci. USA, PNAS, 99(15): 10066-10071, Jul. 23, 2002.
Kawata et al. "Amino-Acid Sequence of Ribonuclease T2 From *Aspergillus Oryzae*", European Journal of Biochemistry, XP002935748, 176: 683-697, 1988. p. 688, Claims 15, 20.
Kawata et al. "Identification of Two Essential Histidine Residues of Ribonuclease T-2 From *Aspergillus oryzae*", European Journal of Biochemistry, XP008009203, 187(1): 255-262, 1990.
Kaye et al. "A Single Amino Acid Substitution Results in a Retinoblastoma Protein Defective in Phosphorylation and Oncoprotein Binding", Proc. Natl. Acad. Sci. USA, 87: 6922-6926, 1990.
Laccetti et al. "Seminal Ribonuclease Inhibits Tumor Growth and Reduces the Metastatic Potential of Lewis Lung Carcinoma", Cancer Research, XP0020000755, 54: 4523-4526, Aug. 15, 1994.
Leland et al. "Cancer Chemotherapy—Ribonucleases to the Rescue", Chemistry & Biology, XP002565612, 8(5): 405-413, May 2001.
Lin et al. "Characterization of the Mechanism of Cellular and Cell Free Protein Synthesis Inhibition by an Anti-Tumor Ribonuclease", Biochemical and Biophysical Research Communications, 204(1): 156-162, 1994.
Liu et al. "Physical and Transcript Map of the Region Between D6S264 and D6S149 on Chromosome 6q27, the Minimal Region of Allele Loss in Sporadic Epithelial Ovarian Cancer", Oncogene, 21(3): 387-399, 2002. Abstract. GenBank Database Accession No. CAD12030.
Luhtala et al. "T2 Family Ribonucleases: Ancient Enzymes With Diverse Roles", Trends in Biochemical Sciences, XP002618088, 35(5): 253-259, May 2010.
Mastronicola et al. "Key Extracellular and Intracellular Steps in the Antitumor Action of Seminal Ribonuclease", European Journal of Biochemistry, XP002565611, 230(1): 242-249, May 15, 1995.
Matsuda et al. "Effect of Food Intake on the Delivery of Fluorescein as a Model Drug in Colon Delivery Capsule After Oral Administration to Beagle Dogs", Journal of Drug Targeting, 4(2): 59-67, 1996. Abstract.
Mesothelioma "FDA Recommends Additional Clinical Trial for Onconase", Mesothelioma, Retrieved From the Internet, 1 P., Feb. 4, 2009.
NCBI "Ribonuclease T2 Precursor [*Homo sapiens*]", NCBI Protein, Version: NP_003721.2 GI:5231228, Accession No. NP_003721, Dec. 31, 2010.
Newton et al. "RNA Damage and Inhibition of Neoplastic Endothelial Cell Growth: Effects of Human and Amphibian Ribonucleases", Radiation Research, 155(1): 171-174, 2001. Abstract.
Nomachi et al. "Purification and Some Properties of 2 Acid Ribonucleases From the Mycelia of *Aspergillus niger*", Journal of General and Applied Microbiology, XP008009205, 26(6): 375-386, 1980.
Ohgi et al. "Expression of RNase Rh From *Rhizopus niveus* in Yeast and Characterization of the Secreted Proteins", Journal of Biochemistry, 109: 776-785, 1991. p. 777, Claims 21, 26.
Orkin et al. "Report and Recommendations of the Panel to Assess the NIH Investment in Research on Gene Therapy", p. 1-41, 1995.
Roiz et al. "ACTIBIND, An Actin-Binding Fungal T2-RNase With Antiangiogenic and Anticarcinogenic Characteristics", Cancer, XP002618089, 106(10): 2295-2308, May 15, 2006.

(56) References Cited

OTHER PUBLICATIONS

Roiz et al. "Characterization of *Aspergillus niger* B-1 RNase and Its Inhibitory Effect on Pollen Germination and Pollen Tube Growth in Selected Tree Fruit", Journal of the American Society for Horticultural Science, XP002935745, 125(1): 9-14, Jan. 1, 2000. Abstract.
Roiz et al. "Stigmatic RNase in Calamondin (*Citrus reticulata* Var. *Austera x Fortunella* Sp.)", Physiologia Plantarum, 94: 585-590, 1995.
Roiz et al. "Stigmatic RNase in Self-Compatible Peach (*Prunus persica*)", International Journal of Plant Sciences, 156:(1): 37-41, 1995.
Rudinger "Characteristics of the Amino Acids as Components of a Peptide Hormone Sequence", University Park Press, Baltimore, p. 1-7, 1976.
Schwartz et al. "ACTIBIND: A Novel Anti-Carcinogenic and Anti-Angiogenic Drug", Clinical and Experimental Metastasis, XP009124827, 19(Suppl.): 66, 2002. & IXth International Congress of the Metastasis Research Society, Chicago, Ill., USA, Sep. 20-22, 2002. Abstract.
Seffernick et al. "Melamine Deaminase and Atrazine Chlorohydrolase: 98 Percent Identical But Functionally Different", Journal of Bacteriology, 183(8): 2405-2410, Apr. 2001.
Simm et al. "On the Interaction of Bovine Seminal Rnase With Actin In Vitro", European Journal of Biochemistry, 166: 49-54, 1987.
Skolnick et al. "From Genes to Protein Structure and Function: Novel Applications of Computational Approaches in the Genomic Era", Trends in Biotechnology (TIBTECH), 18: 34-39, 2000.
Smirnoff et al. "A Recombinant Human RNASET2 Glycoprotein With Antitumorigenic and Antiangiogenic Characteristics", Cancer, 107(12): 2760-2769, 2006.
Takaya et al. "Development of a Colon Delivery Capsule and the Pharmacological Activity of Recombinant Human Granulocyte Colony-Stimulating Factor (RhG-CSF) in Beagle Dogs", Journal of Pharmacy and Pharmacology, 47(6): 474-478, 1995. Abstract.
Tozaki et al. "Chitosan Capsules for Colon-Specific Drug Delivery: Improvement of Insulin Absorption From the Rat Colon", Journal of Pharmaceutical Sciences, 86(9): 1016-1021, 1997. Abstract.
Tozaki et al. "Colon-Specific Delivery of R68070, A New Thromboxane Synthase Inhibitor, Using Chitosan Capsules: Therapeutic Effects Against 2,4,6-Trinitrobenzene Sulfonic Acid-Induced Ulcerative Colitis in Rats", Life Science, 64(13): 1155-1162, 1999. Abstract.
Trubia et al. "RecName: Full=Ribonuclease T2; AltName: Full=Ribonuclease 6; Flags: Precursor", Swiss UniProtKB: Locus RNT2_Human, Accession No. O00584, Jun. 15, 2004. "MammalianRh/T2/S-Glycoprotein Ribonuclease Family Genes: Cloning of a Human Member Located in a region of Chromosome 6 (6q27) Frequently Deleted in Human Malignancies", Genomics, 42(2): 342-344, 1997.
Trubia et al. "Ribonuclease 6 Precursors [*Homo sapiens*]", GenBank Database Accession No. AAC51363. "Mammalian Rh/T2/S-Glucoprotein Ribonuclease Family Genes: Cloning of a Human Member Located in a Region of Chromosome 6 (6q27) Frequently Deleted in Human Malignancies", Genomics, XP004459303, 42(2): 342-344, Jun. 1, 1997. Abstract.
Trubia et al. "Ribonuclease T2 Precursor [*Homo sapiens* ]", NCBI Reference Sequence, GenBank Accession No. NP_003721, Jun. 28, 1999. "Mammalian Rh/T2/S-Glucoprotein Ribonuclease Family Genes: Cloning of a Human Member Located in a Region of Chromosome 6 (6q27) Frequently Deleted in Human Malignancies", Genomics, XP004459303, 42(2): 342-344, Jun. 1, 1997. Abstract.
UniProt "RNASET2 or RNASE6PL From *Homo sapiens*", Database UniProtKB Sequence [Online], XP002552568, Database Accession No. O00584, Release: 2.5/44.5, Sep. 13, 2004. Sequence.
Wikipedia "Cancer", Wikipedia, the Free Encyclopedia, 21 P., Jun. 2010.
Witkowski et al. "Conversion of A β-Ketoacyl Synthase to a Malonyl Decarboxylase by Replacement of the Active-Site Cysteine With Glutamine", Biochemistry, 38: 11643-11650, 1999.
Ye et al. "Isolation and Characterization of cDNAs Encoding Zylogenesis-Associated and Wounding-Induced Ribonucleases in *Zinnia elegans*", Plant Molecular Biology, 30: 697-709, 1996.
Yokota et al. "Isolation and Characterization of Plant Myosin From Pollen Tubes of Lily", Protoplasma, 177: 153-162, 1994.
Zhu et al. "*Escherichia coli* RNA Gene Encoding RNase I: Cloning, Overexpression, Subcellular Distribution of the Enzyme, and Use of an RNA Deletion to Identify Additional RNases", Journal of Bacteriology, 172(6): 3146-3151, 1990.
Requisition by the Examiner Dated Apr. 30, 2012 From the Canadian Intellectual Property Office Re. Application No. 2,582,041.
Translation of Notice of Reason for Rejection Dated Mar. 22, 2013 From the Japanese Patent Office Re. Application No. 2011-149849.
Requisition by the Examiner Dated Dec. 14, 2012 From the Canadian Intellectual Property Office Re. Application No. 2,582,041.
Communication Pursuant to Article 94(3) EPC Dated Jul. 2, 2013 From the European Patent Office Re.: Application No. 05789520.3.

* cited by examiner

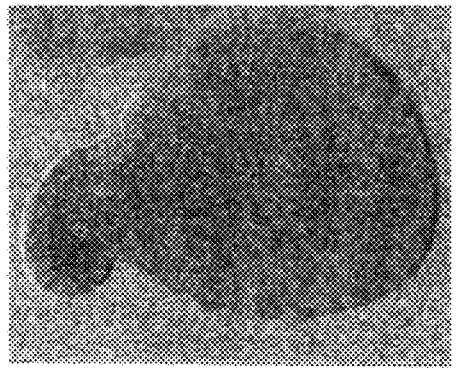
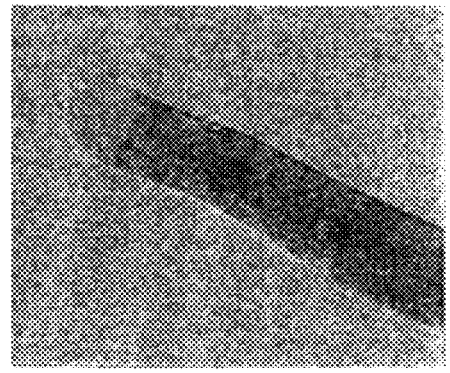
Fig. 8a　　　　　　　　Fig. 8b
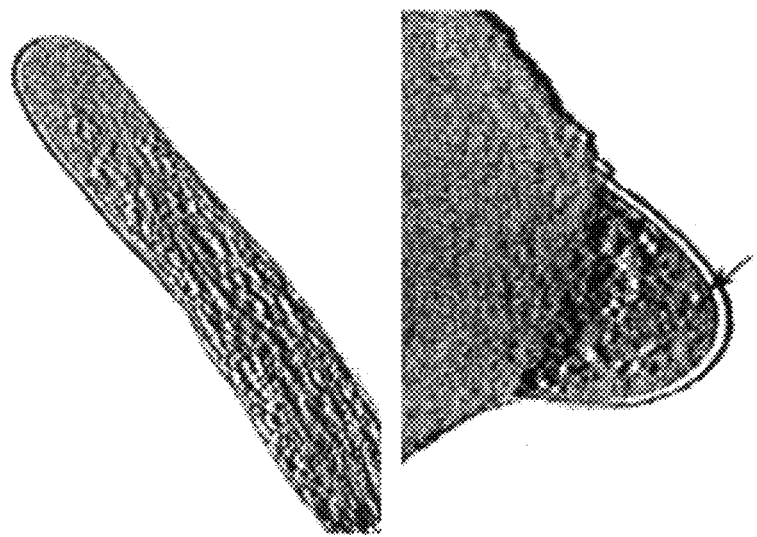
Fig. 9a　　　　　　　　Fig. 9b

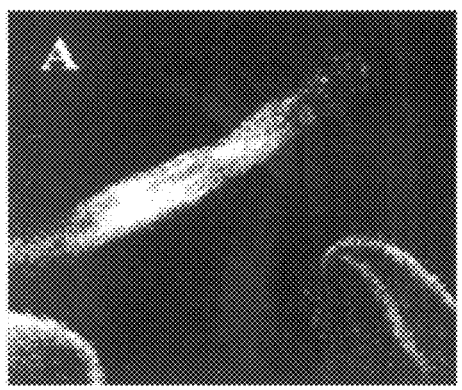 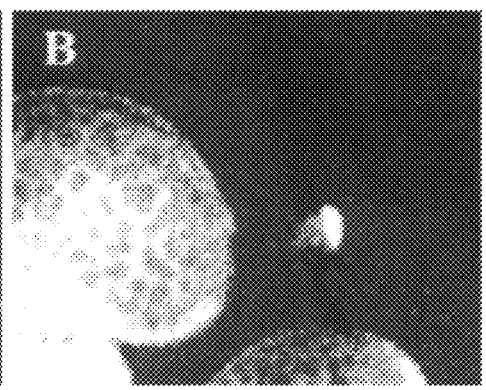
Fig. 10a                    Fig. 10b
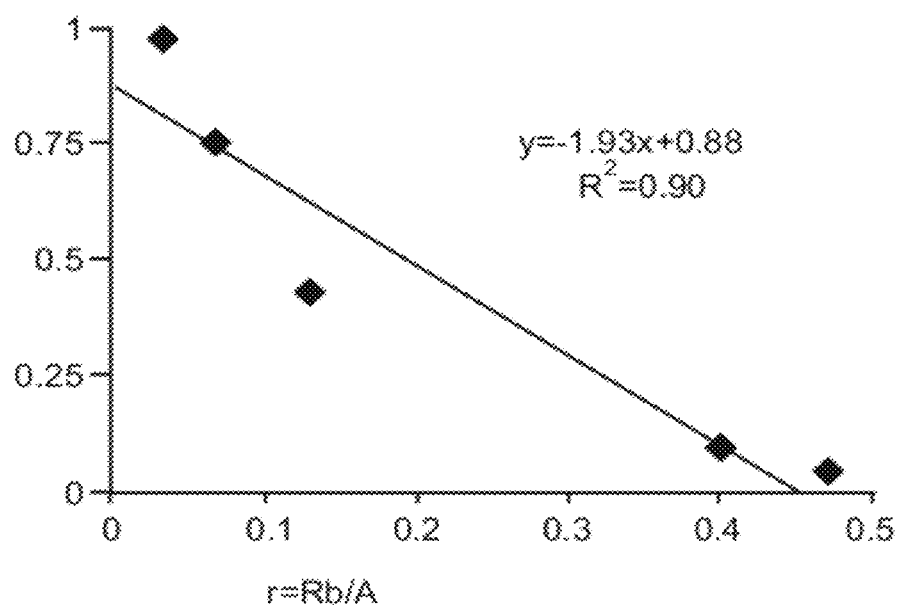
Fig. 11

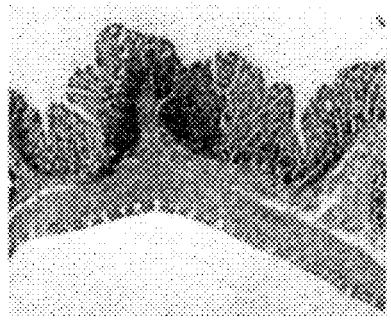
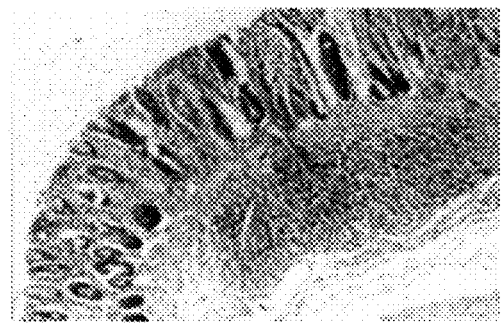
Fig. 25a　　　　　Fig. 25b
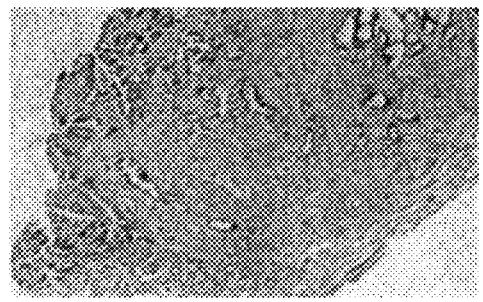
Fig. 25c
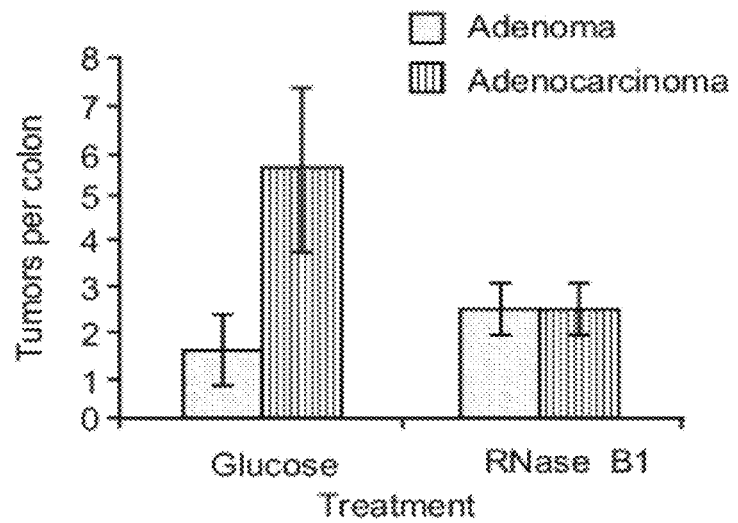
Fig. 25d

 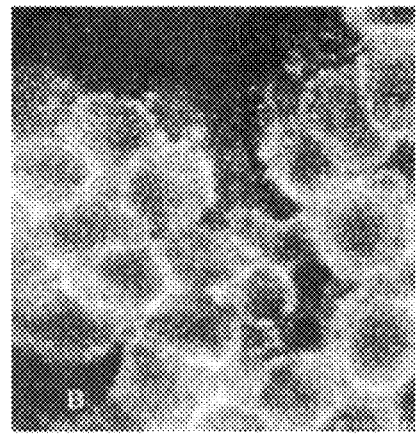
Fig. 28a  Fig. 28b
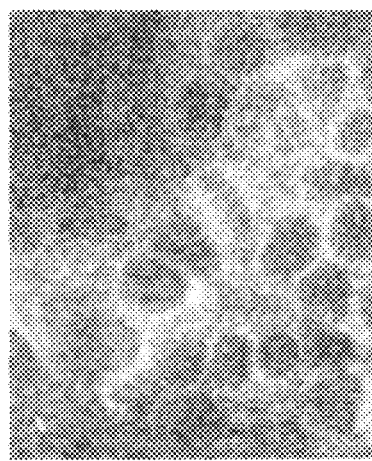 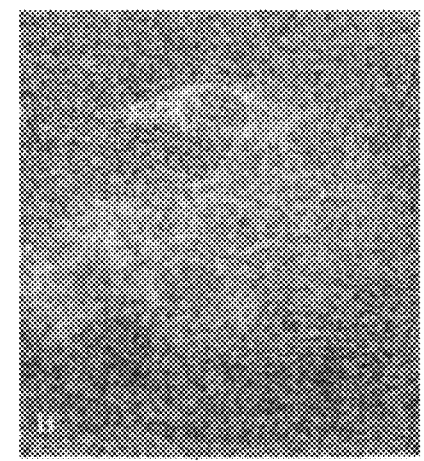
Fig. 29a  Fig. 29b

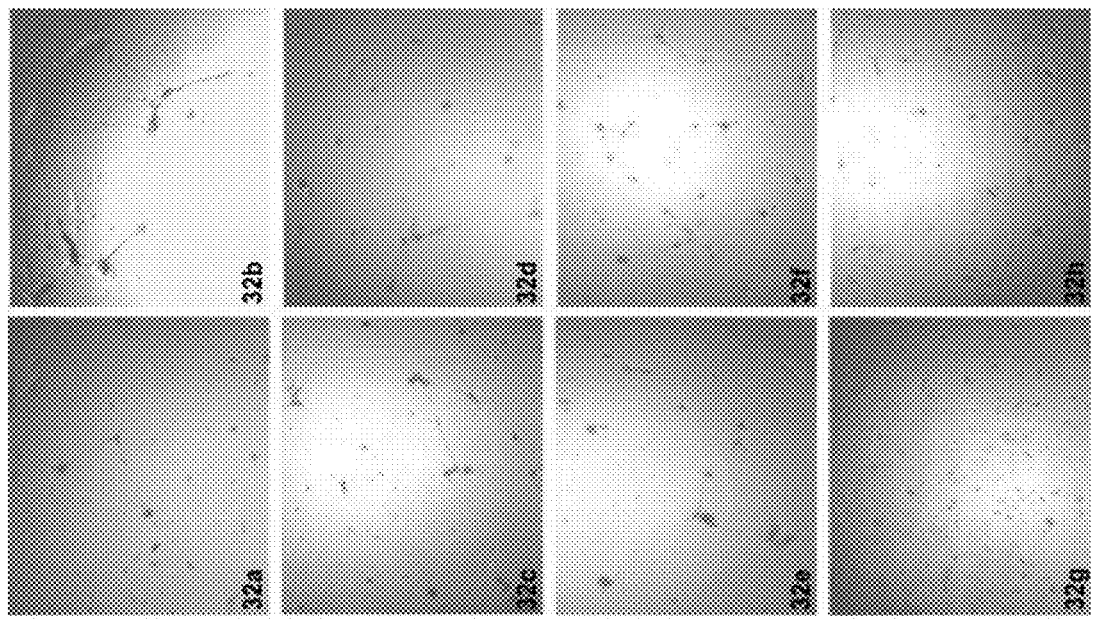

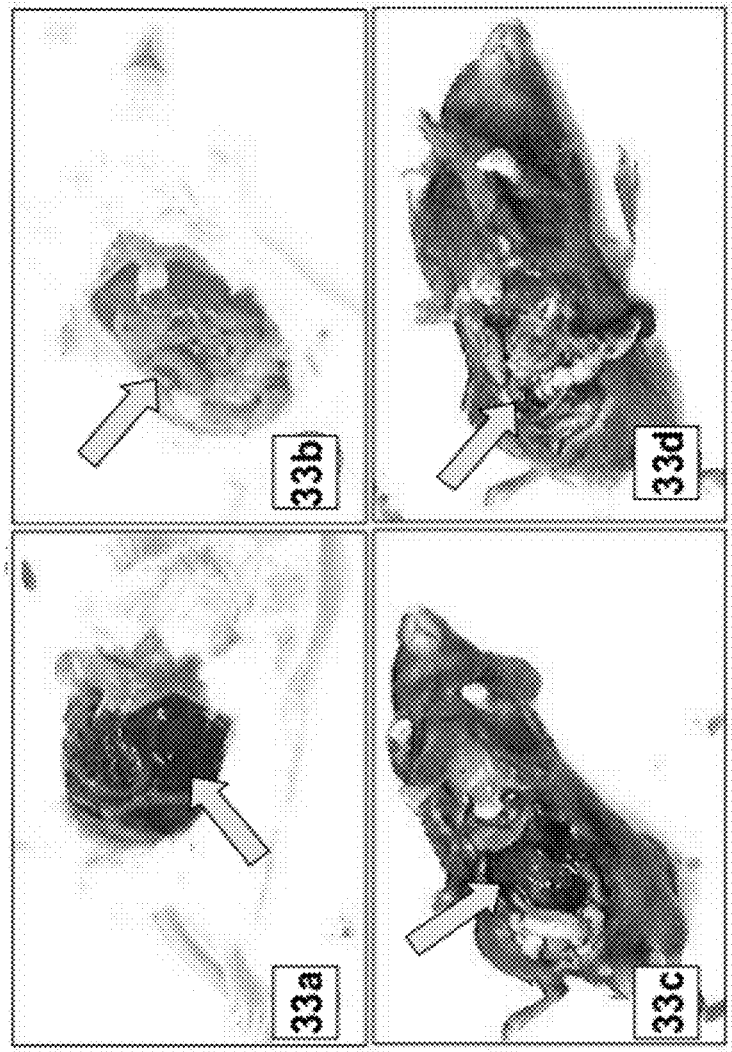
Figures 33a-d

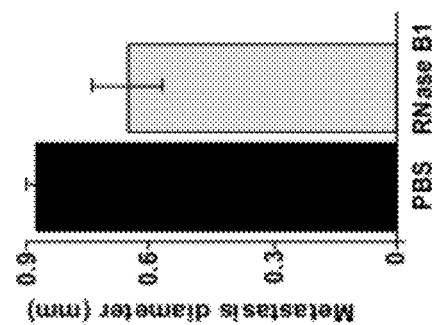
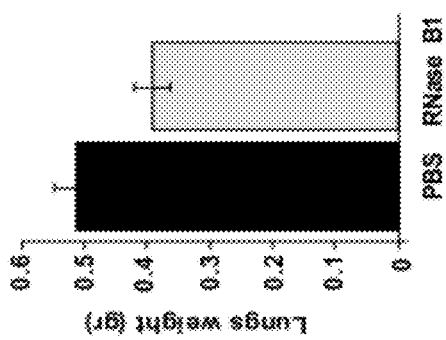
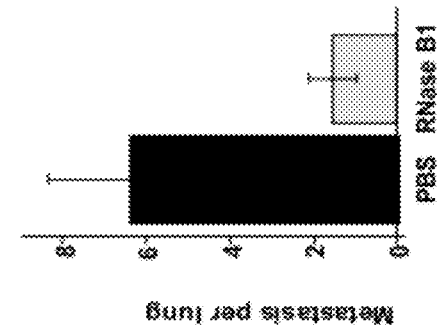

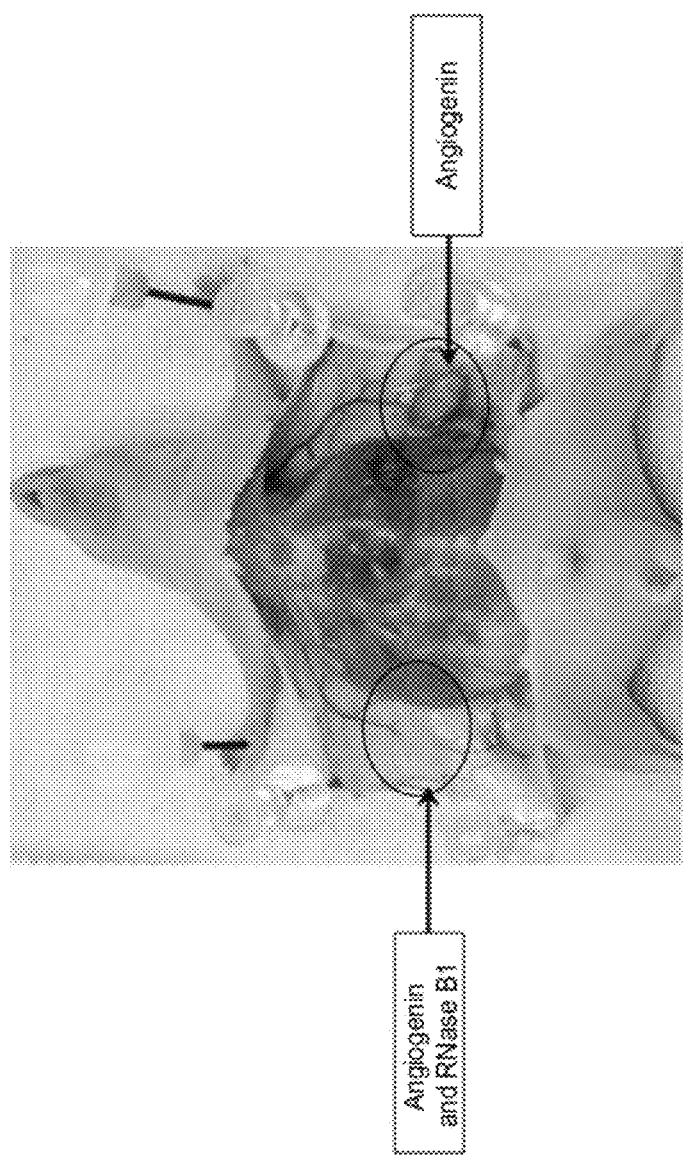

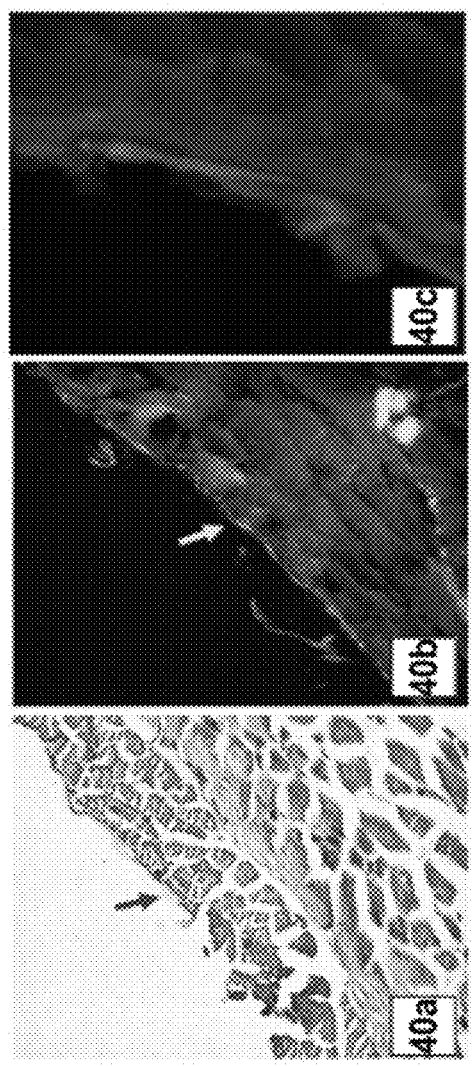
Figures 40a-c

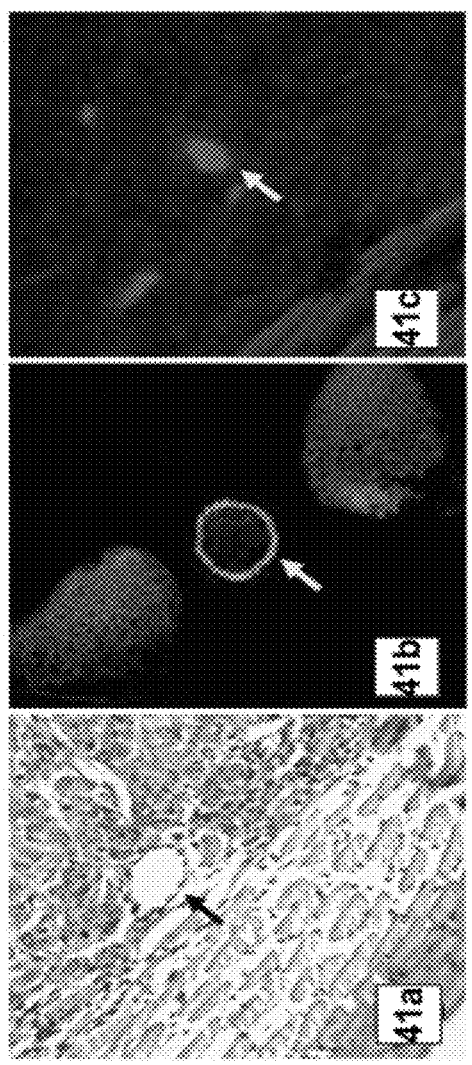
Figures 41a-c

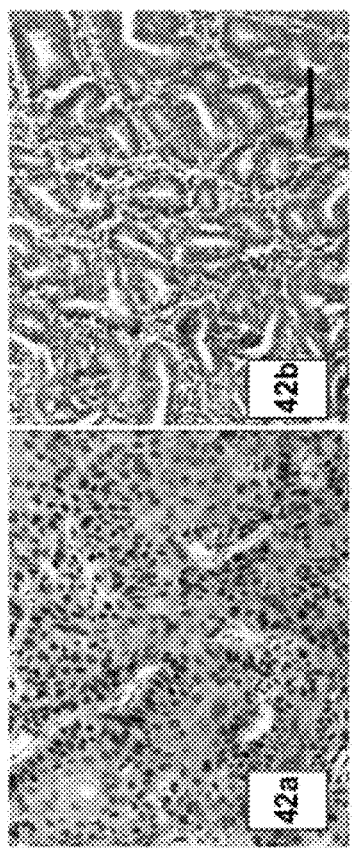
Figures 42a-b

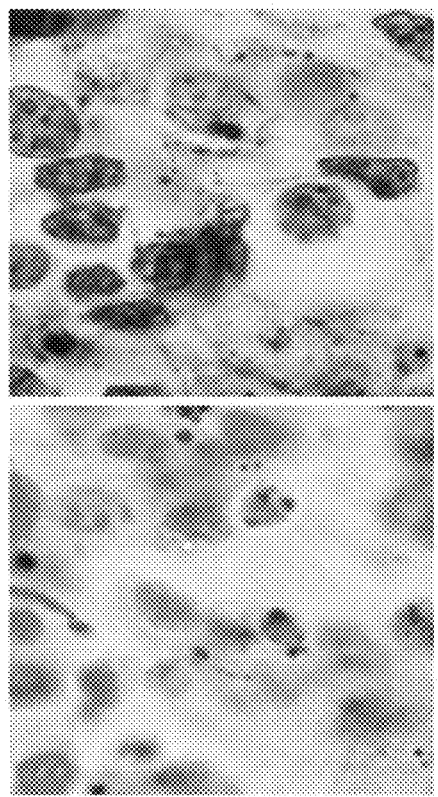

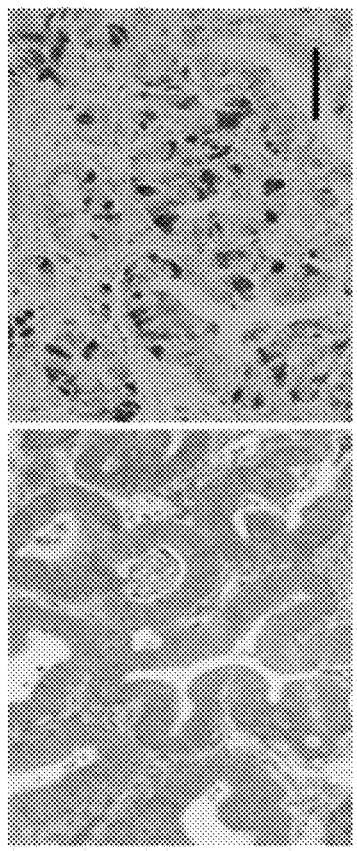

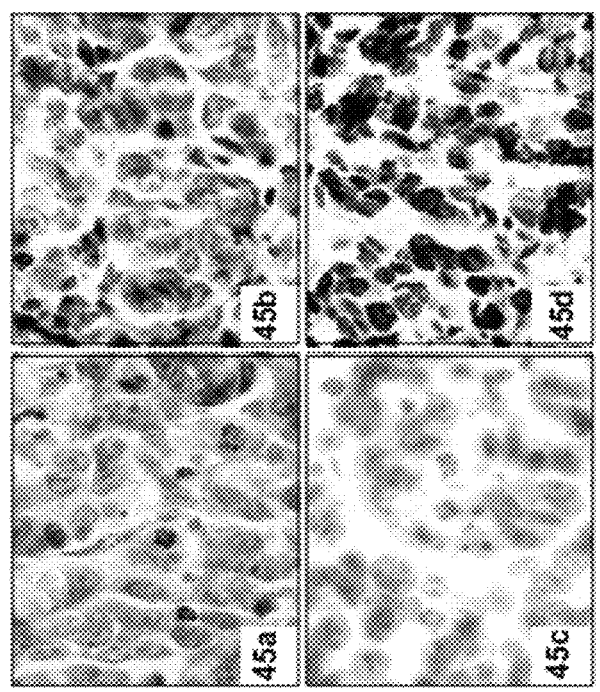
Figures 45a-d

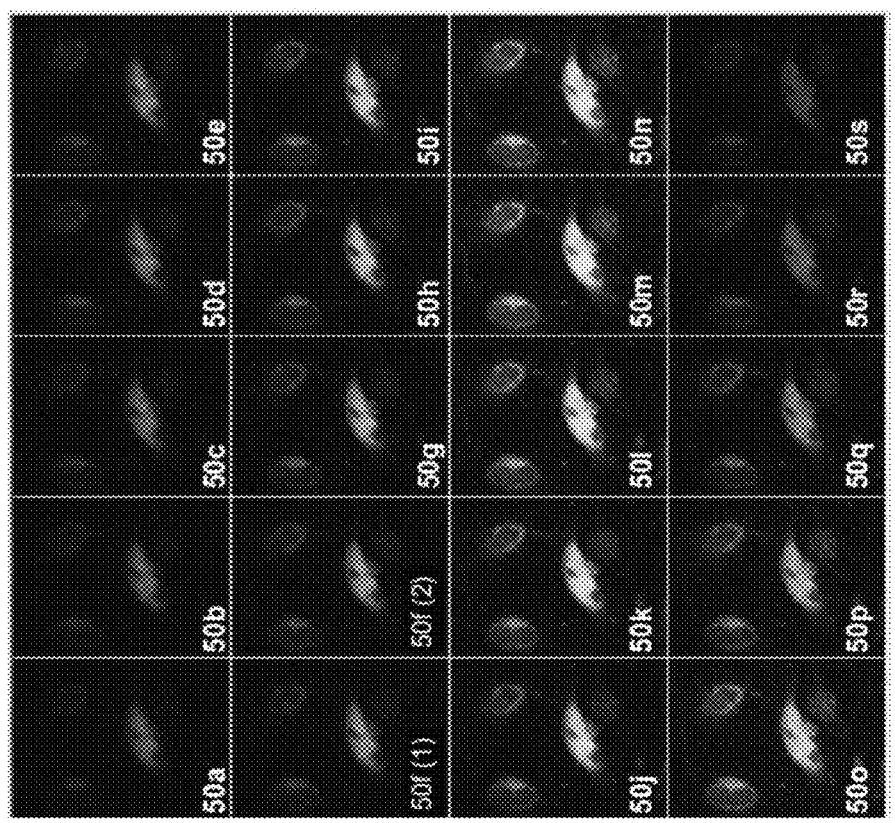
Figures 50a-s

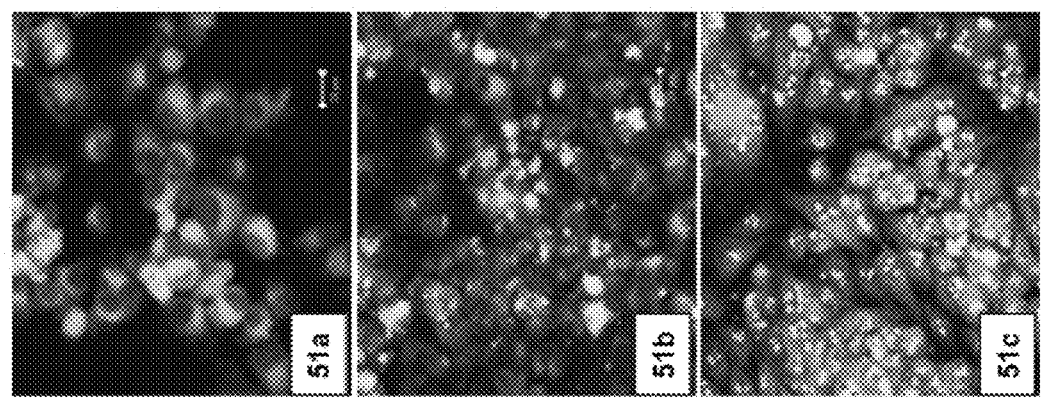
Figures 51a-c

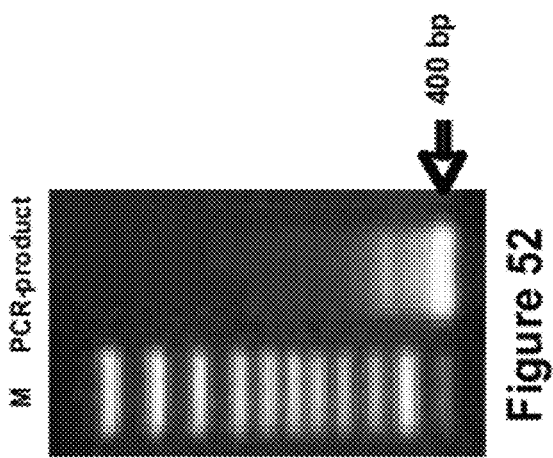

Figure 53

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: synthetic PCR amplification degenerate
      oligonucleotide forward primer having low
      degeneracy according to Aspergillis niger codon
      usage for amino acids F107-N112
```

<400> SEQUENCE: 1
ttytgggarc aygartggaa y                                           21

<210> SEQ ID NO 2
<211> LENGTH: 23
<212> TYPE: DNA
<213> ORGANISM: Artificial Sequence
<220> FEATURE:
<223> OTHER INFORMATION: synthetic PCR amplification degenerate
      oligonucleotide reverse primer having low
      degeneracy according to Aspergillis niger codon
      usage for reverse complement for amino acids Y200-K206
<221> NAME/KEY: modified_base
<222> LOCATION: (6)...(6)
<223> OTHER INFORMATION: n = deoxyinosine (i)

<400> SEQUENCE: 2
ccyttnacrt traartarta rta                                         23

<210> SEQ ID NO 3
<211> LENGTH: 238
<212> TYPE: PRT
<213> ORGANISM: Aspergillis saitoi
<220> FEATURE:
<223> OTHER INFORMATION: ribonuclease M (RNase M)

<400> SEQUENCE: 3

Thr Ile Asp Thr Cys Ser Ser Asp Ser Pro Leu Ser Cys Gln Thr Asp
 1               5                  10                  15

Asn Glu Ala Ser Cys Cys Phe Asn Ser Pro Gly Gly Ser Leu Leu Gln
            20                  25                  30

Thr Gln Phe Trp Asp Tyr Asp Pro Ser Asp Gly Pro Ser Asp Ser Trp
        35                  40                  45

Thr Ile His Gly Leu Trp Pro Asp Asn Cys Asp Gly Ser Tyr Gln Glu
    50                  55                  60

Tyr Cys Asp Asp Ser Arg Glu Tyr Ser Asn Ile Thr Ser Ile Leu Glu
65                  70                  75                  80

Ala Gln Asp Arg Thr Glu Leu Leu Ser Tyr Met Lys Glu Tyr Trp Pro
                85                  90                  95

Asp Tyr Glu Gly Ala Asp Glu Asp Ser Phe Trp Glu His Glu Trp
            100                 105                 110

Asn Lys His Gly Thr Cys Ile Asn Thr Ile Asp Pro Ser Cys Tyr Thr
        115                 120                 125

Asp Tyr Tyr Ala Gln Glu Val Gly Asp Phe Gln Gln Val Val
    130                 135                 140

Asp Leu Phe Lys Thr Leu Asp Ser Tyr Thr Ala Leu Ser Asp Ala Gly
145                 150                 155                 160

Ile Thr Pro Ser Glu Asp Ala Thr Tyr Lys Leu Ser Asp Ile Glu Asp
                165                 170                 175

Ala Leu Ala Ala Ile His Asp Gly Tyr Pro Pro Tyr Val Gly Cys Glu
            180                 185                 190

Asp Gly Ala Leu Ser Gln Leu Tyr Tyr Tyr Phe Asn Val Lys Gly Ser
        195                 200                 205

Ala Ile Gly Gly Thr Tyr Val Ala Ser Glu Arg Leu Glu Asp Ser Asn
    210                 215                 220

Cys Lys Gly Ser Gly Ile Lys Tyr Pro Pro Lys Ser Ser Ser
225                 230                 235

<210> SEQ ID NO 4

<211> LENGTH: 300
<212> TYPE: DNA
<213> ORGANISM: Artificial Sequence
<220> FEATURE:
<223> OTHER INFORMATION: synthetic 300 bp PCR product from Aspergillis
      niger genomic DNA open reading frame cloned into
      pGEM-T vector
<221> NAME/KEY: CDS
<222> LOCATION: (1)...(300)
<223> OTHER INFORMATION: open reading frame

<400> SEQUENCE: 4

```
ttc tgg gag cac gag tgg aac aag cac gga act tgc atc aac acc att      48
Phe Trp Glu His Glu Trp Asn Lys His Gly Thr Cys Ile Asn Thr Ile
 1               5                  10                  15 gag ccc agc tgc tac acc gac tac tac gct cag gag gaa gtt ggt gac      96
Glu Pro Ser Cys Tyr Thr Asp Tyr Tyr Ala Gln Glu Glu Val Gly Asp
             20                  25                  30 ttt ttc cag cag gtc gtt gac ctt ttt aag acc ttg gat tcc tac acc     144
Phe Phe Gln Gln Val Val Asp Leu Phe Lys Thr Leu Asp Ser Tyr Thr
         35                  40                  45 gct ctc tcc gac gcc gga att act ccc tcc gag gat gcc acc tac aag     192
Ala Leu Ser Asp Ala Gly Ile Thr Pro Ser Glu Asp Ala Thr Tyr Lys
     50                  55                  60 ctg agc gac att gag gat gct ctc gcc gcg atc cac gat ggc tac ccc     240
Leu Ser Asp Ile Glu Asp Ala Leu Ala Ala Ile His Asp Gly Tyr Pro
 65                  70                  75                  80 ccg tat gtc ggg tgc gag gac ggt gct ctg tcc cag ctc tac tat tac     288
Pro Tyr Val Gly Cys Glu Asp Gly Ala Leu Ser Gln Leu Tyr Tyr Tyr
                 85                  90                  95 ttc aac gtc aag                                                     300
Phe Asn Val Lys
            100
```

<210> SEQ ID NO 5
<211> LENGTH: 100
<212> TYPE: PRT
<213> ORGANISM: Artificial Sequence
<220> FEATURE:
<223> OTHER INFORMATION: open reading frame amino acid sequence
      identical to F107-K206 of Aspergillis saitoi RNase M except Glu at
      position 17 (E123) of RNase B1 replaces Asp at
      position 17 (D123)

<400> SEQUENCE: 5

```
Phe Trp Glu His Glu Trp Asn Lys His Gly Thr Cys Ile Asn Thr Ile
 1               5                  10                  15

Glu Pro Ser Cys Tyr Thr Asp Tyr Tyr Ala Gln Glu Glu Val Gly Asp
             20                  25                  30

Phe Phe Gln Gln Val Val Asp Leu Phe Lys Thr Leu Asp Ser Tyr Thr
         35                  40                  45

Ala Leu Ser Asp Ala Gly Ile Thr Pro Ser Glu Asp Ala Thr Tyr Lys
     50                  55                  60

Leu Ser Asp Ile Glu Asp Ala Leu Ala Ala Ile His Asp Gly Tyr Pro
 65                  70                  75                  80

Pro Tyr Val Gly Cys Glu Asp Gly Ala Leu Ser Gln Leu Tyr Tyr Tyr
                 85                  90                  95

Phe Asn Val Lys
            100
```

METHODS OF AND COMPOSITIONS FOR INHIBITING THE PROLIFERATION OF MAMMALIAN CELLS

RELATED APPLICATIONS

This application is a continuation of U.S. patent application Ser. No. 12/890,762 filed on Sep. 27, 2010, which is a continuation of U.S. patent application Ser. No. 10/952,495 filed on Sep. 29, 2004, now U.S. Pat. No. 7,811,981, which is a continuation-in-part of U.S. patent application Ser. No. 10/069,454 filed Feb. 26, 2002, now U.S. Pat. No. 7,101,839, which is a National Phase of PCT Patent Application No. PCT/IL00/00514 filed on Aug. 29, 2000, which is a continuation-in-part of U.S. patent application Ser. No. 09/385,411 filed Aug. 30, 1999, now abandoned. The contents of the above applications are incorporated herein by reference in their entirety.

FIELD AND BACKGROUND OF THE INVENTION

The present invention relates to the use of a ribonuclease of the T2 family or a polynucleotide encoding same for preventing, inhibiting and/or reversing proliferation, colonization, differentiation and/or development of abnormally proliferating cells in a subject. The present invention further relates to pharmaceutical compositions containing, as an active ingredient, a ribonuclease of the T2 family or a polynucleotide encoding same for treating proliferative diseases or disorders in general and cancer in particular.

There is an ongoing interest, both within the medical community and among the general population, in the development of novel therapeutic agents for the treatment of cell proliferative diseases and disorders such as cancer.

Agents that display anti-proliferative, anti-colonization, anti-differentiation and/or anti-development properties against mammalian cells can potentially be used as anticancer drugs. As such, these agents are widely sought for from both natural as well as synthetic sources.

RIBASES are ribonucleases (RNases) which display a biological activity which is distinct from their ability to degrade RNA. RIBASES and their structural homologous are known to effect a large number of cellular reactions (Rybak, M. et al., 1991, J. Biol. Chem. 266:21202-21207; Schein, C. H. 1997 Nature Biotechnol. 15:529-536). EDN and ECP, two major proteins found in the secretory granules of cytotoxic eosinophyles (members of RNase A family) are thought to participate in the immune response. In self-incompatible plants stylar S-RNases (members of RNase T2 family), arrest pollen tube growth and thus prevent fertilization. RC-RNase, produced from Bullfrog oocytes, inhibits, in vitro, the growth of tumor cells such as the P388, and L1210 leukemia cell lines and is effective for in vivo killing of sarcoma 180, Erlich, and Mep II ascites cells (Chang, C-F. et al 1988, J. Mol. Biol 283:231-244). Some RNases display limited ribonuclease activity, an example of which includes angiogenins that stimulate blood vessels formation (Fett, J. W. 1985, Biochemistry 24:5480-5486).

Living organisms use extracellular RNases for defense against pathogens and tumor cells. For example, ECP is secreted in response to parasite attack (Newton, D L. 1992, J. Biol. Chem. 267:19572-19578) and displays antibacterial and antiviral activity. This activity is also displayed by Zinc-$\alpha_2$-glycoprotein (Zn$\alpha_2$gp), an RNase present in most human body fluids including blood, seminal plasma, breast milk, synovial fluid, saliva, urine and sweat (Lei G, et al., 1998, Arch Biochem Biophys. July 15; 355(2):160-4).

The specific mechanism by which extracellular RNases function in cellular reactions is unknown.

The main barrier to the cytotoxic activity of some RNase is the cell membrane. ECP was found to form channels in both artificial and cellular membranes. Presumably, ECP released from the granule membrane along with EDN (eosinophylic RNase, which is responsible for cerebellar Purkinjie cell destruction) transfers EDN into the intercellular space. The entrance of the fungal toxin α-sarcin (a member of the RNase A family) into target cells depends upon viral infection which permeabilizes the cellular membrane (Rybak, M. et al., 1991, J. Biol. Chem. 266:21202-21207). It is also possible that RNases enter the cell via endocytosis. When the Golgi-disrupting drugs retinoic acid or monensin were used to artificially deliver BS-RNase into the cells, cytotoxicity increased dramatically (Wu Y, et al., 1995, J Biol. Chem. 21; 270(29): 17476-81).

Cytotoxicity of RNases can be used for therapeutic purposes. Human RNase L is activated by interferon and inhibits viral growth. Expression of the gene for human RNase L together with that for a 2'5'-A synthetase in tobacco plants is sufficient to protect plants from cucumber mosaic virus and to prevent replication of potato virus Y. Human immunodeficiency virus-1 (HIV-1) induces blockade in the RNase L to antiviral pathways (Schein, C. H. 1997 Nature Biotechnol. 15:529-536.). RNases can be fused with specific membranal protein antibodies to create immunotoxins. For example, fusion of RNase A with antibodies to the transferrin receptor or to the T cell antigen CD5 lead to inhibition of protein synthesis in tumor cells carrying a specific receptor for each of the above toxins (Rybak, M. et al., 1991, J. Biol. Chem. 266:21202-21207; Newton D L, et al., 1998, Biochemistry 14; 37(15):5173-83). Since RNases are less toxic to animals, they may have fewer undesirable side effect than the currently used immunotoxins.

The cytotoxicity of cytotoxic ribonucleases appears to be inversely related to the strength of the interaction between a ribonuclease inhibitor (RI) and the RNase. Ribonuclease inhibitor (RI) is a naturally occurring molecule found within vertebrate cells which serves to protect these cells from the potentially lethal effects of ribonucleases. The ribonuclease inhibitor is a 50 kDa cytosolic protein that binds to RNases with varying affinity. For example, RI binds to members of the bovine pancreatic ribonuclease A (RNase A) superfamily of ribonucleases with inhibition constants that span ten orders of magnitude, with $K_i$'s ranging from $10^{-6}$ to $10^{-16}$ M.

A-RNases

ONCONASE, like RNase A and BS-RNase, is a member of the RNase A superfamily. Members of the RNase A superfamily share about 30% identity in amino acid sequences. The majority of non-conserved residues are located in surface loops, and appear to play a significant role in the dedicated biological activity of each RNase. ONCONASE was isolated from Northern Leopard frog (*Rana pipiens*) oocytes and early embryos. It has anti-tumor effect on a variety of solid tumors, both in situ and in vivo (Mikulski S. M., et al., 1990 J. Natl. Cancer 17; 82(2):151-3). ONCONASE has also been found to specifically inhibit HIV-1 replication in infected H9 leukemia cells at non-cytotoxic concentration (Youle R. J., et al., 1994, Proc. Natl. Acad. Sci. 21; 91(13):6012-6).

Although the RNase activity of ONCONASE is relatively low, it is accepted that the enzymatic and cytotoxic activities thereof are associated to some degree. It is believed that the tertiary structure of A-RNases differentiate between cytotoxic and non-cytotoxic types. For example, differences between the tertiary structure of ONCONASE and RNase A are believed to be responsible for the increased cytotoxicity observed for ONCONASE. ONCONASE, unlike RNase A, contains a blocked N-terminal Glu1 residue (pyroglutamate) which is essential for both enzymatic and cytotoxic activities. This unique structure enables ONCONASE to permeate into target cells (Boix E., et al., 1996, J. Mol. Biol. 19:257(5):992-1007). In addition, in ONCONASE the Lys9 residue replaces the Gln11 residue of RNase A, which is believed to effect the structure of the active site. Furthermore, differences in the amino acid sequence of the primary structure between ONCONASE and RNase A cause topological changes at the periphery of the active site which effect the specificity thereof (Mosimann S. C., et al., 1992, Proteins 14(3):392-400).

The differences in toxicity between A-RNases are also attributed to their ability to bind RI. Bovine seminal ribonuclease (BS-RNase) is 80% identical in its amino acid sequence to RNase A, but unlike other members of the RNase A superfamily, BS-RNase exists in a dimeric form. It has been shown that the quaternary structure of BS-RNase prevents binding by RI, thereby allowing the enzyme to retain its ribonucleolytic activity in the presence of RI (Kim et al., 1995, J. Biol. Chem. 270 No. 52:31097-31102). ONCONASE, which shares a high degree of homology with RNase A, is resistant to binding by RI. The RI-ONCONASE complex has a $K_d$ at least one hundred million times less than that of the RI-RNase A complex. The lower binding affinity of ONCONASE for RI prevents effective inhibition of the ribonucleolytic activity and could explain why ONCONASE is cytotoxic at low concentrations while RNase A is not.

It is suggested that binding to cell surface receptor is the first step in ONCONASE cytotoxicity. Nothing is known about the nature of ONCONASE receptors on mammalian cell surfaces. ONCONASE may bind to cell surface carbohydrates as in the case of ricin, or it may bind to receptors originally developed for physiologically imported molecules like polypeptide hormones (Wu Y, et al., 1993, J. Biol. Chem. 15; 268(14):10686-93). In mice, ONCONASE was eliminated from the kidneys in a rate 50-100-fold slower than did RNase A. The slower elimination rate of ONCONASE is explained as a result of its higher ability to bind to the tubular cells and/or by its resistance to proteolytic degradation. The strong retention of ONCONASE in the kidneys might have clinical implications (Vasandani V. M., et al., 1996, Cancer Res. 15; 56(18):4180-6). ONCONASE may also bind to Purkinjie cells EDN receptors (Mosimann S. C., et al., 1996, J. Mol. Biol. 26; 260(4):540-52). The specificity of ONCONASE is also expressed in its tRNA preference. In rabbit reticulocyte lysate and in *Xenopus* oocytes it was discovered that ONCONASE inhibits protein synthesis via tRNA, rather than via rRNA or mRNA degradation. In contrast, RNase A degrades mostly rRNA and mRNA (Lin J. J., et al., 1994, Biochem. Biophys. Res. Commun 14; 204(1):156-62).

Treatment of susceptible tissue cultures with ONCONASE results in the accumulation of cells arrested in G1 phase of the cell cycle, having very low level of RNA contents (Mosimann S. C., et al., 1992, Proteins 14(3):392-400). In glioma cells ONCONASE inhibited protein synthesis without a significant reduction in cell density, showing that ONCONASE is also cytotoxic to cells in addition to being cytostatic (Wu Y., et al., 1993, J. Biol. Chem. 15; 268(14):10686-93). ONCONASE, combined with chemotherapeutic agents, can overcome multidrug resistance. Treatment with vincristine and ONCONASE increased the mean survival time (MST) of mice carrying vincristine resistant tumors to 66 days, compared to 44 days in mice treated with vincristine alone (Schein, C. H., 1997, Nature Biotechnol. 15:529-536).

Furthermore, some chemotherapeutic agents may act in synergy with ONCONASE. In tumor cell lines of human pancreatic adenocarcinoma and human lung carcinoma treated with a combination of ONCONASE and tamoxifen (anti-estrogen), trifluoroperazine (Stelazine, calmodulin inhibitor) or lovastatin (3-hydroxyl-3-methylglutatyl coenzyme A (HMG-CoA) reductase inhibitor) a stronger growth inhibition was observed than cells treated with ONCONASE alone (Mikulski S. M., et al., 1990, Cell Tissue Kinet. 23(3):237-46). Thus, a possibility of developing combination therapy regiments with greater efficiency and/or lower toxicity is clear.

Bovine seminal RNase is a unique member of RNase A family, since it is the only RNase containing a dimmer of RNase A-like subunits linked by two disulfide bridges. In addition, it maintains allosteric regulation by both substrate and reaction products. The regulation occurs at the cyclic nucleotide hydrolysis phase. It has the ability to cleave both single- and double-stranded RNA. BS-RNase is highly cytotoxic. It displays anti-tumor effect in vitro on mouse leukemic cells, HeLa and human embryo lung cells, mouse neuroblastoma cells, and human fibroblasts and mouse plasmacytoma cell lines. When administrated in vivo to rats bearing solid carcinomas (thyroid follicular carcinoma and its lung metastases), BS-RNase induced a drastic reduction in tumor weight, with no detectable toxic effects on the treated animals (Laccetti, P. et al., 1992, Cancer Research 52:4582-4586). Artificially monomerized BS-RNase has higher ribonuclease activity but lower cytotoxicity than native dimeric BS-RNase (D'Allessio G., et al., 1991, TIBS:104-106). This, again, indicates the importance of molecular structure for the biological activity. It seems that like ONCONASE, BS-RNase binds to recognition site(s) on the surface of the target cells, prior to penetration into target cells.

In addition to being cytotoxic, BS-RNase is also immunorepressive. BS-RNase can block the proliferation of activated T cells, and prolong the survival of skin grafts transplanted into allogenetic mice. The immunorepressive activity of SB-RNase is explained by the need to protect sperm cells from the female immune system.

T2-RNases

In plants, self-compatibility is abundant and is effective in preventing self-fertilization. Pollen carrying a particular allele at the S locus, which controls self-incompatibility, is unable to fertilize plants carrying the same S-allele. In many self-incompatible plants, especially members of *Solanaceae* and *Rosaceae*, S-RNase, a member of the T2-RNase family is secreted by the female organs. S-RNase specifically recognize self-pollen and arrest its growth in the stigma or style before fertilization occurs (Clarke, A. E. and Newbigin, E., 1993, Ann. Rev. Genet. 27:257-279) it is believed that the arrest of pollen tube growth is a direct consequence of RNA degradation, however the mode of S-RNase entrance into the tube cell is still obscure.

Members of RNase T2 family were first identified in fungi (Egami, F. and Nakamura, K. 1969, Microbial ribonucleases. Springer-Verlag, Berlin). Since, they were found in a wide variety of organisms, ranging from viruses to mammals. In particular, T2-RNases show much broader distribution than the extensively described RNase A family. However, the in vivo role of T2-RNases in mammalian cells is still not known.

In microorganisms, extracellular T2-RNases are generally accepted to contribute to the digestion of polyribonucleotides present in the growth medium, thereby giving rise to diffusible nutrients. They may also serve as defense agents (Egami, F. and Nakamura, K., 1969, Microbial ribonucleases. Springer-Verlag, Berlin).

In plants, T2-RNases play a role in the pollination process, by selectively limiting the elongation of pollen tubes racing towards the ovules (Roiz, L. and Shoseyov, O, 1995, Int. J. Plant Sci. 156:37-41, Roiz L. et al., 1995, Physiol. Plant. 94:585-590). To date, the mechanism by which these RNases affect pollen tubes is unclear.

Thus, there exist few examples of cytotoxic ribonucleases which can be effectively used as cancer treatment agents. New ribonucleases with anti-proliferation, anti-colonization, anti-differentiation and/or anti-development activities toward mammalian cells are needed to enhance the spectrum of therapeutic agents available for treatment of human cancers, to thereby open new horizons in the field of cancer treatment.

Apoptosis and Disease

Cell death can occur through two different processes, termed necrosis and apoptosis, which can be distinguished by specific sets of functional and morphologic characteristics. Necrosis is a traumatic cell death that occurs as a response to injurious agents in the extracellular surroundings e.g. hypoxia, hyperthermia, viral invasion, exposure to toxins, or attack by pathogens. The ion and water pumps in the plasma membrane lose their abilities to maintain concentration gradients, the cells and mitochondria swell and eventually burst, leaking cellular constituents and leading to an inflammatory response in the surrounding tissue. In apoptosis, or programmed cell death (PCD), cells are induced to self-destruct via an intrinsic genomic program. The cells shrink and the mitochondria break down and release cytochrome c. The nuclear DNA is gradually degraded into monomers and multimers of about 200 bases. Eventually, the cells undergo blebbing, and break into small, membrane-wrapped fragments called apoptotic bodies which are engulfed by nearby phagocytotic cells (Rudin C M and Thompson C B. 1997. Annu Rev Med. 48:267-81; Chamond R. R. et al. 1999. Alergol Immunol Clin. 14:367-374). Significantly, no inflammatory response in surrounding tissues is elicited. The difference between death forms is summarized in the following Table 1.

tion, and in the aging process (Herndon F J. et al. 1997. Mechanism of ageing and development 94:123-134).

Apoptosis is needed to remove cells that represent a threat to the integrity of the organism. For example, it is the mechanism by which cytotoxic T lymphocytes (CTLs) kill virus-infected cells (Barber G N. 2001. Cell Death Differ. 8:113-126.). CTLs can induce apoptosis even in each other, so they can be eliminated after completion of their physiological function, preventing their becoming a liability for surrounding tissue (Duke R C. 1992. Semin Immunol. 4:407-412).

The anterior chamber of the eye and the testes are known as "immune to privileged" organs, as it has been found antigens do not elicit an immune response in these sites. In these sites, the cells constitutively express high levels of Fas ligand (FasL), a cytokine that binds to a cell-surface receptor named Fas (also called CD95) and known as a potent death activator. FasL is toxic to T cells, and thus permits the prolonged, and sometimes permanent, survival of foreign tissue and tumor grafts (inhibited apoptosis) (Niederkorn J Y. 2002. Crit. Rev Immunol. 22:13-46; Takeuchi T. et al. 1999. J. Immunol. 162:518-522; Sugihara A, et al. 1997. Anticancer Res. 17:3861-3865). Thus, upregulation of apoptotic processes in specific cells, for example lymphocytes, can be useful in the prevention of graft rejection, potentially leading to reduction in the use of immunosuppressive drugs and improvement in the quality of the patient's life.

A variety of diseases have been associated with regulation of apoptosis. Among them are various neurodegenerative diseases, among them Alzheimer's disease, Parkinson's disease, amyotrophic lateral sclerosis, retinitis pigmentosa, and epilepsy, all associated with selective apoptosis of the neurons. This neuronal death appears to be associated to increase susceptibility to apoptosis in these cells.

Mature blood cells are derived from haematopoietic precursors located in the bone marrow. Haematopoiesis, as well as maintenance of mature blood cells are regulated by a

TABLE 1

Apoptosis vs. Necrosis

| | Necrosis | Apoptosis |
|---|---|---|
| Etiology | Acute cell injury due to extracellular stimuli | Various intracellular or extracellular stimuli |
| Character | Pathologic | Physiologic or pathologic |
| Distribution | Groups of cells or patches of tissues | Wildly scattered isolated cells |
| Energy requirement | Passive process (ATP-independent) | Active process (ATP-dependent) |
| Morphologic features | Swelling of the cytoplasm. Membrane lysis with loss of cell and organelles contents. | Shrinkage of the cytoplasm, Externalization of phosphatidylserine. Cell membrane blebbing to form apoptotic bodies encompassing cytoplasm and organelles. Chromatin condensation and DNA fragmentation into multimers of 200 bases. |
| Reaction of the surrounding tissue | Inflammation | Phagocytosis without inflammatory reaction |

(Nikitakis N. G. et al. 2004. Oral Surg Oral Med Oral Pathol Oral Radiol Endod. 97: 476-90.)

Apoptosis plays a central role in the regulation of homeostasis, in normal, and in pathological processes. During embryogenesis apoptosis is responsible for the disappearance of the tadpoles tail, the differentiation of fingers and toes, and the removal of unnecessary neurons in the brain. It is also involved in disassembly of the endometrium at the menstruation.

number of trophic factors (erythropoyetin, colony stimulating factors, cytokines). The balance between hematopoietic cell production and elimination is regulated by apoptosis. Loss of apoptosis regulation can be associate with a variety of blood disorders e.g. aplastic anemia, myelodyplastic syndrome, $CD4^+$ T cells lymophocytopenia and G6PD deficiency.

In myocardial infarction and cerebrovascular accidents, ischaemic renal damage and polycystic kidney the cells surrounding the ischaemic zone are eliminated through apoptosis.

There is evidence showing that apoptosis is upregulated in a variety of cells e.g. neurons, myocytes, lymphocytes, hepatocytes, and that aging enhances apoptosis under physiological conditions that cause homeostasis dysfunction, such as oxidative stress, glycation, and DNA damage.

Apoptosis has been described in inflammatory cells (eosinophils, neutrophils, lymphocytes, macrophages, mast cells) that participate in the late and chronic stages of allergy (Sampson A P. 2000. Clin Exp Allergy. 30 Suppl 1:22-7; Haslett C. 1999. Am J Respir Crit. Care Med. 160:S5-11). For example, apoptotic death of the eosinophils is associated with bronchial asthma, allergic rhinitis and atopic dermatitis (Wooley K L et al. 1996. Am J Respir Crit. Care Med; 154: 237-243; Boyce J A. Allergy Asthma Proc. 18: 293-300). Lymphocytes apoptosis may induced by allergens, such as *Olea europaea* and *Lolium perenneinduce* (Guerra F et al. 1999. Hum Immunol; 60: 840-847).

Diseases associated with inhibition of apoptosis include those diseases in which an excessive accumulation of cells occurs (neoplastic diseases, autoimmune diseases). Where it was once believed that the excessive accumulation of cells in these diseases was due to an increased cell proliferation, it is now thought to be due to defective apoptosis.

In both solid and haematological tumors, the malignant cells show an abnormal response to apoptosis inducers (Watson A J M. 1995. Gut 37: 165-167; Burch W. et al. 1992. Trends Pharmacol Sci 13:245-251). In these diseases cycle-regulating genes such as p53, ras, c-myc and bcl-2 suffer mutations, inactivation or dysregulations associated to malignant degeneration (Merrit A J et al. 1994. Cancer Res 54:614-617; Iwadate Y et al. 1996. Int J Cancer 69:236-240; Müllauer L et al. 1996. Hepatology 23: 840-847; Newcomb E W. 1995. Leuk Lymphoma 17: 211-221). The expression of bcl-2 is considered to be a predictive factor for worse prognosis in prostate and colonic cancer and in neuroblastoma (Thompson C B. 1995. Science 267: 1456-1462). It has been shown that a number of antineoplastic therapies induce apoptosis in tumour cells (for reviews see: Sun S Y et al. 2004. J Natl Cancer Inst. 96:662-672; Schulze-Bergkamen H and Krammer P H. 2004. Semin Oncol. 31:90-119; Abend M. 2003. Int J Radiat Biol. 79:927-941).

Defects in the apoptosis may lead to autoimmune diseases such as lupus erythematosus (Carson D A. and Rebeiro J M. 1993. Lancet. 341: 1251-1254. Aringer M. et al. 1994. Arthritis Rheum. 37:1423-1430), rheumatoid arthritis (Liu H. and Pope R M. 2003. Curr Opin Pharmacol. 3:317-22.) and myasthenia gravis (Masunnaga A. et al. 1994. Immunol Lett. 39: 169-172.).

There are several ways by which the pathogens interfere with apoptosis. For example adenovirus and Epstein-Barr virus (associated with several lymphoid and to epithelial malignancies) promote expression of Bcl-2 oncogene (Thompson C B. 1995. Science 267:1456-1462; Marshall W L. et al. 1999. J. Virol. 73:5181-5185), cowpox encode a protease inhibitor that inactivates caspases (Deveraux Q L, et al. 1999. J Clin Immunol. 19:388-98.); chlamydia interferes with mitochondrial cytochrome c release into the cytosol (Fan T. et al. 1998. J Exp Med. 187:487-496).

In chronic inflammatory, hyperproliferative skin diseases such as psoriasis, an abnormally low rate of apoptosis contributes to the development of epidermal hyperplasia. It was shown that keratinocytes respond to a variety of external and internal growth factors, including some proinflammatory cytokines which may suppress keratinocytes apoptosis, such as IL-15 (Ruckert R. et al. 2000. J. Immunol. 165:2240-2250).

Actin and Cell Motility

Actin is ubiquitous in nature, comprising the cytoskeleton and providing motility in all types of cells. The cellular actin cytoskeleton is organized in a variety of spatially and temporally controlled assemblies of actin filaments. Actin filaments are polymerized from monomeric G-actin in lamellipodia and filopodia at the cell periphery. These newly polymerized actin filaments are highly dynamic and are turned over rapidly (Wang, 1985). The actin filaments found in the remainder of the cells have their origin in the lamellipodium and in small membrane ruffles occurring throughout the lamella. Actin filaments are organized into various arrays such as stress fibers, lamellipodial networks, filopodial bundles, dorsal arcs, peripheral concave or convex bundles as well as geodesic arrays (Small, et al. Trends in Cell Biol 2002; 12:112-20). The organization of each of these assemblies is controlled and stabilized by specific sets of actin-associated proteins, conferring on them different functions. An asymmetric and polarized organization of the different actin arrays in cells is fundamental for cell migration, growth, division, differentiation, and defense (Hilpela et al, Mol Cell Biol 2003; 14:3242-53).

Cell motility depends on the cyclic dynamics of polymerization and depolymerization of the actin cytoskeleton. Cell motility involves protrusion of a cell front and subsequent retraction of the rear. Protrusion is based on the forward, cyclic growth, or polymerization of actin filaments in lamellipodia and filopodia. Retraction, on the other hand, is based on the interaction of preformed actin filaments with myosin-II in contractile bundles. Microscopic studies have shown a continuum of retrograde flow of actin behind lamellipodia, indicating that a proportion of filaments generated in the lamellipodium contribute to the network of actin that makes up the rest of the actin cytoskeleton. Thus, actin filaments are generated in the lamellipodia, shed their associate proteins as they become incorporated into the actin cytoskeleton, and then acquire other actin-associated proteins, particularly contractile proteins such as myosin-II, becoming contractile bundles in preparation for retraction of the cell protrusions.

Cell shape change and motility are involved in pathological events, such as cancer metastasis, inflammatory disease, neurodegenerative disease and the like. Cell motility associated proteins have been identified in the pathogenesis of a number of diseases, such as Wiskott-Aldrich Syndrome (WAS protein).

A large and growing number of proteins are known to regulate and modulate the state of the actin cytoskeleton, and some appear to have partly overlapping functions. These include actin and integrin binding proteins such as filamin, talin, Arp 2/3 complex, α-actinin, filament severing proteins and barbed end capping proteins (for review, see Brakebusch et al, EMBO Journal, 2003; 22:2324-33). In addition, there exist proteins of different upstream signaling pathways leading to changes in the actin cytoskeleton and cell morphology and behavior such as the small Ras-related GTPases, e.g., Rac, Rho, and Cdc42. In addition to these small GTPases, phosphoinositides and calcium are known to regulate actin dynamics and cell migration.

Presently, very few specific inhibitors of cell motility are available, even though a great potential exists for such drugs as a complement to existing therapies for inflammatory disease, cancer, neurodegenerative disease and the like. For example, cell shape change and motility are involved at two rate-limiting steps in cancer progression: angiogenesis (i.e., blood vessel recruitment) and metastasis (i.e., spreading of a tumor from one location in the body to other locations), in the extravasation of lymphocytes from vascular elements in inflammatory disease, and in the invasive progression of many cellular parasites into infected host tissue. In combination with cell growth inhibitors, treatment with specific cell motility inhibitors has the potential to provide a more efficacious treatment of diseases of cell motility and proliferation such as inflammatory disease, cancer, infections and the like, analogous to the multiple drug approach for treatment of HIV infection and AIDS.

A number of compounds that target actin directly are known to be effective in modulating cell motility. The best known compounds are the cytochalasins, which are cell-permeable destabilizers of actin filaments, and phalloidin, which is a cell-impermeable stabilizer of actin filaments (J. A. Cooper, J. Cell Biol, 105 (1987)). In addition, latrunculins are cell-permeable disrupters of actin filaments (I. Spector, Science, 219, 493 (1983)). Jasplakinolide is a cell-permeable stabilizer of actin filaments (M. R. Bubb et al., Chem., 269, 14869 (1994)). A few compounds that target proteins upstream of the actin cytoskeleton are known, such as the Rho-kinase inhibitor Y-27632 (M. Uehata et al., Nature, 389, 990 (1997), and myosin light chain kinase inhibitors, such as ML-g (M. Saitoh et al., Biochem. Biophys, Res. Commun., 140, 280 (1986)). Recently, a cyclic peptide dimer was discovered that inhibits the activity of N-WASP, a protein involved in Cdc42-mediated actin nucleation by the Arp2/3 complex (J. R. Peterson et al., Proc. Natl. Acad. Sci. USA, 98, 10624 (2001)). Nevertheless, there is a dearth of available compounds that affect actin dynamics and cell motility.

There is thus a widely recognized need and it would be highly advantageous to have a ribonuclease of the T2 family having actin binding activity, that has potential usefulness in the treatment and prevention of cell motility-associated disease such as inflammatory disease, cancer, neurodegenerative disease and infectious disease.

SUMMARY OF THE INVENTION

According to one aspect of the present invention there is provided a method of preventing, inhibiting and/or reversing proliferation, colonization, differentiation and/or development of abnormally proliferating cells in a subject, the method comprising the step of administering to the subject a therapeutically effective amount of a ribonuclease of the T2 family.

According to another aspect of the present invention there is provided a method of preventing, inhibiting and/or reversing proliferation, colonization, to differentiation and/or development of abnormally proliferating cells in a subject, the method comprising the step of administering to the subject a therapeutically effective amount of a polynucleotide encoding and capable of expressing in vivo a recombinant ribonuclease of the T2 family.

According to yet another aspect of the present invention there is provided methods of (i) treating a tumor in a subject; (ii) preventing, inhibiting and/or reversing the development a tumor in a subject; (iii) preventing, inhibiting and/or reversing transformation of a benign tumor to a malignant tumor in a subject; (iv) preventing, inhibiting and/or reversing tumor angiogenesis in a subject; (v) reducing the number of individual tumors in a subject; (vi) reducing tumor size in a subject; (vii) reducing a number of malignant tumors in a subject; and (viii) preventing, inhibiting and/or reversing transformation of a tissue into a tumor in a subject, each of the methods is effected by administering to the subject a therapeutically effective amount of a ribonuclease of the T2 family or a therapeutically effective amount of a polynucleotide encoding and capable of expressing in vivo a recombinant ribonuclease of the T2 family.

According to still another aspect of the present invention there is provided a pharmaceutical composition comprising, as an active ingredient, a ribonuclease of the T2 family, and a pharmaceutically acceptable carrier.

According to an additional aspect of the present invention there is provided a pharmaceutical composition comprising, as an active ingredient, a polynucleotide encoding and capable of expressing in vivo a recombinant ribonuclease of the T2 family, and a pharmaceutically acceptable carrier.

According to yet an additional aspect of the present invention there is provided a method of preparing a medicament useful in preventing, inhibiting and/or reversing proliferation, colonization, differentiation and/or development of abnormally proliferating cells comprising the step of combining a ribonuclease of the T2 family with a pharmaceutically acceptable carrier.

According to still an additional aspect of the present invention there is provided a method of preparing a medicament useful in preventing, inhibiting and/or reversing proliferation, colonization, differentiation and/or development of abnormally proliferating cells comprising the step of combining a polynucleotide to encoding and capable of expressing in vivo a recombinant ribonuclease of the T2 family with a pharmaceutically acceptable carrier.

According to further features in preferred embodiments of the invention described below, the ribonuclease of the T2 family substantially lacks ribonucleolytic activity. As used herein the phrase "substantially lacks ribonucleolytic activity" refers to (i) an inactivated ribonuclease (either natural or recombinant) of the T2 family which has 0-10% ribonucleolytic activity as is compared to a similar, non-inactivated, ribonuclease; and/or (ii) a recombinant mutant (natural or man induced) ribonuclease of the T2 family which has 0-10% ribonucleolytic activity as is compared to a similar, non-mutant, ribonuclease. Inactivating the ribonucleolytic activity of the ribonuclease of the T2 family may be effected by a process selected from the group consisting of boiling, autoclaving and chemically denaturing.

According to still further features in the described preferred embodiments the abnormally proliferating cells are cancerous cells.

According to still further features in the described preferred embodiments the step of administering to the subject the therapeutically effective amount of the RNase of the T2 family is effected by an administration mode selected from the group consisting of oral administration, topical administration, transmucosal administration, parenteral administration, rectal administration and by inhalation.

According to still further features in the described preferred embodiments the ribonuclease of the T2 family is RNase B1.

According to still further features in the described preferred embodiments the ribonuclease of the ribonuclease T2 family is selected from the group consisting of RNase T2, RNase Rh, RNase M, RNase Trv, RNase hp, RNase Le2, RNase Phyb, RNase LE, RNase MC, RNase CL1, RNase Bsp1, RNase RCL2, RNase Dm, RNase Oy and RNase Tp.

According to still further features in the described preferred embodiments the medicament is identified as providing a treatment for a specified proliferative disorder or disease, such as a specified cancer.

According to still further features in the described preferred embodiments the abnormally proliferating cells are cell associated with a proliferative disorder or disease selected from the group consisting of: papilloma, blastoglioma, Kaposi's to sarcoma, melanoma, lung cancer, ovarian cancer, prostate cancer, squamous cell carcinoma, astrocytoma, head cancer, neck cancer, bladder cancer, breast cancer, colorectal cancer, thyroid cancer, pancreatic cancer, gastric cancer, hepatocellular carcinoma, leukemia, lymphoma, Hodgkin's disease, Burkitt's disease, arthritis, rheumatoid arthritis, diabetic retinopathy, angiogenesis, restenosis, in-stent restenosis and vascular graft restenosis, proliferative vitreoretinopathy, chronic inflammatory proliferative disease, dermatofibroma and psoriasis.

According to yet an additional aspect of the present invention, there are provided methods of treating or preventing diseases or conditions characterized by: (i) excessive cell motility; or (ii) abnormal accumulation of cells in a subject in need thereof. Each of the methods is effected by administering to the subject a therapeutically effective amount of a ribonuclease of the T2 family or a therapeutically effective amount of a polynucleotide encoding and capable of expressing in vivo a recombinant ribonuclease of the T2 family.

According to still further features of the described preferred embodiments, the disease or condition characterized by excessive cellular motility is selected from the group consisting of an inflammatory disease, a neurodegenerative disease and a cancer.

According to yet further features of the described preferred embodiments, the disease or condition characterized by excessive cellular motility is a cancer.

According to further features of the described preferred embodiments, administering to the subject the therapeutically effective amount of said ribonuclease of the T2 family or the expressible polynucleotide encoding the ribonuclease is effected by an administration mode selected from the group consisting of oral administration, intravenous administration, subcutaneous administration, systemic administration, topical administration, transmucosal administration, parenteral administration, rectal administration and inhalation.

According to still another aspect of the present invention, there are provided methods for (i) inhibiting the motility of a cell; (ii) inhibiting actin filament assembly and disassembly in a cell; and (iii) enhancing apoptosis of a cell. Each of the methods is effected by providing to the cell an effective concentration of a ribonuclease of the T2 family or a therapeutically effective amount of a to polynucleotide encoding and capable of expressing in vivo a recombinant ribonuclease of the T2 family.

According to further features in the described preferred embodiments, the ribonuclease of the T2 family is a recombinant protein, expressed in a heterologous expression system. The heterologous system can be a bacterial expression system, yeast expression system and higher cell expression system.

According to still further features of the described preferred embodiments, the ribonuclease activity of the ribonuclease protein is thermostable.

According to yet further features of the described preferred embodiments, the ribonuclease of the T2 family is substantially devoid of ribonuclease activity.

According to further features of the described preferred embodiments, a ribonuclease activity of the ribonuclease protein is thermostable.

According to still further features of the described preferred embodiments, an actin binding activity of the ribonuclease protein is thermostable.

According to yet further features of the described preferred embodiments, the ribonuclease of the T2 family having actin binding activity can be RNase T2, RNase Rh, RNase M, RNase Trv, RNase Up, RNase Le2, RNase Phyb, RNase LE, RNase MC, RNase CL1, RNase Bsp1, RNase RCL2, RNase Dm, RNase Oy and RNase Tp.

According to further features of the described preferred embodiments, the expressible polynucleotide is selected capable of stable integration into a genome of the cell or of a cell of the subject.

According to still further features of the described preferred embodiments, the cell is a cancer cell.

According to still further features of the described preferred embodiments, the providing is effected in vitro or in vivo.

According to still another aspect of the present invention, there are provided a method of isolating a thermostable ribonuclease of the T2 family. The method comprises the steps of: heat denaturating a sample which comprises cells expressing a ribonuclease of the T2 family so as to obtain a heat denatured sample, isolating a supernatant of the heat denatured sample; identifying a fraction of the supernatant to having a thermostable ribonuclease of the T2 family; and purifying the fraction having the thermostable ribonuclease of the T2 family from the supernatant to substantial purity.

According to still further features of the described preferred embodiments the heat denaturing is effected by a temperature of at least 90° C., for at least 10 minutes.

According to yet further features of the described preferred embodiments, identifying the fraction is effected by monitoring ribonucleolytic activity and/or gel electrophoresis.

According to further features of the described preferred embodiments, purifying the fraction is effected by column chromatography.

According to yet another aspect of the present invention there is provided a method of inactivating a ribonuclease activity, yet maintaining an actin binding activity of a ribonuclease of the T2 family, the method effected by subjecting the ribonuclease to denaturing conditions sufficient for substantially inactivating the ribonuclease activity, yet maintaining the actin binding activity.

According to further features of the described preferred embodiments, the inactivating of the ribonuclease activity is effected by autoclaving and/or chemical denaturation.

According to still further features of the described preferred embodiments the ribonuclease is a recombinant ribonuclease.

According to yet further features of the described preferred embodiments the ribonuclease is substantially devoid of ribonuclease activity and has an actin binding activity.

According to a further aspect of the present invention there is provided a method of preparing a medicament useful in treating and/or preventing a disease or condition characterized by excessive cell motility comprising combining a ribonuclease of the T2 family having an actin binding activity, or a polynucleotide encoding and capable of expressing in vivo the ribonuclease of the T2 family having actin binding activity, with a pharmaceutically acceptable carrier.

According to still another aspect of the present invention, there is provided a method of preparing a medicament useful in treating and/or preventing a disease or condition characterized by abnormal accumulation of cells, the medicament to combining a ribonuclease of the T2 family having an actin binding activity, or a polynucleotide encoding and capable of expressing in vivo the ribonuclease of the T2 family, with a pharmaceutically acceptable carrier.

According to further features of the described preferred embodiments, the ribonuclease of the T2 family is a recombinant protein, expressed in a heterologous expression system. The heterologous expression system can be a bacterial expression system, a yeast expression system and a higher cell expression system.

According to yet further features of the described preferred embodiments the ribonuclease of the T2 family is substantially devoid of ribonuclease activity.

According to still further features of the described preferred embodiments, the ribonuclease can be selected from the group consisting of RNase T2, RNase Rh, RNase M, RNase Trv, RNase Irp, RNase Le2, RNase Phyb, RNase LE, RNase MC, RNase CL1, RNase Bsp1, RNase RCL2, RNase Dm, RNase Oy and RNase Tp.

According to still further features of the described preferred embodiments, the ribonuclease of the T2 family is a recombinant protein, expressed in a heterologous expression system. The heterologous expression system can be a bacterial expression system, a yeast expression system and/or a higher cell expression system.

According to yet further features of the described preferred embodiments, the ribonuclease of the T2 family is substantially devoid of ribonuclease activity.

According to still further features of the described preferred embodiments, the ribonuclease of the T2 family having actin binding activity is selected from the group consisting of RNase T2, RNase Rh, RNase M, RNase Trv, RNase hp, RNase Le2, RNase Phyb, RNase LE, RNase MC, RNase CL1, RNase Bsp1, RNase RCL2, RNase Dm, RNase Oy and RNase Tp.

According to still another aspect of the present invention, there are provided methods of enhancing a treatment of a cancer, the enhancing comprising administering to a subject in need thereof, in combination with said treatment of the cancer, a ribonuclease of the T2 family having an actin binding activity, or a polynucleotide encoding and capable of expressing in vivo said ribonuclease of the T2 family. The treatments can be chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy.

The present invention successfully addresses the shortcomings of the presently known configurations by characterizing novel activities of ribonucleases of the T2 family having actin-binding activity, useful in the prevention, inhibition and reversal of in the treatment and prevention of cell motility-associated disease such as inflammatory disease, cancer, neurodegenerative disease and infectious disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
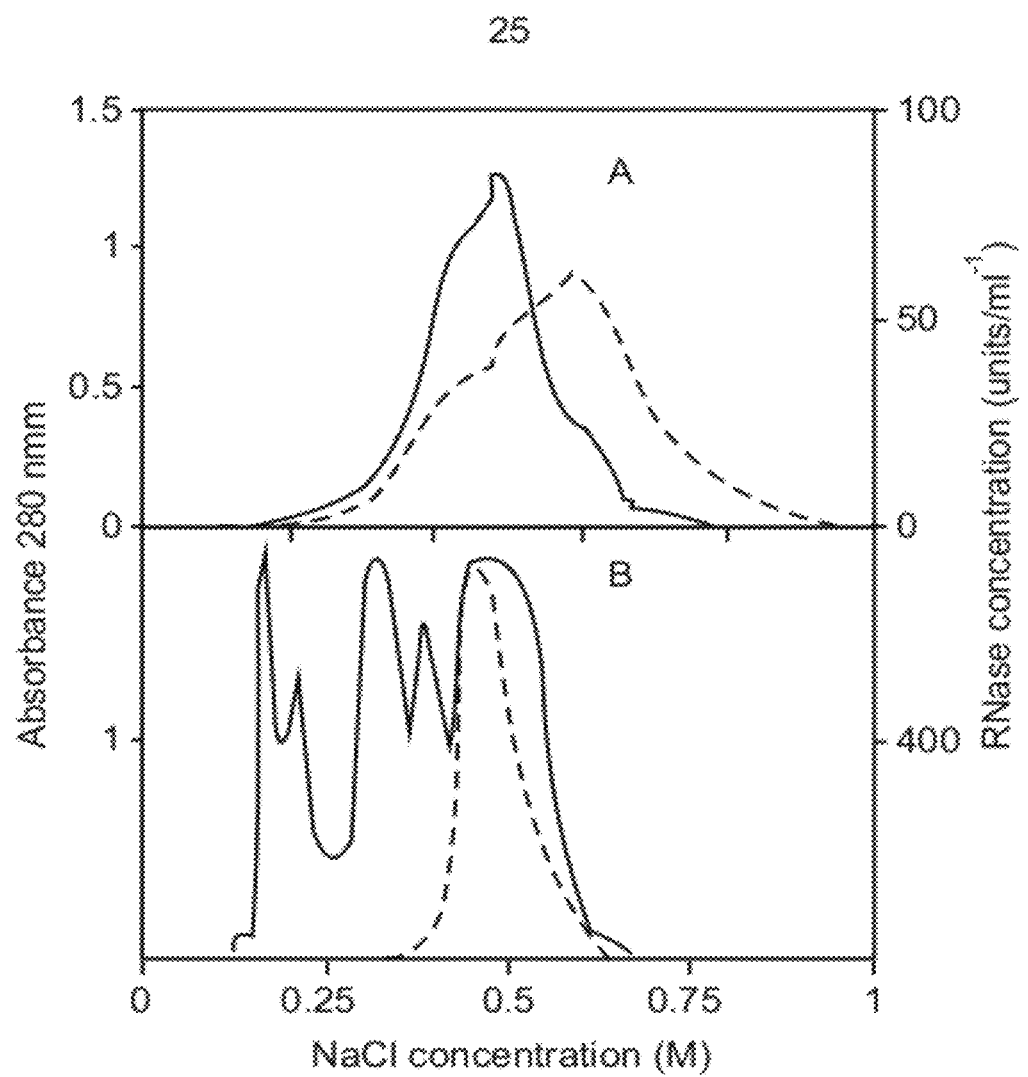

FIG. 1 is a graph representation of the absorbance and RNase activity of *Aspergillus niger* RNase B1 isolated according to the teachings of Roiz, L. and Shoseyov, O., 1995, Int. J. Plant Sci. 156:37-41. Graph A represents fractions obtained via EMD-TMAE column chromatography of a crude filtrate, while graph B represents the fraction obtained from MONO-Q column chromatography of the active fractions resulted from the EMD-TMAE chromatography of the crude filtrate. The solid line represents absorbance at 280 nm and the dashed line represents RNase activity.

Figure 2:
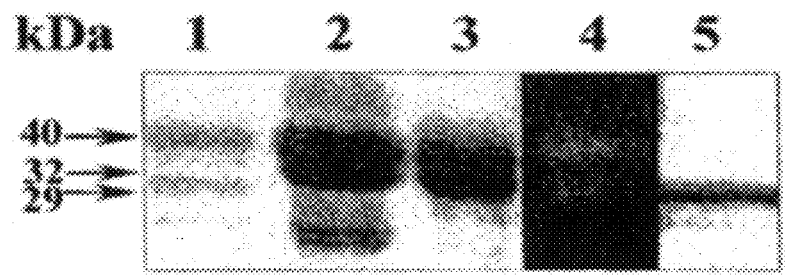

FIG. 2 is an SDS-PAGE zymogram illustrating the increase in RNase B1 protein concentration throughout the purification steps employed. Lane 1 represents the crude filtrate; lane 2 represents the eluate from the EMD-TMAE column; lane 3 represents the eluate from the MONO-Q column; lane 4 represent the eluate of lane 3 assayed in situ for RNase activity and stained with toluidine blue; lane 5 represents the purified RNase following deglycosilation by PNGase F. Lanes 1-3 and 5 are stained with coomassie blue.

Figure 3:
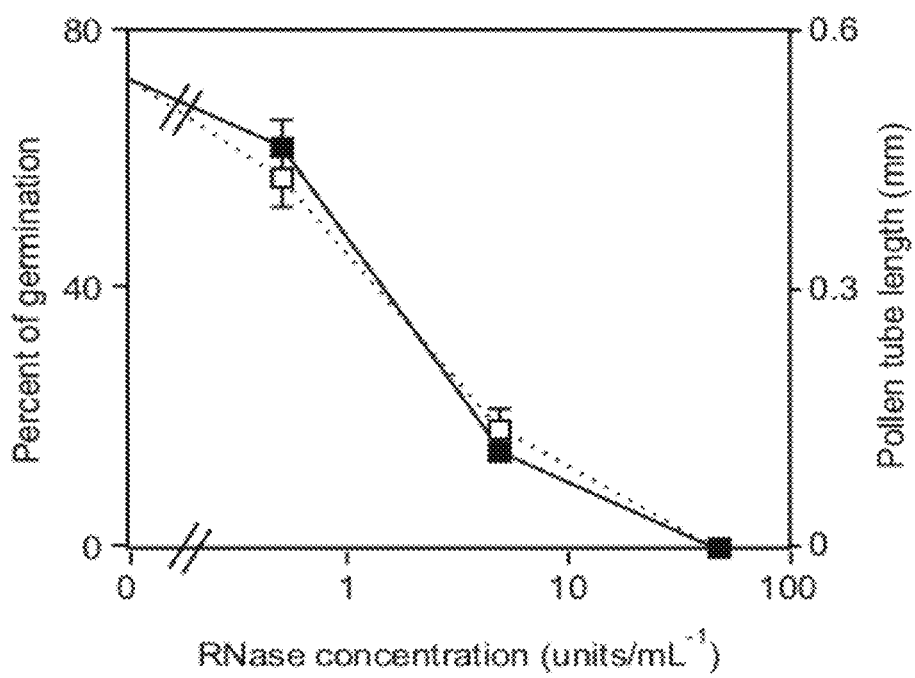

FIG. 3 is a graph illustrating the in vitro effect of different concentrations of B1 RNase on peach pollen germination (solid line with black squares) and pollen tube length (dashed line with boxes).

Figure 4A:
Figure 4B:
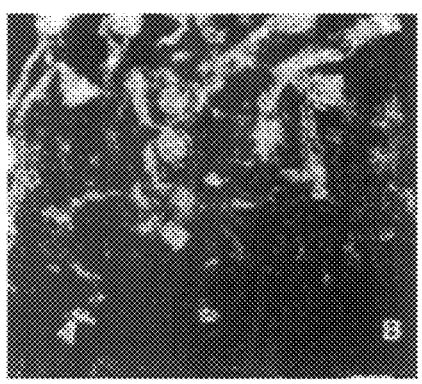
Figure 5A:
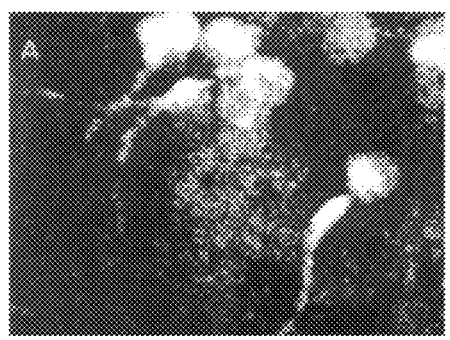
Figure 5B:
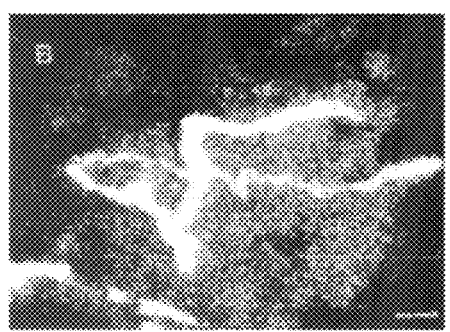

FIGS. 4a and 4b illustrate the effect of RNase B1 on peach pollen tube growth in the stigma and the upper part of the style. FIG. 4a represents the control flower, while FIG. 4b is a flower treated with RNase B1 before pollination. Bar=0.2 mm FIGS. 5a and 5b illustrate the effect of RNase B1 on pollen tube growth in the stigma of a tangerine flower. FIG. 5a represents a control flower which was exposed to open pollination for 48 hours. FIG. 5b represents a flower which was treated with RNase B1 prior to pollination. Bar=0.1 mm.

Figure 6A:
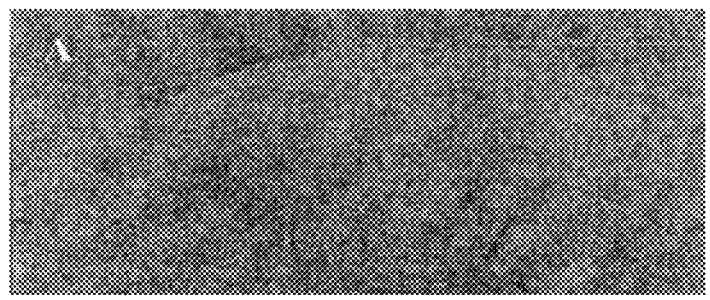
Figure 6B:
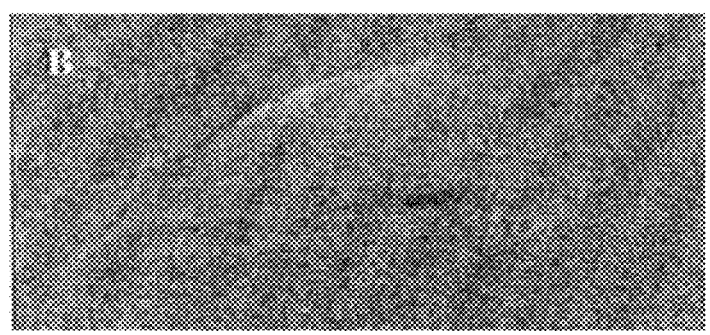

FIGS. 6a and 6b illustrate viability test conducted on nectarine seeds. FIG. 6a represents a control seed produced by an untreated flower, while FIG. 6b represents a seed produced by an RNase B1 treated flower. Bar=0.3 mm.

Figure 7:
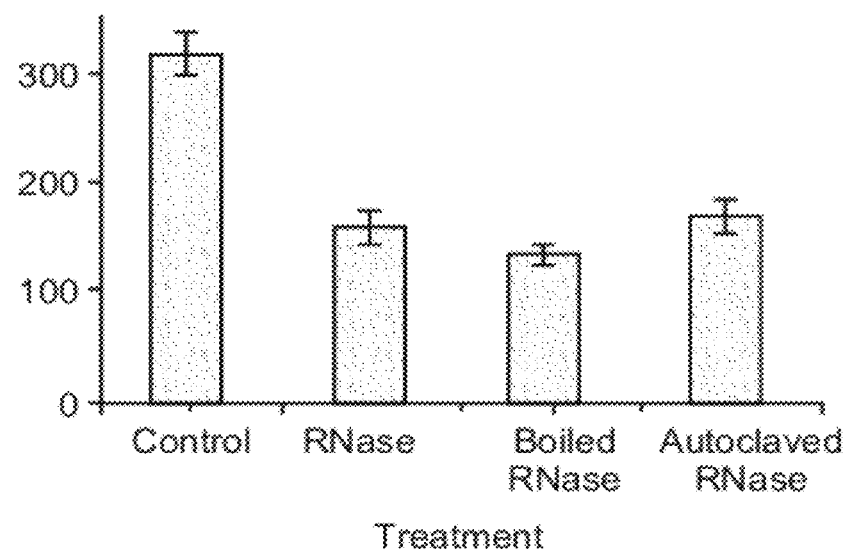

FIG. 7 illustrates the effect of RNase B1, untreated, boiled or autoclaved, on lily cv. Osnat pollen tube length.

FIGS. 8a and 8b illustrate the effect of RNase B1 on lily pollen tubes growing in vitro and stained with IKI.

FIGS. 9a and 9b illustrate still shots captured from integrated video images showing organelle movement and localization in RNase B1 untreated (FIG. 9a) and treated (FIG. 9b) pollen tubes.

FIGS. 10a and 10b illustrate the effect of RNase B1 on actin filaments of a growing lily pollen tube. FIG. 10a represents the control pollen tube whereas FIG. 10b represents the RNase B1 treated pollen tube. Both pollen tubes were excised and stained with TRITC phalloidine for visualization following experimentation.

FIG. 11 is a Scatchard plot representing RNase B1 binding to actin. A-actin concentration (μM), Rf-free RNase B1 concentration (μM), Rb-bound RNase B1 concentration (μM).

Figures 12A, 12B, 12C:
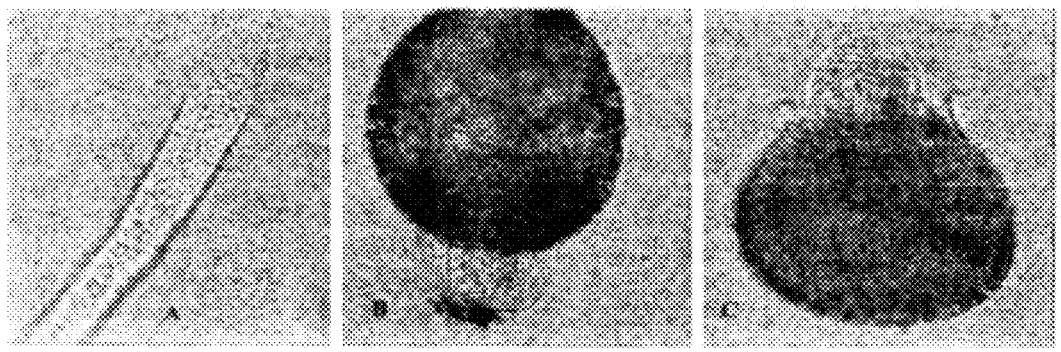

FIGS. 12a-c illustrate immunogold silver stained lily pollen tubes grown for 1 hour. FIG. 12a represents a control, whereas FIGS. 12b and 12c are both RNase to B1 treated pollen tubes. The pollen tube of FIG. 12b was incubated with rabbit pre-immune serum, while the pollen tube of FIG. 12c was incubated with anti-RNase B1 rabbit polyclonal antibody.

Figure 13A:
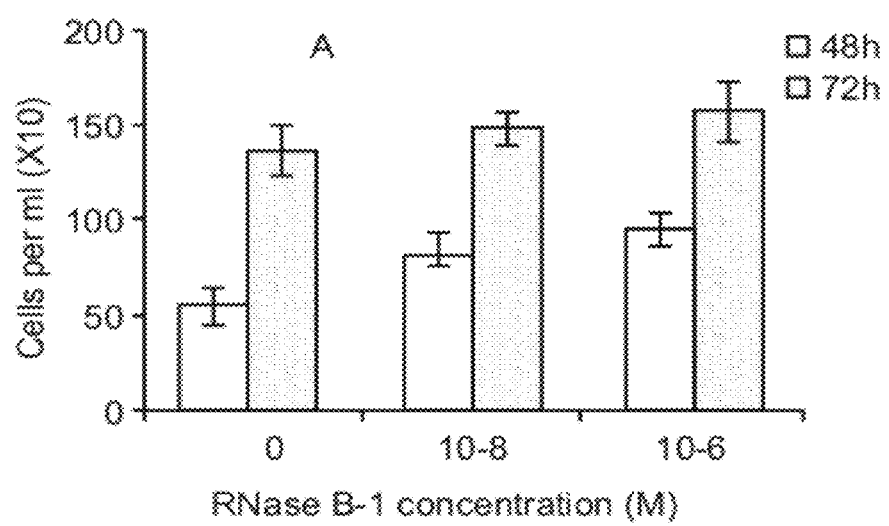
Figure 13B:
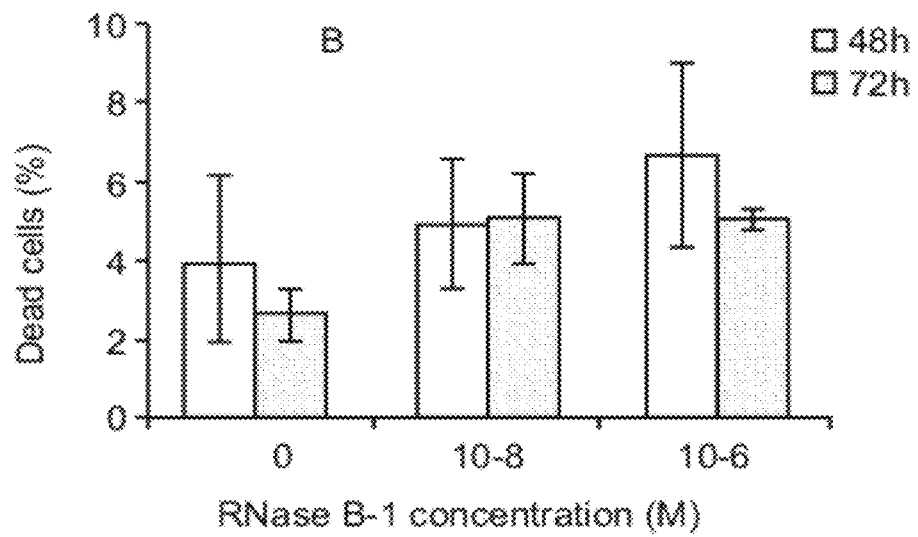

FIGS. 13a and 13b illustrate the effect of different concentrations of RNase B1 on the viability of HT29 colon cancer cells. Replicate samples of cells were grown for 48 hours or for 72 hours at 37° C., visualized using trypan blue differential staining and counted. FIG. 13a represents the total numbers of cells whereas FIG. 13b represents the percent of dead cells.

Figure 14:
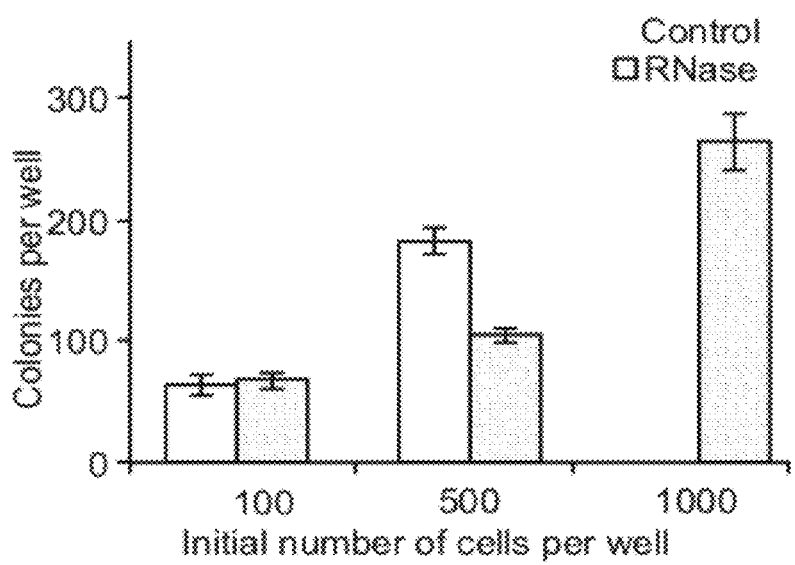

FIG. 14 illustrates the effect of RNase B1 on clonogenicity of HT29 cells. Replicate samples of cells were preincubated with growth medium in the absence or presence of $10^{-6}$ M RNase B1 for 48 hours, trypsinized, washed, resuspended in RNase B1-free growth medium in serial dilutions, and plated into 96-well microtiter plates to colonize for 14 days. Colonies were counted following fixation and staining with methylene blue.

Figure 15:
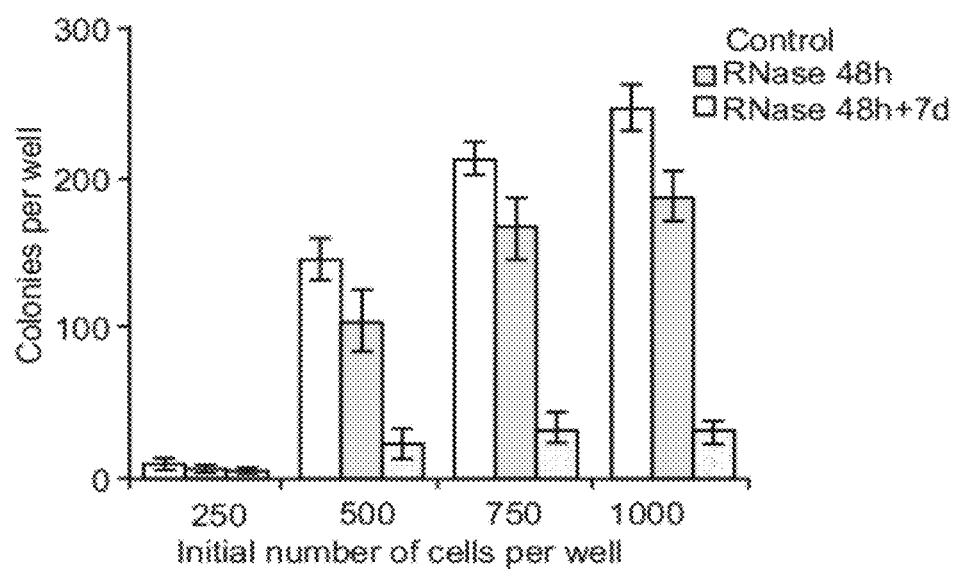

FIG. 15 illustrates the effect of exposure period to RNase B1 on the clonogenicity of HT29 cells. Replicate samples of cells were preincubated with growth medium containing $10^{-6}$ M RNase B1 for 48 hours and than let to colonize in growth medium containing the same concentration of RNase B1, or in RNase B1-free medium. Colonization was done in 96-well microtiter plates for 7 days. Each treatment contained different initial numbers of cells per well. The colonies were counted following fixation and visualization in methylene blue. Cells preincubated and colonized in RNase B1-free growth medium served as a control.

Figures 16A, 16B, 16C:
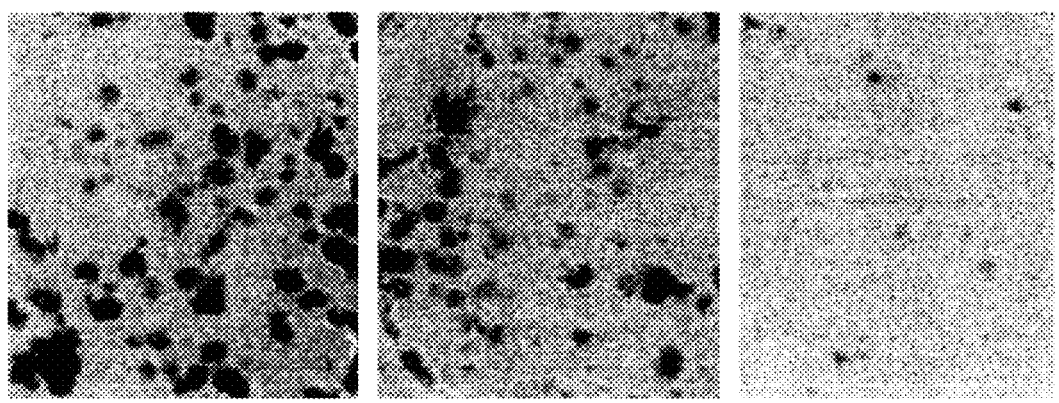

FIGS. 16a-c illustrate the effect of RNase B1 on the colonization ability of HT29 cells. Control cells (FIG. 16a) were preincubated 48 hours in RNase B1-free growth medium and then trypsinized and incubated with the same growth medium in 96-microtiter plates for colonization. FIG. 16b represents cells that were preincubated for 48 hours in growth medium containing $10^{-6}$ M RNase B1 and then allowed to colonize in RNase B1-free growth medium. FIG. 16c represents cells that were preincubated and then colonized in growth medium containing $10^{-6}$ M RNase B1. The cell colonies were visualized using methylene blue staining.

Figure 17:
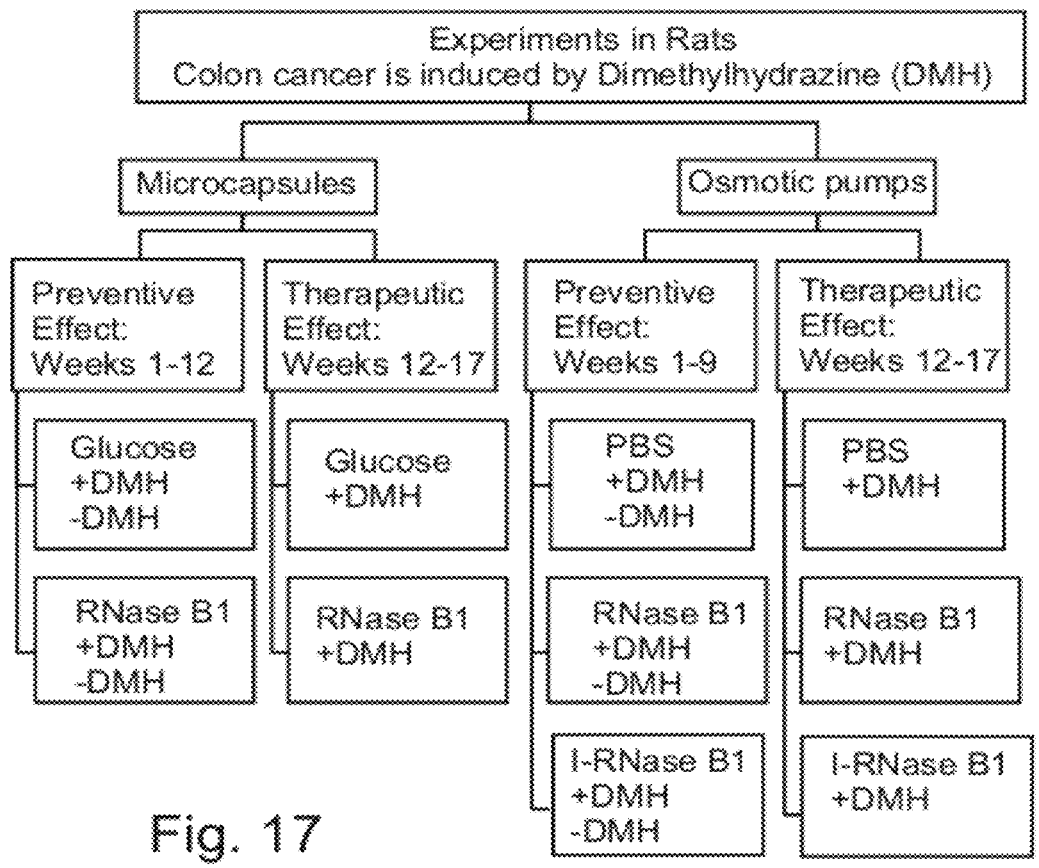

FIG. 17 is a scheme of in vivo experiments conducted in rats, describing the treatment for each group of 6 rats.

Figure 18:
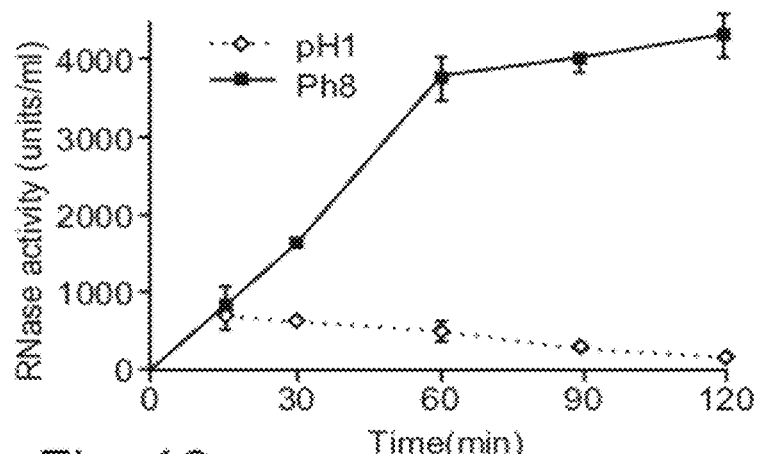
Figure 19A:
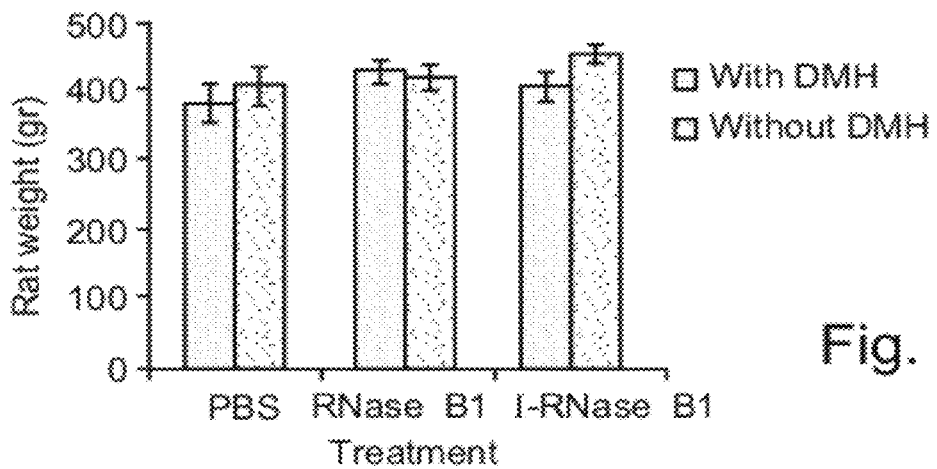
Figure 19B:
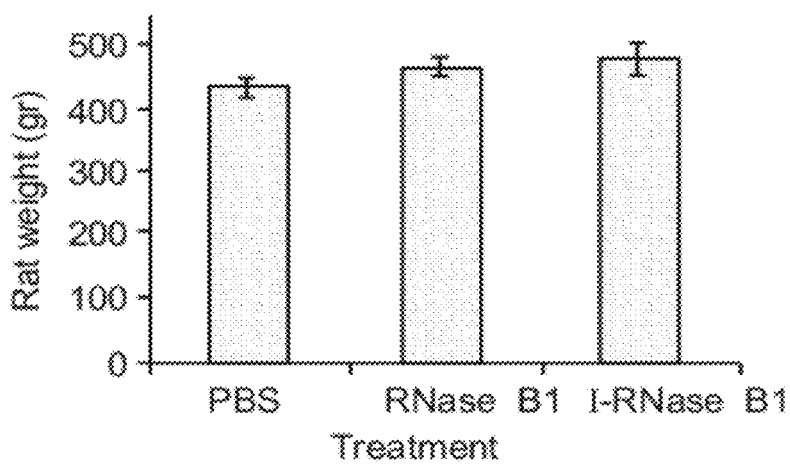
Figure 19C:
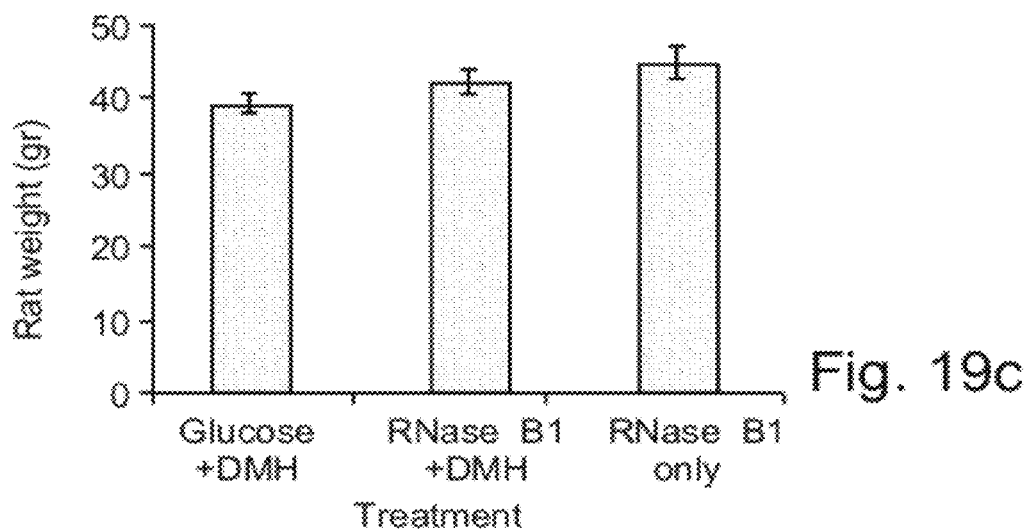
Figure 19D:
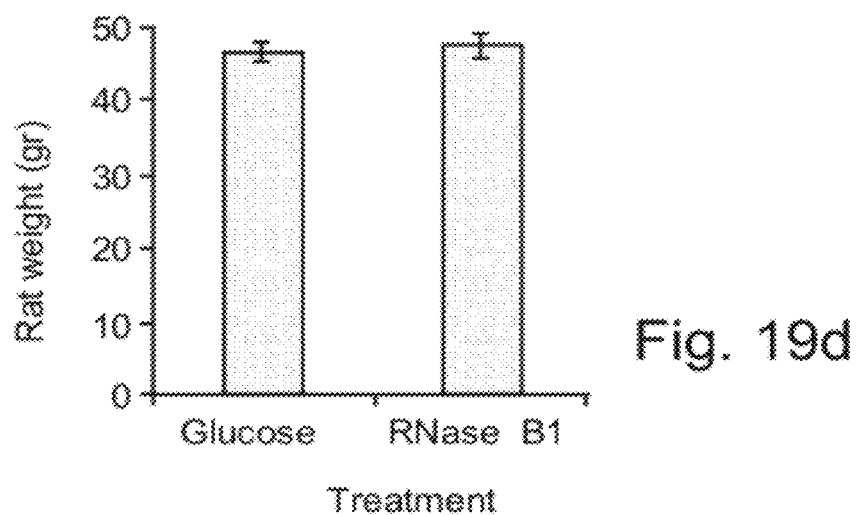

FIG. 18 demonstrates the effect of two different pHs on the rate of RNase B1 release from CAP microcapsules. Microcapsules containing 10 mg RNase B1 were suspended in 10 ml of 0.1 M HCl (pH 1) or 0.1 M Tris buffer (pH 8) and incubated at 37° C. while stirring. Samples of upper solution were taken every 30 min for RNase activity tests.

FIGS. 19a-d demonstrate the effect of RNase B1 and/or DMH on rats growth rate, as shown by body weigh at the end of each experiment. Initial rat weight was about 200 grams. n=6. 19a—PBS, RNase B1 or I-RNase B1 was given via osmotic pumps at weeks 1-9 after first DMH injection (preventive treatment). As control rats treated as described above, but in the absence of DMH were used. 19b—PBS, RNase B1 or I-RNase B1 was given via osmotic pumps at weeks 12-17 after first DMH injection (therapeutic treatments). 19c—The rats were fed with microcapsules containing RNase B1 or glucose as a preventive treatment. As control rats that were treated with RNase B1 in the absence of DMH were used. 19d—Rats were fed with microcapsules containing RNase B1 or glucose.

Figure 20A:
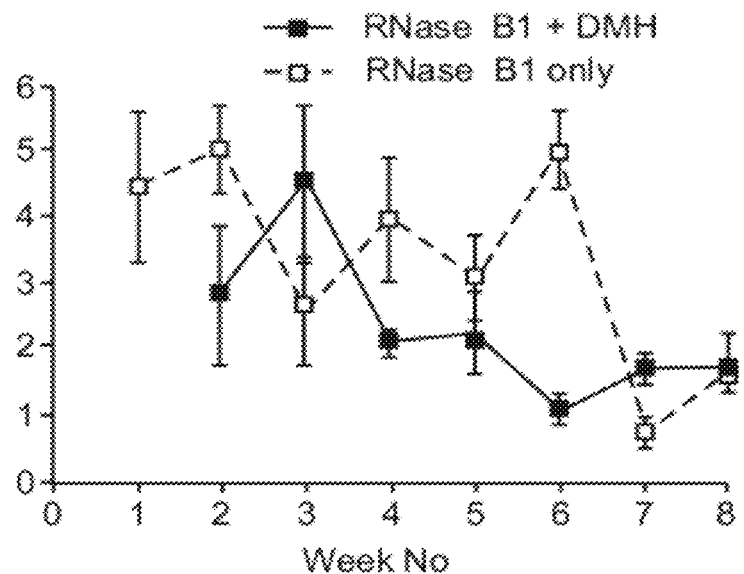
Figure 20B:
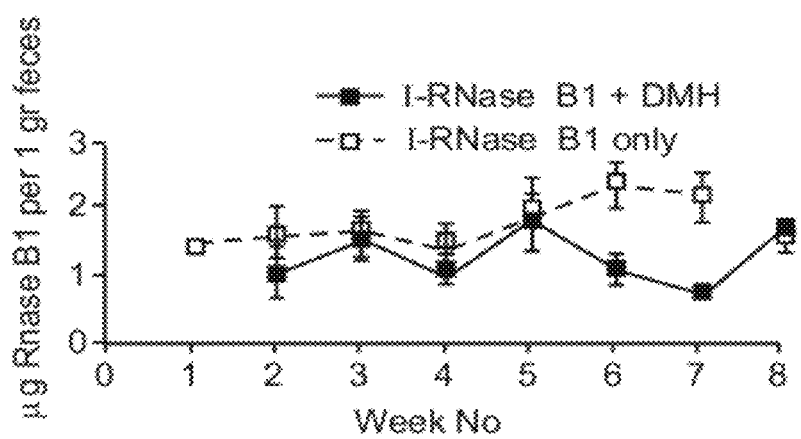
Figure 20C:
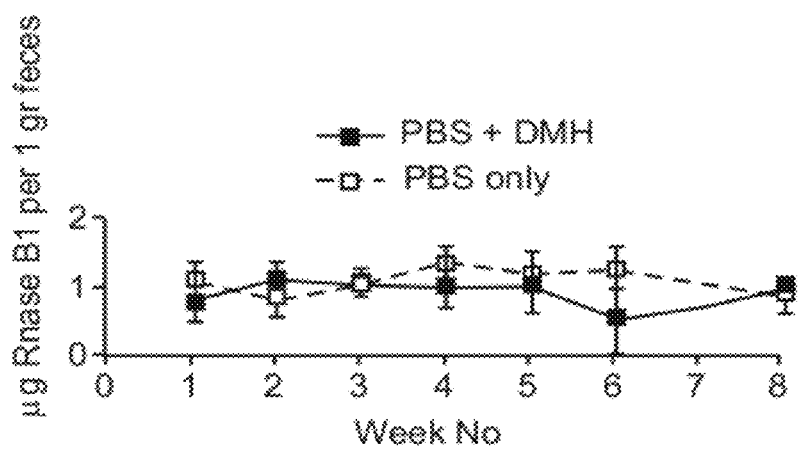

FIGS. 20a-c demonstrate RNase activity in feces of rats implanted with osmotic pumps containing RNase B1 (20a), I-RNase B1 (20b) or PBS (20c), as a preventive treatment. As control, rats were treated with RNase B1 or PBS in the absence of DMH. RNase activity was determined as described in the Examples section below.

Figure 21:
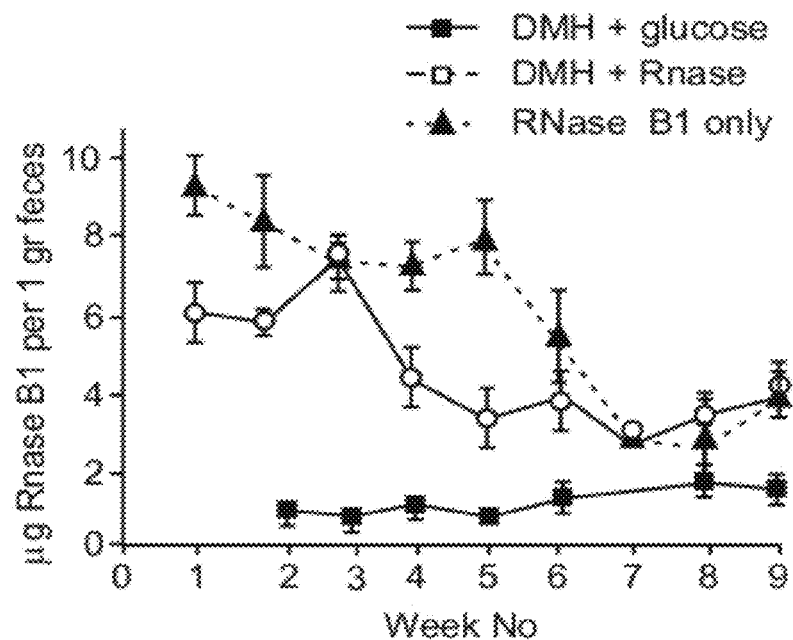

FIG. 21 demonstrates RNase activity in feces of rats fed with microcapsules containing RNase B1 or glucose as a preventive treatment. As control, rats were fed with RNase B1 or glucose in the absence of DMH. RNase activity was determined as described in the Examples section below.

Figure 22:
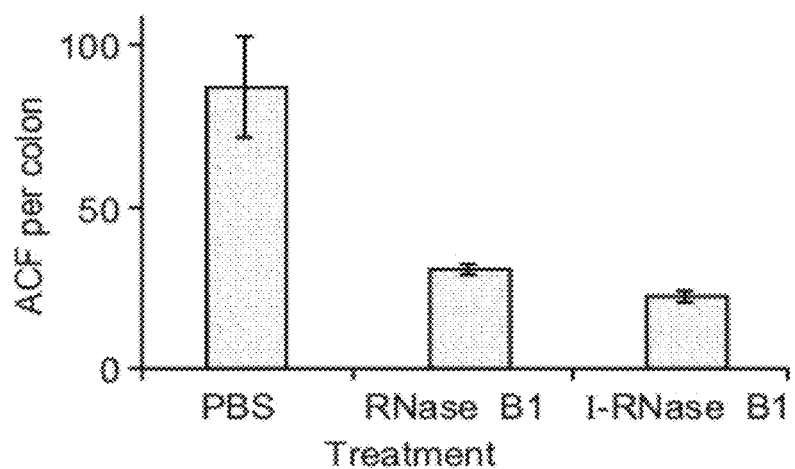

FIG. 22 show the number of aberrant crypt foci (ACF) in distal colon (5 cm) of rats implanted with osmotic pumps as a preventive treatment (n=6).

Figure 23A:
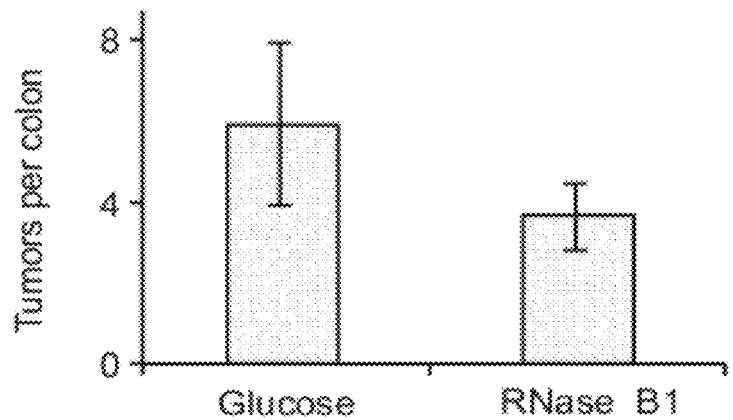
Figure 23B:
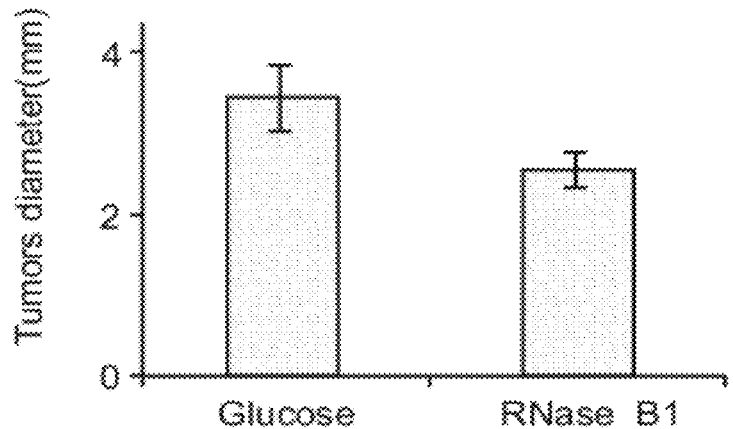
Figure 23C:
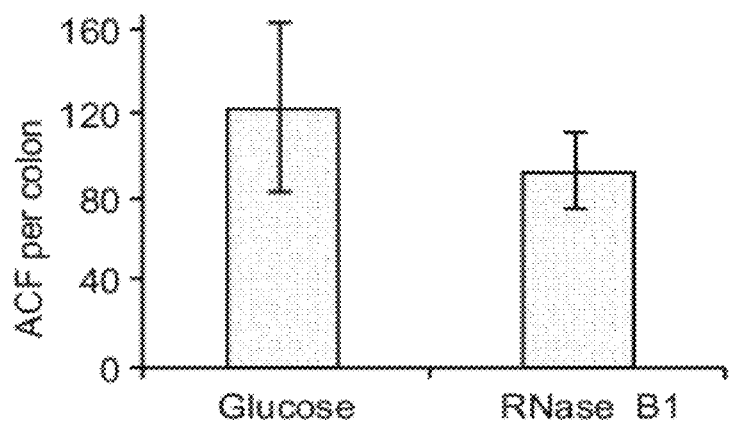

FIGS. 23a-c demonstrate the effect of RNase B1 on different parameters examined in the distal (5 cm) colon of rats fed with microencapsulated RNase B1 or glucose, as a preventive treatment (n=6). 23a—number of tumors per colon; 23b—tumor size; 23c—ACF per colon.

FIGS. 24a-d demonstrate different types of tumors, as photographed at the to inner mucosal surface 1 hour after excision. 24a—red tumors; 24b—white tumors. 24c—a pink tumor and a red tumor; 24d—distribution of three types of tumors in rats fed with microcapsules containing glucose or RNase B1, as a preventive treatment.

FIGS. 25a-d show histopathological examination of tumors stained with Mayer's heamatoxylin and martius-yellow. 25a—an adenoma or adenopapilloma—a benign tumor; 25b—adenocarcinoma, in which mucosal cells penetrated beneath the sub-mucosa; 25c—a well-developed adenocarcinoma, in which tissue arrangement is entirely interrupted; 25d—distribution pattern of adenoma and adenocarcinoma types of tumors in colons of rat treated with encapsulated glucose or RNase B1, as a preventive treatment.

Figure 26A:
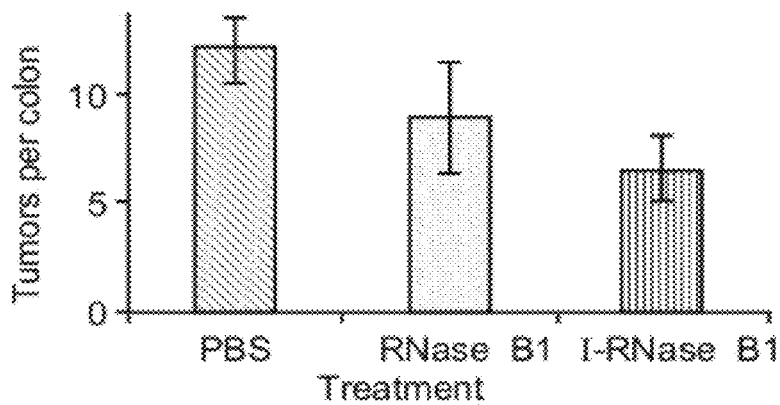
Figure 26B:
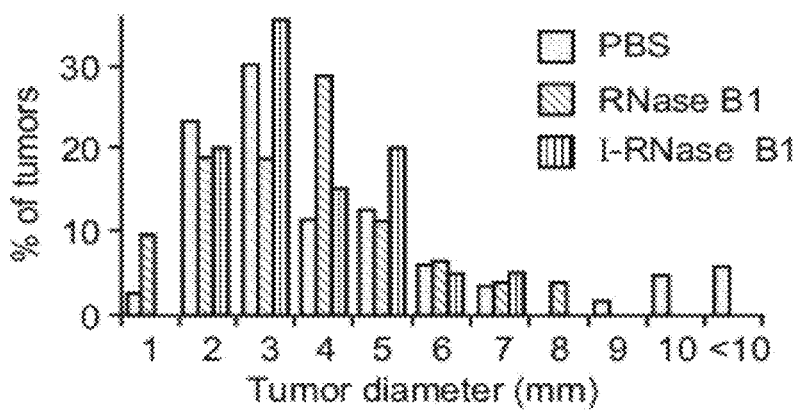
Figure 26C:
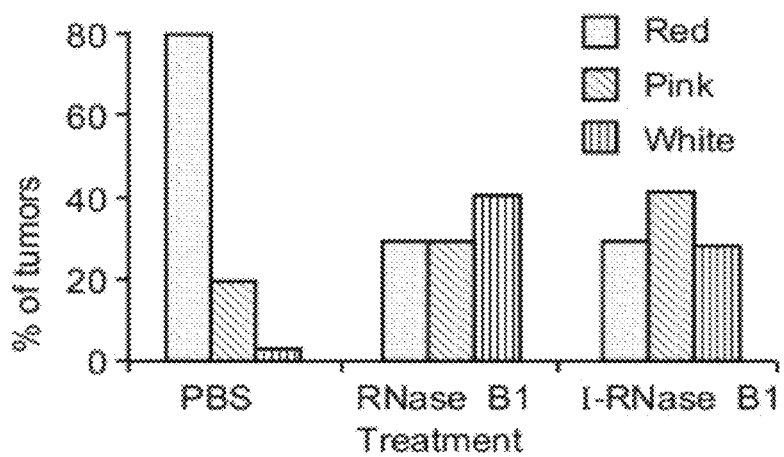

FIGS. 26a-c demonstrate the effect of RNase B1 on different parameters examined in the distal (5 cm) colon of rats treated with osmotic pumps containing PBS, RNase B1 or I-RNase B1 as a therapeutic treatment. 26a—number of tumors per colon; 26b—distribution of tumors according to size; 26c—distribution of tumors according to color, indicating angiogenesis.

Figure 27A:
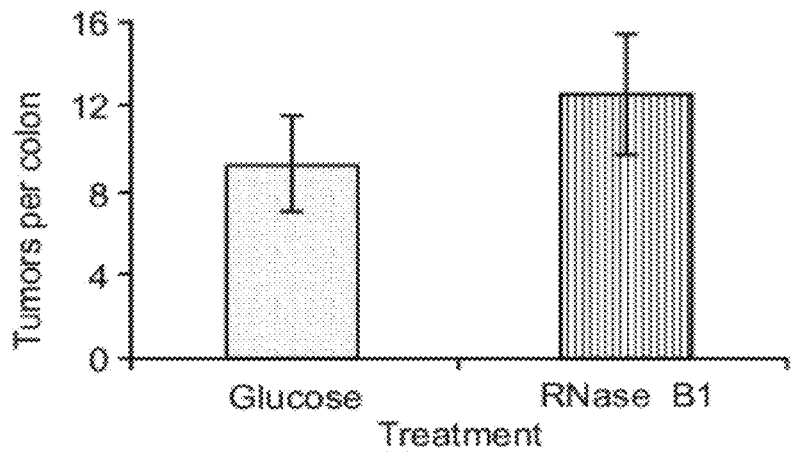
Figure 27B:
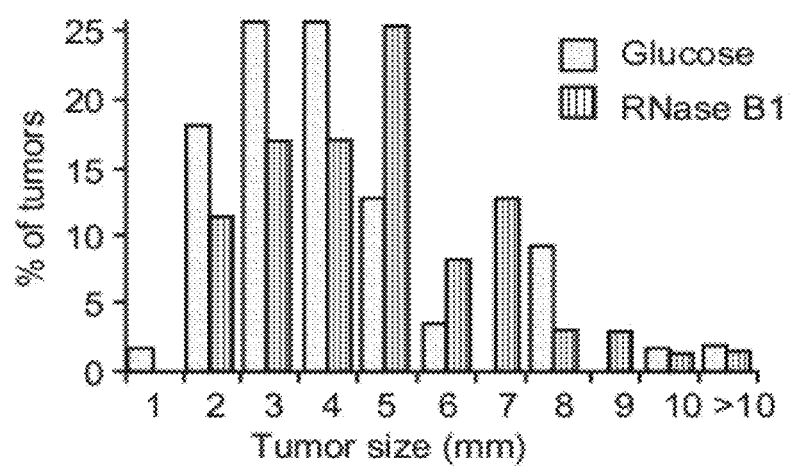
Figure 27C:
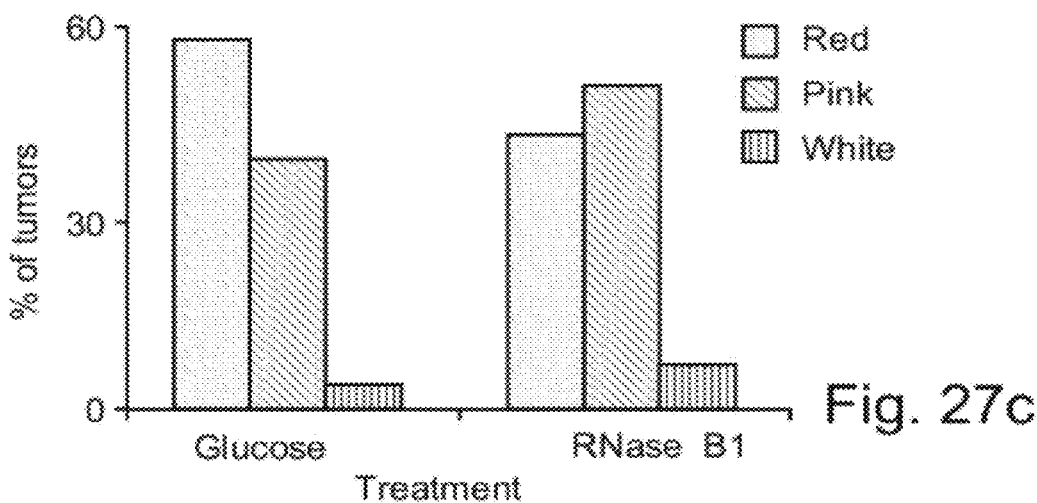

FIGS. 27a-c demonstrate the effect of RNase B1 on different parameters examined in the distal (5 cm) colon of rats fed with microencapsulated RNase B1 or glucose as therapeutic treatments. 27a—number of tumors per colon; 27b—distribution of tumors according to size; 27c—distribution of tumors according to color, indicating angiogenesis.

FIGS. 28a-b show human colon carcinoma HT-29 4-d cultured cells stained with TRIRC for actin. 28a—control cells; 28b—cells that were grown in the presence of $10^{-6}$ M RNase B1.

FIGS. 29a-b show human colon carcinoma HT-29 4-d cultured cells immunostained for membranal actin. 29a—control cells; 29b—cells grown in the presence of $10^{-6}$ M RNase B1.

Figure 30A:
Figure 30B:
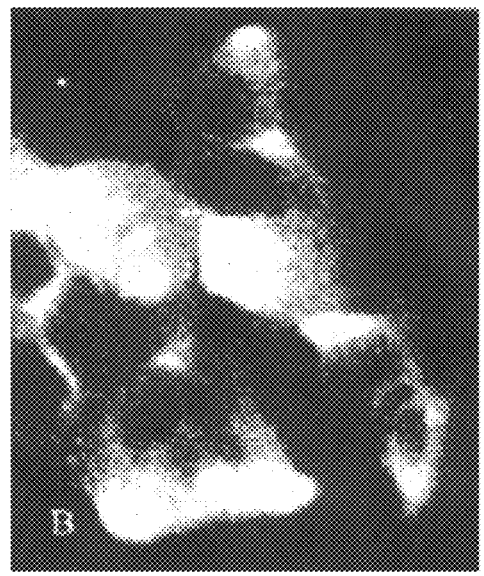
Figure 30C:
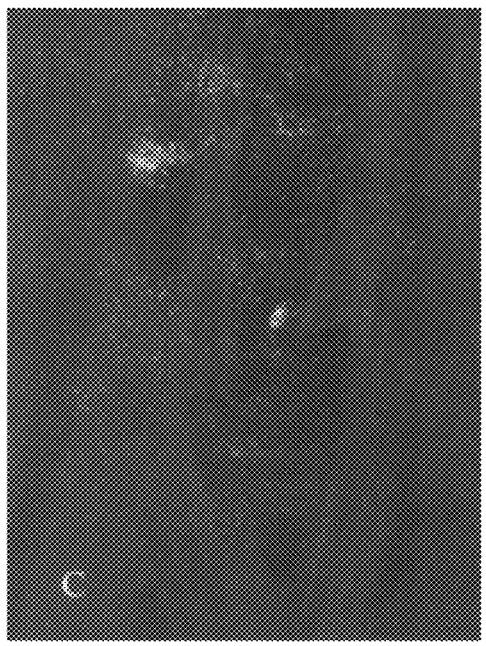

FIGS. 30a-c show human colon carcinoma HT-29 4-d cultured cells immunostained with FITC. Anti-RNase B1 was used as the primary antibody. 30a—control cells; 30b—cell that were grown in the presence of RNase B1, showing RNase B1 bound on the cell surface; 30c—pre immuned serum (PIS) was used as primary antibody.

Figure 31:
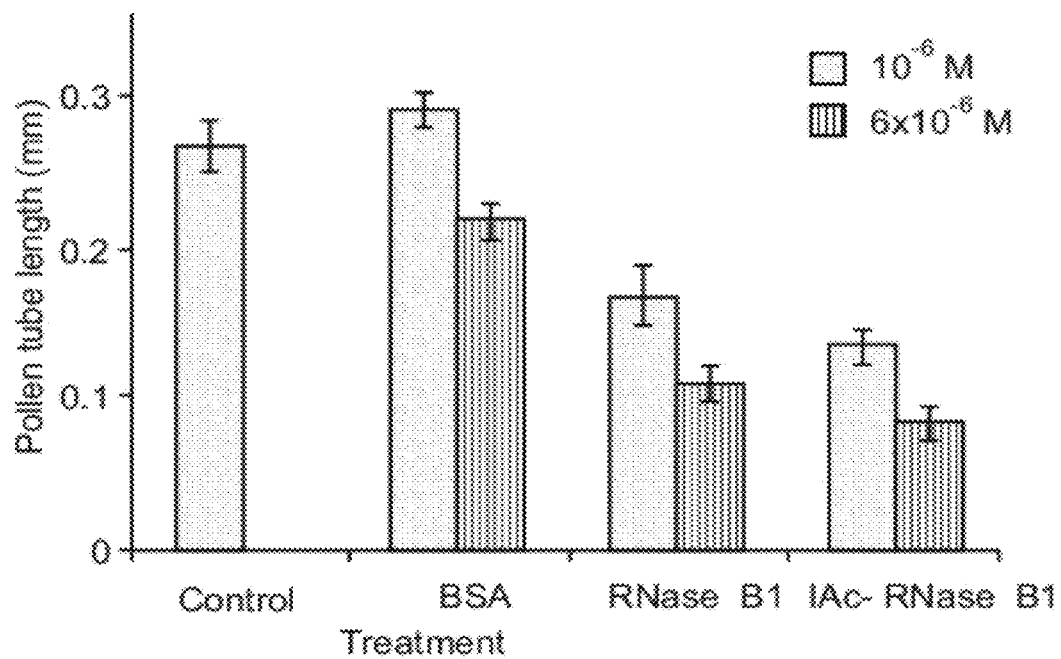

FIG. 31 demonstrates the effect of different protein treatments on lily pollen to tube length. Pollen tubes were grown in vitro for 1 hour at 25° C. as described in the Examples section that follows.

FIGS. 32a-h are photomicrographs illustrating HUVEC tube formation on Matrigel in the presence or absence of 1 µg/ml angiogenin, and in the presence or absence of RNases (2 µM each). FIG. 32a—Absence of angiogenin and RNase (Control); FIG. 32b—Angiogenin (Positive Control); FIG. 32c—RNase B1 (Negative Control); FIG. 32d—RNase B1+angiogenin; FIG. 32e—RNase T2 (Negative Control); FIG. 32f—RNase T2+angiogenin; FIG. 32g—RNase I (Negative Control); FIG. 32h—RNase I+angiogenin Note the superior inhibition of endothelial tube formation by *Aspergillus niger* RNase B1 (FIG. 32d), as compared to *Aspergillus oryzae* T2 RNase (FIG. 32f).

FIGS. 33a-d are photographs illustrating the effect of RNase B1 on B16F1 melanoma in an ip/ip experiment in BDF1 (black) and Balb/c (white) mice. Mice were intraperitoneally (i.p.) injected with $2\times10^6$ B16F1 melanoma cells and following 24 hours and 5 days the mice were further i.p. injected with either RNase B1 (5 mg/mouse in 100 μl PBS) or PBS. The presence of tumors was evaluated 14 days following melanoma cell injection. FIG. 33a—Balb/c injected with melanoma cells only; FIG. 33b—Balb/c injected with melanoma cells and RNase B1; FIG. 33c—BDF1 injected with melanoma cells only; FIG. 33d—BDF1 injected with melanoma cells and RNase B1. Note the highly developed typical black tumors in the melanoma mouse models (FIGS. 33a and c, arrows), compared with considerably smaller tumors in RNase B1-treated mice (FIGS. 33b and d, arrows).

Figures 34A, 34B:
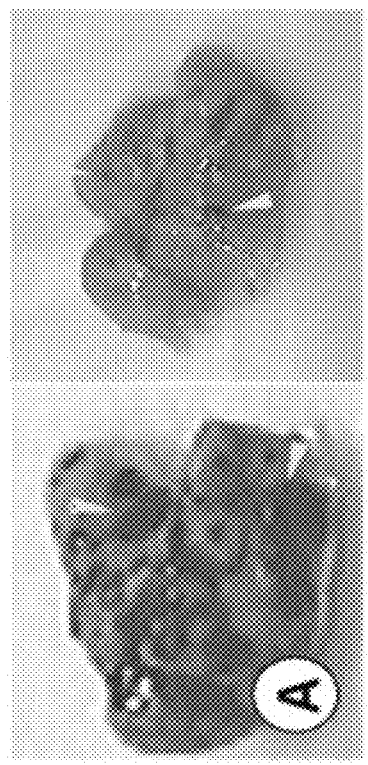

FIGS. 34a-e illustrate the effect of RNase B1 in reducing the development of B16F10 melanoma foci formed in the lungs of balb/c mice, implanted with $5\times10^5$ (FIGS. 34a-c) or $5\times10^6$ (FIGS. 34d-e) cells/mouse. FIGS. 34a-b are photomicrographs of the lungs of the B16F10-implanted mice following RNase B1 (10 mg/mouse, three times, every four days, starting 24 hours after cells injection) or PBS treatment. FIG. 34a—PBS; FIG. 34b—RNase B1. Note the significant decrease in melanoma foci and metastases following RNase B1 treatment (FIG. 34b, arrows) as compared to PBS injection (FIG. 34a, arrows). FIGS. 34c-e are graphs depicting a quantitative determination of the number of metastases per lung (FIG. 34c), the lung weight (FIG. 34d) and the mean metastasis diameter (FIG. 34e). Note the significant decrease in the number of metastases/lung (76%, $P<0.001$, FIG. 34c), the average lung weight (25%, $P<0.01$, FIG. 34d), and the mean metastasis diameter (25%, $P<0.001$, FIG. 34e) in the RNase B1-treated mice as compared with PBS injected mice.

Figure 35:
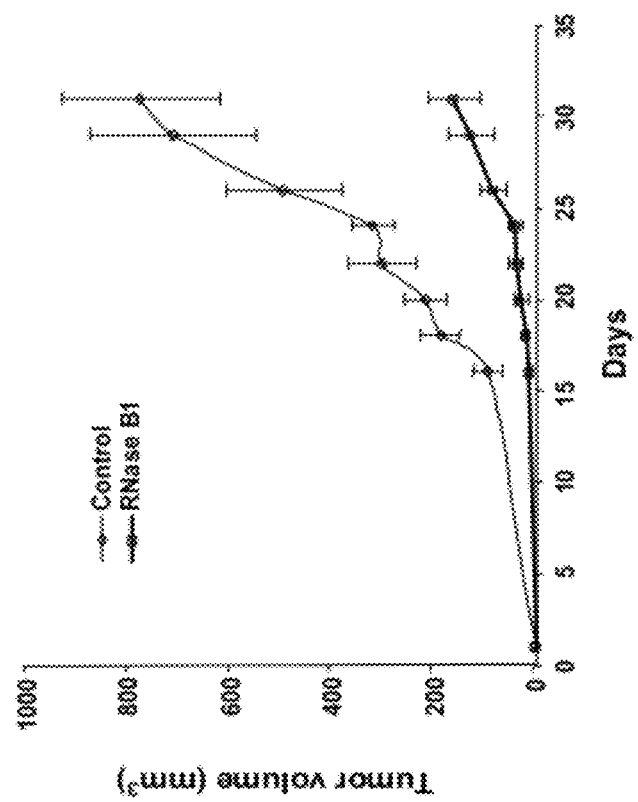

FIG. 35 illustrates the effect of RNase B1 on tumor growth of human melanoma cells in nude mice. A375SM melanoma cells ($5\times10^5$) were injected subcutaneously into nude mice (n=5) and three days later, animals injected with the tumor cells were subsequently intraperitoneally injected with either 1 mg of RNase B1/mice or PBS (control) Animals were injected for 30 days (every other day, 3 days a week) and the tumor dimensions were recorded at the noted times. Shown are tumor volumes as expressed in $mm^3$ as calculated from the equation of (length×width)/2. Note that while in mice injected with PBS the tumor volume drastically increased and reached the size of 800 $mm^3$ within 30 day, in RNase B1-treated mice the tumor volume remained relatively low and did not exceed 180 $mm^3$ at thirty days-post melanoma cells injections.

Figure 36A:
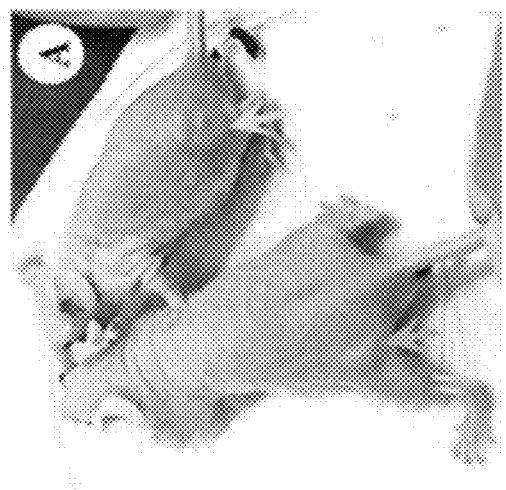
Figure 36B:
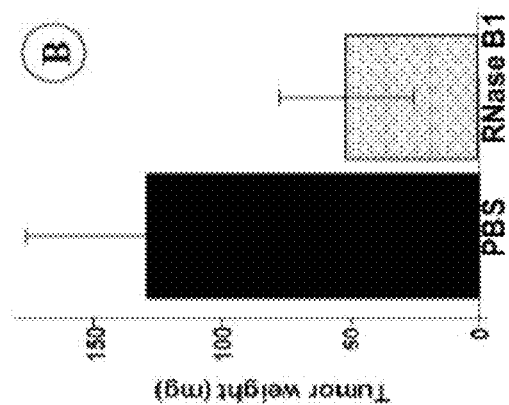

FIGS. 36a-b illustrate the effect of RNase B1 on tumor size in HT-29 derived nude mice xenografts in an s.c./i.v. experiment. Tumors were induced in mice using HT-29 cells ($3\times10^6$ per mouse) and the mice were further subjected to RNase B1 (2 injections containing 5 mg RNase B1 each in 100 μl PBS) or PBS (control) injections. FIG. 36a—an overall view of tumors in PBS (control, yellow arrow) or RNase B1 (blue arrow)-treated. Note the significant decrease in the size of tumor in the RNase B1-treated mice (blue arrow) as compared with the PBS injected mice (yellow arrow); FIG. 36b—is a bar graph depicting tumor size in PBS or RNase B1-treated mice (n=5). Note the average 60% decrease in tumor size following RNase B1 treatment.

FIG. 37 is a photograph illustrating in vivo inhibition of angiogenesis by RNase B1. Gel foams impregnated with 100 ng/sponge angiogenin were subcutaneously implanted in both sides of a nude mouse and following 48 hours the mice were intraperitoneally injected at both sides of the peritoneaum (7 times, every two days), each with a different treatment; one side with RNase B1 (250 μM RNase B1 in 100 μl) and the other side with PBS. Note the significant angiogenesis in the side of PBS injection (circled region with an arrow, Angiogenin) as compared with the negligible angiogenesis in the side of RNase B1 injection (circled region with an arrow, Angiogenin and RNase B1), indicating RNase B1-mediated inhibition of the angiogenin-induced development of blood vessels.

Figure 38:
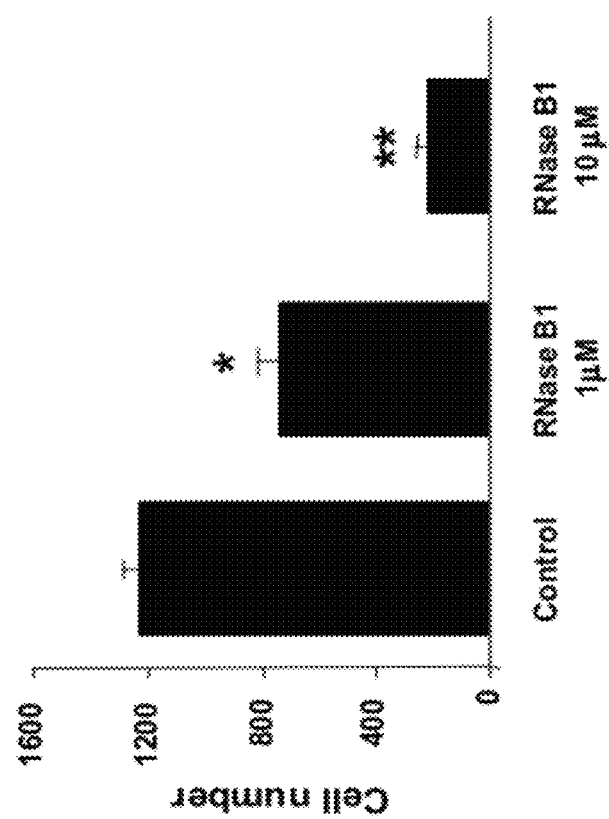

FIG. 38 is a bar graph illustrating the effect of RNase B1 in inhibiting A375SM cell invasion. A375SM cells were treated in the presence or absence of RNase B1 and following 22 hours the number of cells invaded the Matrigel-coated filter were counted. Note the dose-dependent effect of RNase B1 in inhibiting A375SM invasion to the Matrigel-coated filter. While in untreated A375SM cells (control) 1216±68 cells penetrated the Matrigel-coated filters, 725±59 or 211±14 A375SM cells which were treated with 1 or 10 μM RNase B1 penetrated the Matrigel-coated filters. *=$P<0.01$; **=$P<0.001$.

Figure 39B:
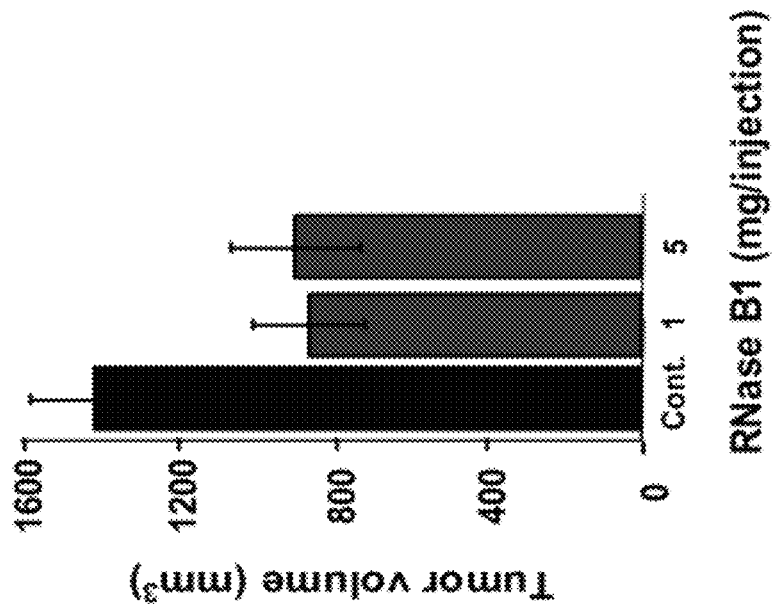
Figure 39A:
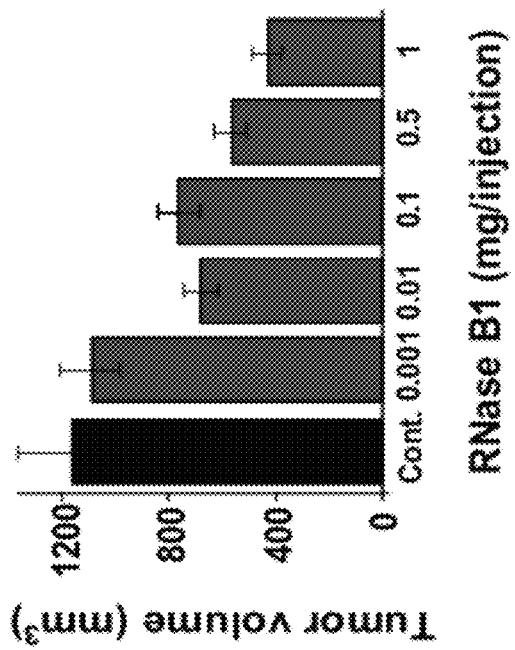

FIGS. 39a-b are bar graphs illustrating HT-29-derived nude mice xenografts in the sc/ip model. RNase B1 was injected at the noted concentrations starting from 24 hours following cells implantation ($10^6$ cell/mouse) and every other day. Tumor size was measured 30 days following the onset of RNase B1 treatment. Note the significant reduction (up to 60%) in tumor size following RNase B1 treatment at a wide range of doses, 0.001-1 mg/injection (FIG. 39a) and 1-5 mg/injection (FIG. 39b) in the two subsequent experiments (N=6 in each case), demonstrating the preventive (FIG. 39a) and therapuetic (FIG. 39b) effects of RNase B1 treatment. Cont.=HT-29-implanted mice which were injected with PBS.

FIGS. 40a-c are photomicrographs of peritoneum cross sections from HT-29-implanted nude mice in the s.c./i.p. model in the presence or absence of RNase B1. FIG. 40a—Hematoxylin and Eosin (H&E) staining. Note the thin peritoneum (arrow) overlaying the muscle; FIGS. 40b-c—Immunostaining of peritoneum taken from an RNase B1-treated mouse (FIG. 40b) or PBS-treated mouse (FIG. 40c), using rabbit anti-RNase B1 and FITC-conjugated goat anti rabbit. Note the green fluorescence demonstrating the accumulation of RNase B1 onto the peritoneum of the RNase B1-treated mouse but not the PBS-treated mouse.

FIGS. 41a-c are photomicrographs of cross sections from HT-29-derived tumors of the s.c./i.p nude mice model. FIG. 41a-H&E staining; FIGS. 41b-c—Immunostaining of a blood vessel of a tumor derived from an RNase B1-treated (FIG. 41b) or PBS-treated (FIG. 41c) mouse, using rabbit anti-RNase B1 and to FITC-conjugated goat anti-rabbit. Arrows indicate blood vessels. Note the accumulation of RNase B1 onto the basal membrane.

FIGS. 42a-b are representative histopathology sections of colon cancer tissue illustrating the effect of RNase B1 on CD31 expression on DMH-induced colonic tumors. Tumor sections from dimethylhydrazine (DMH)-treated rats (FIG. 42a) or from DMH and RNase B1-treated rats (FIG. 42b) were stained with an anti-CD31 antibody (sc-8306 antibody Santa Cruz Biotechnology Inc. Santa Cruz, Calif.). Note the presence of high number of large blood vessels in the tumors of DMH-treated rats (FIG. 42a) and the significantly lower size and number of blood vessels in DMH-RNase B1-treated rats (FIG. 42b). Magnification×200. Size bar=100 μm.

FIGS. 43a-b are photomicrographs of representative histopathology sections of tumors in nude mice showing the pro-apoptotic effect of RNase B1 on tumor size and apoptosis in mouse melanoma cells. Mouse B16F1-derived melanoma cells ($2 \times 10^6$ cells/mouse) were grown in the intraperitonal cavity of BDF1 and Balb/c mice. RNase B1-treated mice received two intraperitoneal injections of 5 mg RNase B1 in 100 μl PBS, 24 hours and 5 days after injection with the melanoma cells. Untreated control mice received PBS injections. After 14 days, the mice were sacrificed and samples prepared for analysis. Paraffin cross-sections were stained for apoptosis using Klenow-FragEl kit (Oncogene, Cambridge, Mass.). Note the predominance of apoptotic cell nuclei (brown stain) in the tumors from RNase B1-treated mice (FIG. 43b), as compared with the actively dividing nuclei (green stain) in the untreated controls (FIG. 43a).

FIGS. 44a-b are photomicrographs of representative colon tumor sections illustrating the effect of RNase B1 on apoptosis rate in DMH-induced colonic tumors. Sections of colon tumors from dimethylhydrazine (DMH)-treated rats were fixed and embedded in paraffin, and assayed for apoptosis by the deoxynucleotide transferase-mediated dUTP-nick end-labeling (TUNEL) assay using the Klenow-FragEl (Oncogene, Cambridge, Mass.). Apoptotic cells were stained and visualized (brown staining) with peroxidase-conjugated anti-digoxigenin antibodies. FIG. 44a—DMH-treated rat; FIG. 44b—RNase B1-DMH-treated rat. Note that while no TUNEL-positive cells are observed in tumor sections of DMH-treated rats (FIG. 44a), a large to number of TUNEL-positive (i.e., apoptotic) cells are observed in tumor sections of RNase B1-DMH-treated rat (FIG. 44b). Size bar=100 μm.

FIGS. 45a-d are representative histopathology sections of tumors in nude mice showing the pro-apoptotic effect of RNase B1 on tumor size and apoptosis in human colon cancer xenografts. HT29 cancer cells ($2.5 \times 10^6$ cells/mouse) were injected into the left hip of nude mice. RNase B1-treated mice (n=5) received 3 intravenous injections of 5 mg RNase B1 every 5 days, starting 24 hours following cancer cells injection (FIGS. 45b and d). Control mice (n=5) were left untreated (FIG. 45a and c). Paraffin sections of tumors were stained by Hematoxylin and Eosin (H&E) for histology evaluation (FIGS. 45a-b) and with Klenow-FragEl kit (Oncogene, Cambridge, Mass., FIGS. 45c-d) for apoptosis. Vital and actively dividing nuclei are stained bright green, whereas apoptotic nuclei are stained brown. Note the condensed cytoplasm and nuclei (FIG. 45b) and high proportion of apoptotic cells (FIG. 45d) in the tumors from RNase B1 treated mice, as compared with the normal vital appearance (FIG. 45a) mitotic activity (FIG. 45c) in the tumors from untreated controls.

Figure 46:
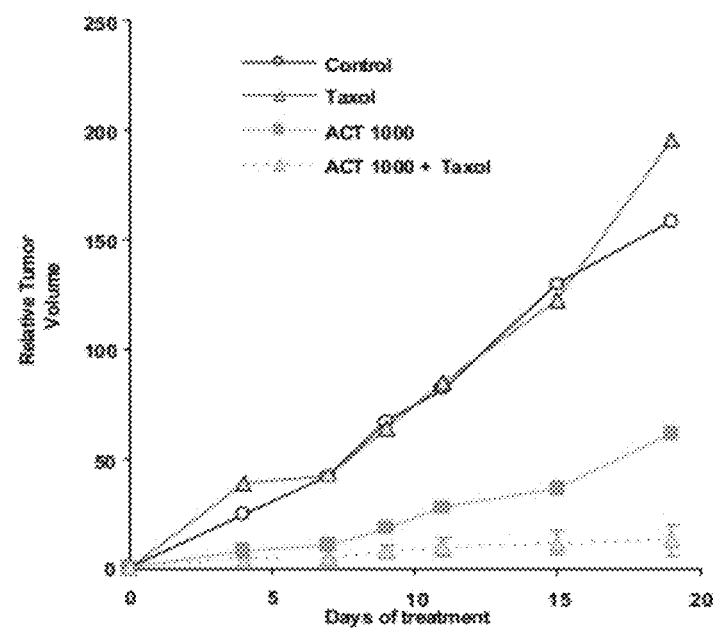

FIG. 46 is a graph illustrating the effects of Taxol and RNase B1 on relative volume of LS174T-induced tumors. Balb/c (athymic mice (CD-1 nu/nu; Charles River, Wilmington, Mass.) nude mice were s.c. injected with LS174T cancer cells and 10-13 days following cell injection (when tumors were palpable) the mice were treated with i.p. injections of the noted treatments for 5 consecutive days out of 7 days over a period of 3 weeks. Control: PBS or propylene glycol+ethanol; RNase B1: 50 mg/kg RNase B1 (1000 μg/injection); RNase B1+Taxol: 50 mg/kg RNase B1 and 5 mg/kg Taxol; Taxol: 5 mg/kg Taxol (100 μg/injection). Note the significant effect on the relative tumor volume (RTV) in the RNase B1-treated mice as compared to Taxol-treated mice, and the unpredicted significant inhibition of tumor growth in mice treated with the combined treatment of RNase B1 and Taxol.

Figure 47:
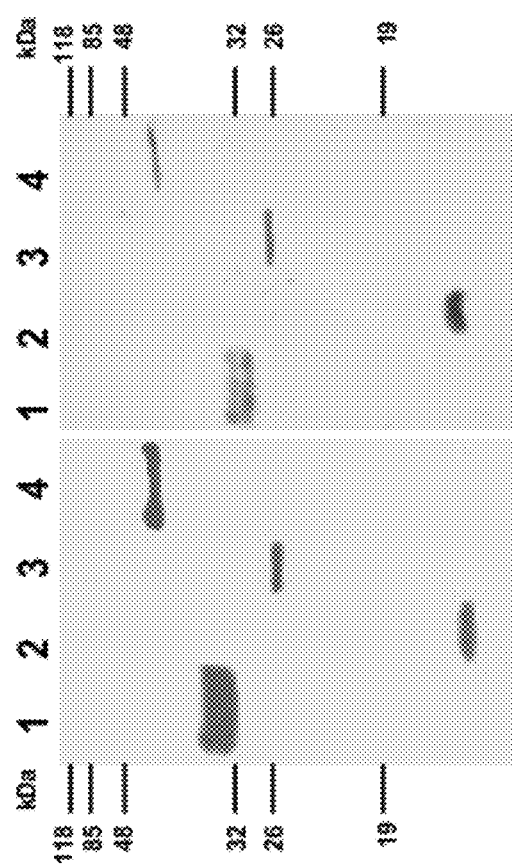

FIGS. 47a-b are Western blot (FIG. 47a) and SDS-PAGE protein staining (FIG. 47b) of actin and actin-binding proteins illustrating the ability of RNase B1 to bind actin in vitro. Actin and actin-binding proteins were run on an SDS-PAGE and transferred on a nitrocellulose membrane. The membrane was incubated with actin and then with anti-actin followed with peroxidase-conjugated goat anti mouse IgM to [Actin (Ab-1) Kit, CAT #CP01-1EA (Oncogene)]. Signals were detected using the ECL detection system (Pierce CAT No #24080). Lane 1—RNase B1, lane 2—Angiogenin, lane 3—E. coli RNase I, lane 4—actin. Note the strong band intensity in lanes 1 and 4 indicating the strong association of RNase B1 to actin.

Figure 48:
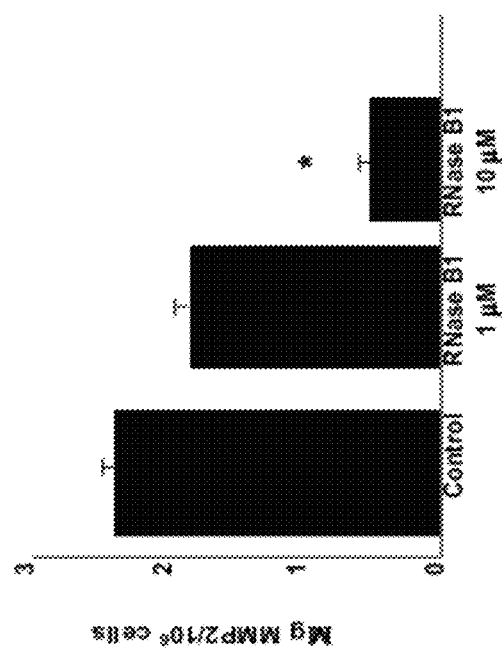

FIG. 48 is a bar graph illustrating a dose-dependent effect of RNase B1 in inhibiting total MMP-2 release by A375SM melanoma cancer cells. A375SM cells were grown in Complete Eagle's minimum essential medium (CMEM) in the presence or absence of 1 or 10 μM RNase B1 and the level of MMP-2 in the medium was measured using ELISA [Quantikine MMP-2 immunoassay kit (R&D Systems Inc., Minneapolis, Minn.)] and is expressed as mg MMP-2/$10^6$ cells. Note the maximal inhibitory effect obtained in the presence of 10 μM RNase B1.

Figure 49A:
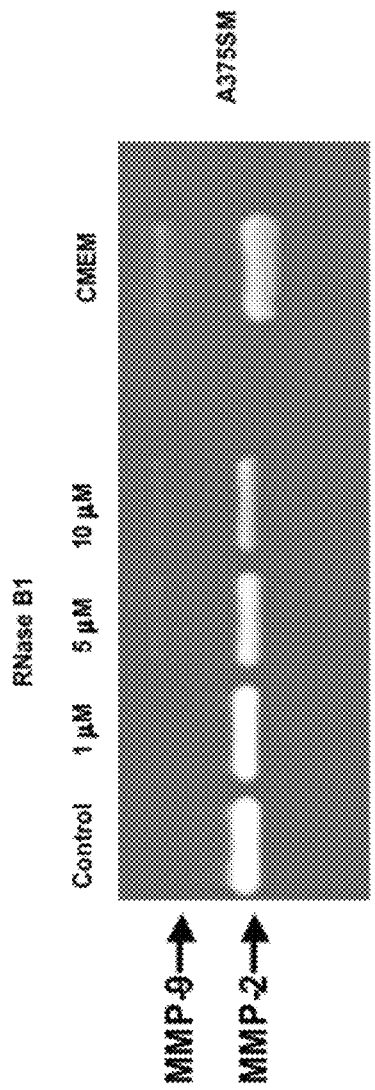
Figure 49B:
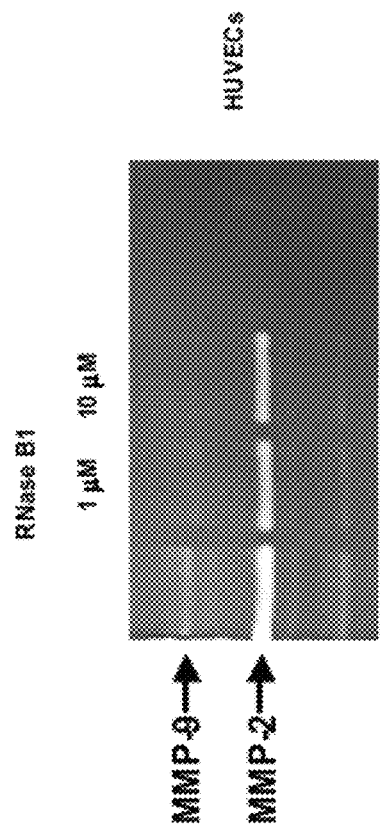

FIGS. 49a-b are zymograms of MMP-2 Collagenase activity illustrating the effect of RNase B1 treatment on MMP-2 release in A375SM (FIG. 49a) or HUVEC (FIG. 49b) cells. The supernatant of cells treated in the presence or absence of various concentrations of RNase B1 was loaded on gelatin-containing SDS gels and following electrophoresis the gels were Triton-treated and stained with Coomassie Blue. The presence of MMP-2 Collagenase activity is seen as a white band on the blue gel reflecting gelatin-degradation by the 72 kDa MMP-2 collagenase activity. Note the intense bands in A375SM cells in the absence (FIG. 49a, control) or presence of 1 μM RNase B1 and the significant decrease in band intensity following treatment of A375SM cells with 5 and 10 μM RNase B1 (FIG. 49a). Also note the dose-dependent decrease in band intensity of the 72 kDa MMP-2 in the presence of 1 and 10 μM RNase B1 in HUVECs cells (FIG. 49b), as well as the decrease in band intensity of the MMP-9 (FIG. 49b, arrow); CMEM (Complete Eagle's minimum essential medium)-media containing sera=positive control.

FIGS. 50a-s are confocal photomicrographs illustrating the cellular localization of RNase B1 in RNase B1-treated HUVEC cells. HUVEC cells were treated with 0.4 mg/ml (i.e., 10 μM) RNase B1 and following 48 hours the cells were subjected to immunostaining using the RNase B1 and CD31 antibodies. Shown are the results of serial digital foci done by the confocal microscope. All slices were done at the same time point and show different areas in the treated cells. CD31=red, RNase B1=green. Note that the RNase B1 gradually penetrates the cell membrane (as detected by to the red label of CD31 which is expressed only in the membrane of HUVEC cells) and enters into the cell.

FIGS. 51a-c are confocal photomicrographs illustrating the cellular localization of RNase B1 in RNase B1-treated A375SM cells. A375SM cells were treated with 0.4 mg/ml (i.e., 10 μM) RNase B1 and the cellular localization of the RNase B1 was detected following 2 (FIG. 51a), 4 (FIG. 51b) or 8 (FIG. 51c) hours using RNase B1 immunostaining and confocal microscopy. Note the gradual penetration of RNase B1 into the cell membrane (FIG. 51a, 2 hours), cell cytoplasm (FIG. 51b, 4 hours) and cell nuclei (FIG. 51c, 8 hours). Also note the RNase B1-induced rounding of the cells following 4 hours (FIG. 51b) and the apoptotic characteristics of the A375SM melanoma cells following 8 hours (FIG. 51c).

FIG. 52 is an agarose gel image illustrating the amplification of a T2 RNase from A. niger genomic DNA. Genomic DNA prepared from A. niger was subjected to PCR amplification using the forward (5'-TTYTGGGARCAYGARTG-GAAY-3', SEQ ID NO.:1, for amino acids F107-N112) and reverse (5'-CCYTTIACRTTRAARTARTARTA-3', SEQ ID NO.:2, for amino acids Y200-K206)] degenerate PCR primers designed according to amino acids F107-N112 and Y200-K206 found identical in RNase B1 and *A. saitoi* RNase M (GenBank Accession No. P19791, SEQ ID NO.:3). Note the presence of a 400 bp PCR product reflecting *A. niger* T2 RNase coding sequence.

Figure 53:
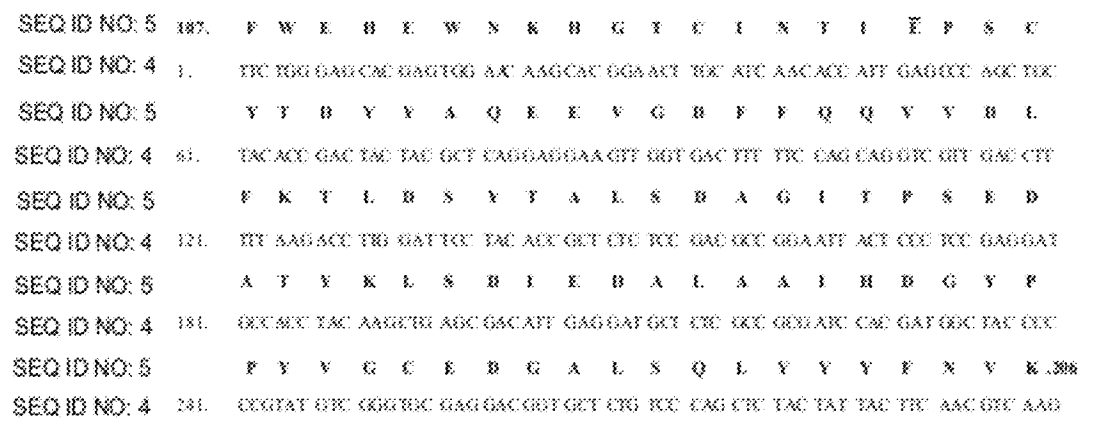

FIG. 53 is the nucleotide sequence of the 300 bp PCR product (SEQ ID NO.:4) prepared from the *A. niger* genomic DNA (as in FIG. 52). Note the open reading frame of the amino acid sequence (SEQ ID NO.:5) which is identical to F107-K206 of RNase M, except that in RNase B1 E123 (boxed) replaces D123 of *A. saitoi* RNase M.

Figure 54:
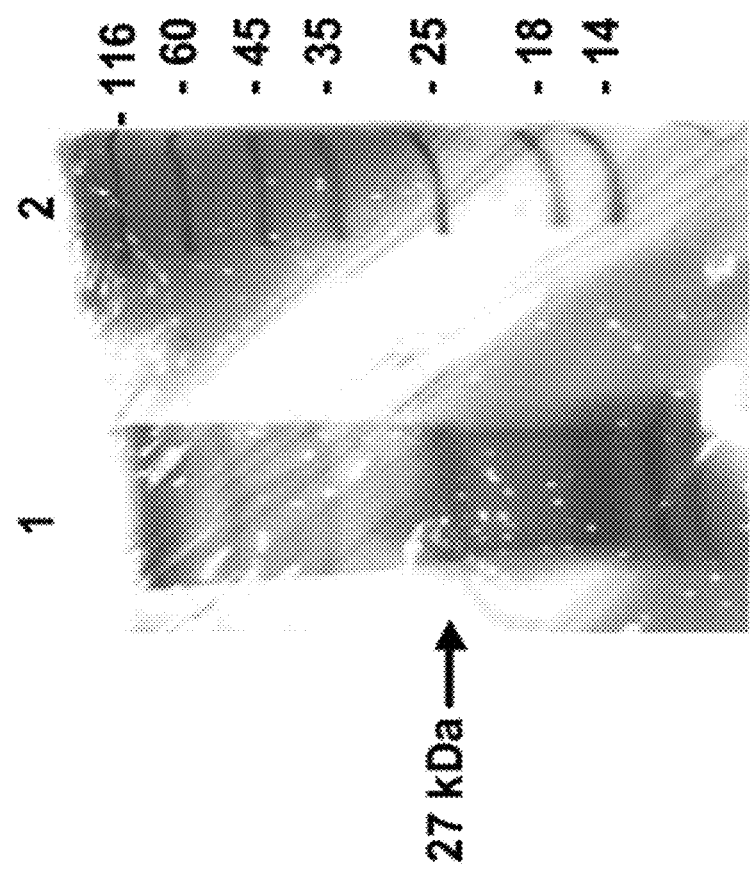

FIG. 54 is silver stain analysis of purified human recombinant RNase6PL. The recombinant protein of the RNase-positive yeast colony was purified by heat denaturation, centrifuged, and passed through a Q Sepharose column in a Fast FPLC and the eluted protein was loaded on an SDS-PAGE. Note the obtained 27 kDa purified protein (Lane 1). Lane 2: protein molecular markers.

DESCRIPTION OF THE PREFERRED EMBODIMENTS

The present invention is of the use of a ribonuclease of the T2 family or polynucleotide encoding same for modulating cellular motility, thereby preventing, inhibiting and/or reversing proliferation, colonization, differentiation, development of abnormally proliferating cells, inflammation, and/or infection in a subject. The present invention is further of pharmaceutical compositions containing, as an active ingredient, the ribonuclease of the T2 family having actin binding activity or a polynucleotide encoding same for treating diseases or disorders of cell motility in general, and inflammation, neurodegenerative disorders, cellular parasites and cancer in particular.

The use of ribonucleases with cytotoxic activity for inhibiting the proliferation of tumor cells is not new and has been demonstrated previously in the art. A ribonuclease of the A family which is commercially known as ONCONASE has been shown to inhibit cell proliferation in tumorous tissue in clinical trials. Several other RNases of the RNase A superfamily have also been demonstrated to have cytotoxic activity in addition to their ribonucleolytic activity. The toxicity of ONCONASE and other cytotoxic RNase A variants has been shown to depend on their ability to evade the cytosolic ribonuclease inhibitor protein (RI) and degrade cellular RNA (Haigis et al., Nuc Acid Res 2003; 31:1024-33).

Although the cytotoxicity of some ribonucleases is dependent to some extent on their ribonucleolytic activity, the level of ribonucleolytic activity does not always correlate to the level of cytotoxicity observed for ribonucleases. Furthermore, there exist several examples of ribonucleases which do not display cytotoxic activity altogether, yet function well as ribonucleases. The most known example is RNase A. In other cases, the reaction rate is sacrificed for more specific binding or improved function in some other capacity. For example, angigenin's active site is blocked by side chains that are not present in RNase A, rendering it 10.000-fold less active on general substrates, but more specific in cleaving ribosomal RNA. BS-RNase is a faster nuclease when it is monomeric. However, its cytotoxicity is greater, and inhibition by ribonuclease inhibitor is considerably reduced in the dimer form. Glycosylated RNase B is less active than RNase A on most substrates, while a frequently observed deamidation in BS-RNase, (asparagine 67 to isoaspartate) reduces the activity of RNase A mutants by cleaving a whole chain of H-bond structures in the to protein. (reviewed in Shein, C. H. 1997. Nature Biotechnol 15: 529-536).

Ribonucleases of the T2 family are characterized by their unique molecular features. A comparison between RNase members of the A and of the T2 families is summarized below in Table 2 (Location of amino acids are after RNase A and RNase T2 in families A and T2, respectively).

TABLE 2

| Feature | RNase A | RNase T2 |
|---|---|---|
| Molecular mass | 11-14 kDa (with the exception of BS-RNase) | 36 kDa. |
| Optimal temperature for RNase activity: | 37° C. | 50-60° C. |
| Optimal pH for RNase activity: | 6.5-8 | 3.5-5 |
| Glycosilation: | Not glycosylated | 12-25% of the total molecular mass |
| Base specificity: | Pyrimidine base-specific. | Non specific with adenylic acid preferential. |
| Disulfide bonds: | Four: Common: Cys28-84, Cys40-96, Cys58-110. In pancreatic RNases the fourth S-S bond is located between Cys65-72, forming a loop containing Glu69 and Asn71, which are part the nucleotide-binding site. In ONCONASE and bullfrog lectin Cys87-Cys104 form a COOH-terminal loop, which is located near the active site. Angiogenins have only 3 disulfide bonds. | Five: Cys3-20, Cys10-53, Cys19-120, Cys63-112 and Cys182-213. |
| Mechanis of RNase activity: | Active site Two steps in RNA cleavage (i) His12 acts as a general base and removes a proton from the 2'-hydroxyl group of the RNA. His119 acts as a general acid, donating a proton from the 5' O of the leaving nucleotide. (ii) The resultant 2'3'-cyclic nucleotides | Active site RNA catalysis is similar to RNase A. His46 and His109 function as general acid and base catalysts. Glu105 and Lys108 might plays a role in polarizing the P=O bond of the substrate or in stabilizing the pentacovalent transition state. |

TABLE 2-continued

| Feature | RNase A | RNase T2 |
|---|---|---|
| | are hydrolyzed, with the roles of His12 and His119 reversed. Lys41 stabilizes the pentavalent transition state. Substrate binding sites: GLn11 and Phe120 form hydrogen bonds with the substrate. In ONCONASE and bullfrog lectine Glu11 forms H-bond with the phosphate of the substrate. Gln96, Asn71, Glu111, of which Asn71 is the most conserved, might catalyze RNA cleavage. | Substrate binding sites: His104 (In plants it is Tyr or Asp) might act as the phosphate receptor of the substrate. There are two recognition sites: The major (B1) site contains Tyr57, Trp49 and Asp51. Asp51 is responsible for the adenine base recognition. A minor (B2) site contains Phe101, Gln95, Asn94, Ser93, Pro92 and Gln32. |

The ribonucleases of the T2 family have been identified in numerous microorganisms, as well as in plants, in which they play an active role in the pollination process, by selectively limiting the elongation of pollen tubes racing towards the ovules.

As uncovered by the inventors of the present invention and as is further detailed hereinbelow in Examples 1, 2 and 6, RNase B1, a T2 ribonuclease, either ribonucleolytically active or ribonucleolytically non-active, specifically binds to actin in elongating pollen tubes to thereby inhibit the elongation of pollen tubes and also to to actin of mammalian cells.

Actin is known to form filaments which are essential cytoskeletal components of cells, active in both maintaining cellular structure and in supporting intracellular transport of organelles. As a result, actin filaments are crucial to many cellular processes throughout the life cycle of normal and abnormal cells, including the motility, proliferation, colonization, differentiation, transformation, and survival of a variety of cells of mesodermal and/or neuroectodermal and/or ectodermal and/or endodermal origin, including fibroblasts, cells of the immune system, cells of the nervous system, cardiac muscle cells, skeletal muscle cells, vascular endothelial cells, vascular smooth muscle endothelial cells, and cells involved with repair of tissue injury and other developmental aspects including tissue formation. Numerous studies have shown that actin also participates in various cellular processes controlling generation of cancer cells (Jordan, M. A. & Wilson, L. 1998. Curr. Opin. Cell Biol. 10:123-130; Jammy, P. A. & Chaponnier, C. 1995. Curr. Opin. Cell Biol. 7:111-117: Sigmond, S. H. 1996. Cum Opin. Cell Biol. 8:66-73; Tapon, N. et al. 1997. Cum Opin. Cell Biol. 9:86-92). Thus, for example, actin filaments participates in abnormal cell proliferation (Assoian, R. K. & Zhu, X. 1997. Curr. Opin. Cell Biol. 9:93-98). Malignant cells were found more sensitive to cytochalasin B than normal cells (Hemstreet G. P. et al. 1996. J. Cell Biochem. 25S:197-204).

Since actin is a highly conserved protein, maintaining a high level of homology between evolutionary distant organisms it was hypothesized that the actin binding activity of RNase B1, which inhibits pollen tube elongation can be utilized, to without being limited by this theory, to specifically bind actin of mammalian cells, to thereby inhibit the proliferation, colonization, differentiation and/or development thereof.

While reducing the present invention to practice and as is further described in Example 2 and 5 of the Examples section, exogenous RNase B1 specifically binds to membranal actin and causes a cellular actin network disorder. As is shown in Examples 3-5, the effect of RNase B1 on mammalian cancer cells was further investigated in vitro and in vivo. As clearly demonstrated therein, RNase B1 (i) substantially decreases proliferation and/or colonization of adenocarcinoma cells grown in culture; and (ii) reduces the number of aberrant crypt foci (ACF), reduces the number and size of tumors, interferes with tumor angiogenesis, reduces the malignancy of tumors and the transition from adenoma to adenocarcinoma in a colon carcinoma rat model, in a preventive and/or therapeutic manner, while having no apparent side effects on healthy tissue in the colon or elsewhere.

Before explaining at least one embodiment of the invention in detail, it is to be understood that the invention is not limited in its application to the details set forth in the following description or illustrated by the Examples. The invention is capable of other embodiments or of being practiced or carried out in various ways. Also, it is to be understood that the phraseology and terminology employed herein is for the purpose of description and should not be regarded as limiting. Also, it is to be understood that the present invention is not bound to, or limited by, any theory or hypothesis which is indicated herein.

One or more ribonucleases of the T2 family are collectively referred to herein as T2-RNase. Similarly, one or more polynucleotides encoding one or more ribonucleases of the T2 family are collectively referred to herein as a polynucleotide encoding a T2-RNase (or same).

While reducing the present invention to practice, the inventors have revealed a previously undisclosed actin binding activity of members of the T2 RNase family, separate and independent of the ribonucleolytic catalytic activity of the proteins (see Example 6 and FIG. 31, hereinbelow). Actin binding activity of the T2 RNase has been quantified in vitro (see Example 3, FIG. 11 hereinbelow), and has been localized to the cell surface in diverse models of cell growth, motility and proliferation (see Example 3, FIGS. 12a-12c, and Example 5, FIGS. 29 and 30 hereinbelow). Further, the T2 RNase actin binding activity correlates with disruption of actin filament organization in cell protrusions, and strong inhibition of tube growth (see Example 3, FIGS. 9a and 9b, and Example 5, FIGS. 28a and 28b hereinbelow) and angiogenesis (see Example 4, FIGS. 24a-24c and 26c hereinbelow). Further results revealed that the T2 RNase actin binding activity, disruption of cell protrusions and inhibition of motility further correlates with significant inhibition of tumor growth (see Examples 4, FIGS. 22-24 hereinbelow) and prevention of malignancy (see Example 4, FIG. 26 hereinbelow) in both newly proliferating and established, well-developed tumors. Microhistopathological and DNA-based (TUNEL) analyses of the T2 RNase-treated tumors has revealed a strong proapoptotic effect of T2 RNase having an actin binding activity, associated with inhibition of tumor proliferation and metastatic growth, and reduction in tumor volume (see Example 14, FIGS. 43a-43b, 44a-44b and 45a-45b hereinbelow). As detailed in the Background section hereinabove, dynamic actin filament assembly and disassembly at the cell surface is highly regulated and is critical to all aspects of cell motility, growth and development of both normal and abnormal cells.

Thus, according to one aspect of the present invention there is provided a method of preventing, inhibiting and/or reversing proliferation, colonization, differentiation and/or development of abnormally proliferating cells in a subject. The method according to this aspect of the present invention is effected by administering to the subject a therapeutically effective amount of a ribonuclease of the T2 family or of a polynucleotide encoding and capable of expressing in vivo a recombinant ribonuclease of the T2 family, either per se or as an active ingredient of a pharmaceutical composition.

While reducing the present invention to practice, it was uncovered, for the first time, that exposing abnormally proliferating cells, such as tumors, xenografts and metastases (see Example 10 and 14 and FIGS. 43-45,) to a ribonuclease of the T2 family, enhanced apoptotic processes in the cells. The proapoptotic effects of the T2 RNase correlated with the suppression of tumor and metastatic growth and proliferation seen in Examples 10 and 14. It will be appreciated, that diseases associated with inhibition of apoptosis include those diseases in which an excessive accumulation of cells occurs (neoplastic diseases, autoimmune diseases).

In both solid and haematological tumors, the malignant cells show an abnormal response to apoptosis inducers (Watson A J M. 1995. Gut 37: 165-167; Burch W. et al. 1992. Trends Pharmacol Sci 13:245-251). In these diseases cycle-regulating genes such as p53, ras, c-myc and bcl-2 suffer mutations, inactivation or dysregulations associated to malignant degeneration (Merrit A J et al. 1994. Cancer Res 54:614-617; Iwadate Y et al. 1996. Int J Cancer 69:236-240; Müllauer L et al. 1996. Hepatology 23: 840-847; Newcomb E W. 1995. Leuk Lymphoma 17: 211-221). The expression of bcl-2 is considered to be a predictive factor for worse prognosis in prostate and colonic cancer and in neuroblastoma (Thompson C B. 1995. Science 267: 1456-1462). It has been shown that a number of antineoplastic therapies induce apoptosis in tumor cells (for reviews see: Sun S Y et al. 2004. J Natl Cancer Inst. 96:662-672; Schulze-Bergkamen H and Krammer P H. 2004. Semin Oncol. 31:90-119; Abend M. 2003. Int J Radiat Biol. 79:927-941).

Defects in the apoptosis may lead to autoimmune diseases such as lupus erythematosus (Carson DA. and Rebeiro J M. 1993. Lancet. 341: 1251-1254. Aringer M. et al. 1994. Arthritis Rheum. 37:1423-1430), rheumatoid arthritis (Liu H. and Pope R M. 2003. Curr Opin Pharmacol. 3:317-22.) and myasthenia gravis (Masunnaga A. et al. 1994. Immunol Lett. 39: 169-172.). Pathogens, such as adenovirus, EBV, cowpox and chlamydia (Thompson C B. 1995. Science 267:1456-1462; Marshall W L. et al. 1999. J. Virol. 73:5181-5185, Deveraux Q L, et al. 1999. J Clin Immunol. 19:388-98, Fan T. et al. 1998. J Exp Med. 187:487-496.) have also been shown to interfere with cellular apoptosis. In chronic inflammatory, hyperproliferative skin diseases such as psoriasis, an abnormally low rate of apoptosis contributes to the development of epidermal hyperplasia. It was shown that keratinocytes respond to a variety of external and internal growth factors, including some proinflammatory cytokines which may suppress keratinocytes apoptosis, such as IL-15 (Ruckert R. et al. 2000. J. Immunol. 165:2240-2250).

Thus, according to another aspect of the present invention, there is provided a method of enhancing apoptosis of a cell, the method comprising providing to the cell an effective concentration of a ribonuclease of the T2 family having an actin binding activity, or a polynucleotide encoding and capable of expressing in vivo the ribonuclease of the T2 family, thereby enhancing apoptosis. Enhancing apoptosis of a cell by the method of the present invention can be applied clinically, in the treatment and/or prevention of diseases associated with apoptosis, such as the neoplastic diseases, autoimmune diseases, inflammatory disease, hyperproliferative disease and infectious diseases described hereinabove. Administration of a ribonuclease of the T2 family having an actin binding activity, or a polynucleotide encoding and capable of expressing in vivo the ribonuclease of the T2 family for enhancing apoptosis in cells of a subject in need thereof can be effected by any of the methods described herein. Detection of enhanced apoptosis, and the monitoring of changes in the level of apoptosis in cells or tissues or tissue samples following exposure to T2 RNase, can be effected by cytological, pathology and biochemical (for example, the TUNEL assay described hereinbelow) means known in the art, as described hereinbelow. The ribonuclease of the T2 family having an actin binding activity can be a recombinant T2 RNase, expressed in a heterologous expression system. Whereas the actin binding and therapeutic character of ribonucleases of the T2 family having actin binding activity have been shown to be separate and independent of the ribonucleolyic activity, in one embodiment the T2 RNase is devoid of ribonucleolytic activity. The therapeutically effective amount of a ribonuclease of the T2 family or of a polynucleotide encoding and capable of expressing in vivo a recombinant ribonuclease of the T2 family can be administered to the cells subject in need thereof, either per se or as an active ingredient of a pharmaceutical composition.

Thus, according to another aspect of the present invention there is provided a pharmaceutical composition comprising, as an active ingredient, a ribonuclease of the T2 family a polynucleotide encoding and capable of expressing in vivo a recombinant ribonuclease of the T2 family, and a pharmaceutically acceptable carrier.

According to yet another aspect of the present invention there is provided a method of preparing a medicament useful in preventing, inhibiting and/or reversing proliferation, colonization, differentiation and/or development of abnormally proliferating cells comprising the step of combining a ribonuclease of the T2 family or a polynucleotide encoding and capable of expressing in vivo a recombinant to ribonuclease of the T2 family, with a pharmaceutically acceptable carrier.

Yet further, there is provided a method of preparing a medicament useful in treating and/or preventing a disease or condition characterized by excessive cell motility and/or abnormal accumulation of cells. The method is effected by combining a ribonuclease of the T2 family or a polynucleotide encoding and capable of expressing in vivo a recombinant ribonuclease of the T2 family, with a pharmaceutically acceptable carrier.

The medicament is preferably identified as providing a treatment for a specified proliferative disorder or disease, such as a specified cancer. Such an identification can be made in print on, for example, a container containing the medicament or on a leaflet, as is well known in the art.

The method and pharmaceutical composition of the present invention can be used for, for example, (i) treating a tumor in a subject; (ii) preventing, inhibiting and/or reversing the development a tumor in a subject; (iii) preventing, inhibiting and/or reversing transformation of a benign tumor to a malignant tumor in a subject; (iv) preventing, inhibiting and/or reversing tumor angiogenesis in a subject; (v) reducing the number of individual tumors in a subject; (vi) reducing tumor size in a subject; (vii) reducing a number of malignant tumors in a subject; and/or (viii) preventing, inhibiting and/or reversing transformation of a tissue into a tumor in a subject.

The T2-RNase can be derived from a native source, as is further exemplified in Example 1 that follows, or alternatively, it can be produced as a recombinant protein using an appropriate polynucleotide (see Table 3 below and the following descriptions) and expression system. Expressing and purifying recombinant proteins is well known in the art and can be effected by any one of a plurality of alternative techniques described in detail in any one of a number of text books and laboratory protocol books, including, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) to "Genome Analysis: A Laboratory Manual Series", Vols. 1-4, Cold Spring Harbor Laboratory Press, New York (1998).

TABLE 3

| | Source | Name(Prot) | Name(Gene) | Reference(s) | GeneBank Accession No. |
|---|---|---|---|---|---|
| Bacteria | *Aeromonas hydrophila* | | Locus RNI | Favre, D. et al. 1993. J. Bacteriol. 175: 3710-3722. | Q07465 |
| | *Haemophilus influenzae* | Rnase HI0526 | Locus RN26 | Fleischmann, R. D., et al. 1995. Science 269: 496-512. | P44012 |
| | *Escherichia coli* | Rnase I | Locus RNI | Meador, J. III. & Kennell, D. 1990. Gene 95: 1-7. Oshima, T., et al. 1996. DNA Res. 3: 137-155. Henikoff, S. & Henikoff, J. G. 1994. Genomics 19: 97-107. | P21338 |
| | *Aspergillus oryzae* | Rnase T2 | rnt B | Kawata Y. et al. 1988. Eur J. Biochem 176(3): 683-97. Kawata Y. et al. 1990. Eur J. Biochem 187: 255-62. Ozeki K, et al. 1991. Curr Genet. 19: 367-73. | P10281 |
| Fungi | *Rhisopus niveus* | Rnase Rh | | Horiuchi, H. et al. 1988. J. Biochem. 103: 408-418. Kurihara, H. et al. 1992. FEBS Lett. 306: 189-192. Kurihara, H. et al. 1996. J. Mol. Biol. 255: 310-320. Ohgi, K. et al. 1991. J. Biochem. 109: 776-785. | P08056 |
| | *Trichoderma viride* | Rnase Trv | | Inada, Y. et al. 1991. J. Biochem. 110 (6), 896-904. | P24657 |
| | *Lentinula edodes* (shiitake mushroom) | Rnase Irp | | Kobayashi, H. et al. 1992. Biosci. Biotechnol. Biochem. 56: 2003-2010. | AAB24971 |
| | *L. edodes* | Rnase Le2 | | Kobayashi, H. et al. 1992. Biosci. Biotechnol. Biochem. 56: 2003-2010. Shimada, H. et al. 1991. Agric. Biol. Chem. 55: 1167-1169. | P81296 |
| | *Irpex lacteus* | Rnase Irp1 | | Watanabe, H., et al. 1995. Biosci. Biotechnol. Biochem. 59: 2097-2103. | AAB35880 |
| | *Physarum polycephlum* | Rnase Phyb | | Inokuchi, N. et al. 1993. J. Biochem. 113: 425-432. | P81477 |
| Plants | *Arabidopsis thaliana* | RNS2 | Locus RNS2 | Green, P. J. 1993. Proc. Natl. Acad. Sci. U.S.A. 90: 5118-5122. | P42814 |
| | *A. thaliana* | Rnase 3 | Locus RNS3 | Bariola, P. A., et al. 1994. Plant J. 6: 673-685. | P42815 |
| | *A. thaliana* | Rnase 1 | Locus RNS1 | Bariola, P. A., et al. 1994. Plant J. 6: 673-685. | P42813 |
| | *Lycopersicon esculentum* (cultured tomato) | Rnase LE | RNALE | Kock, M. et al. 1995. Plant Mol. Biol. 27: 477-485. Jost, W. et al. 1991. Eur. J. Biochem. 198: 1-6. | P80022 |
| | *L. esculentum* | Rnase LX | RNLX | Kock, M., et al. 1995. Plant Mol. Biol. 27: 477-485. Loffler, A., et al. 1993. Eur. J. Biochem. 214: 627-633. | P80196 |
| | *Nicotiana alata* (tobacco) | S-RNase | S | Anderson, M. A., et al. 1986. Nature 321: 38-44. Matton, D. P. et al. 1995. Plant Mol. Biol. 28: 847-858. McClure, B. A. et al. 1989. Nature 342: 95-97. | P04002 |
| | *Malus domestica* (apple tree) | S-RNases | S | Sassa, H., et al. 1996. Mol. Gen. Genet. 250: 547-557. | |

TABLE 3-continued

|  | Source | Name(Prot) | Name(Gene) | Reference(s) | GeneBank Accession No. |
|---|---|---|---|---|---|
|  | *Pyrus pyrifolia* (Japanese pear) | S-RNases | S | Norioka, N., et al. 1996. J. Biochem. 120; 335-345. |  |
|  | *Momordica charantia* (bitter gourd) | RNase MC | Locus RNMC | Blaxter, M. L., et al. 1996. Mol. Biochem. Parasitol. 77: 77-93. Ide, H. et al. 1991. FEBS Lett. 284: 161-164. Ide, H. et al. 1991. FEBS Lett. 289: 126. | P23540 |
| Animals | *Gallus gallus* (chicken) | RNase CL1 |  | Uchida, T. et al. 1996. Biosci. Biotechnol. Biochem. 60: 1982-1988. | JC5126 |
|  | *Rana catesbeiana* (bull frog) | RNase RCL2 |  | Yagi, H. et al. 1995. Biol. Pharm. Bull. 18: 219-222. Liao, Y. D. et al. 1996. Protein Expr Purif. 7: 194-202. Liao Y D, et al. 1994. Eur J Biochem. 222: 215-20. Liao, Y. D. et al. 1998. J. Biol. Chem. 273: 6395-401 | PC2347 |
|  | *Drosophyla melanogaster* | RNase DM | DmRNase | Lankenau, D. H. et al. 1990. Chromosoma 99: 111-117. Hime, G., et al. 1995. Gene 158: 203-207. | X15066 |
|  | *Crassostera gigus* (pacific oyster.) | RNase Oy | Locus JX0295 | Watanabe, H. et al. 1993. J. Biochem. 114: 800-807. | JX029 |
|  | *Todarodes pasificus* (Japanese flying squid) | RNase Tp |  | Kusano, A. et al. 1998. Biosci. Biotechnol. Biochem. 62: 87-94. | PMID 9501521 |
|  | *Homo sapiens* | RNase 6 precurs. | RNase6PL | Trubia, M. et al. 1997. Genomics 42: 342-344. | NP003721 |

For some applications it may be beneficial to use a ribonuclease which substantially lacks ribonucleolytic activity, which may have or cause undesired side effects. As used herein the phrase "substantially lacks ribonucleolytic activity" refers to (i) an inactivated ribonuclease (either natural or recombinant) of the T2 family which has 0-10% ribonucleolytic activity as is compared to a similar, non-inactivated, ribonuclease; and/or (ii) a recombinant mutant (natural isolate or man induced) ribonuclease of the T2 family which has 0-10% ribonucleolytic activity as is compared to a similar, non-mutant, ribonuclease. Inactivating the ribonucleolytic to activity of the ribonuclease of the T2 family may be effected by a process selected from the group consisting of, autoclaving and chemically denaturing or inactivating.

As used herein, the term "autoclaving" is defined as exposure, in an autoclave, to superheated steam heated to about 121° C. at high pressure conditions (for example, 15 psi), for at least 20 minutes. Chemical denaturing may be effected by exposure to extremes of pH, and chemical agents causing alteration in the amino acid side chains and/or chemical bond structure of the ribonuclease of the T2 family, such as iodoacetylation, as described in detail hereinbelow (Example 6).

As is further detailed in Examples 2 and 6 below, it has been shown by the inventors of the present invention that the inhibition of cell motility, the inhibition of apoptosis, the anti-proliferation, anti-colonization, anti-differentiation and/or anti-development activities of RNase B1 are not dependent on its ribonucleolytic activity, as boiled, autoclaved and chemically inactivated (acetylated) RNase B1, which has little (10%) or substantially no (0-10%) ribonucleolytic activity retained substantially all of its actin-binding and anti-proliferation, anti-colonization, anti-differentiation and/or anti-development activities.

Thus, a T2-RNase protein according to the present invention can be utilized both in a native, ribonucleolytic active, form, or, alternatively, in a silent, or repressed ribonucleolytic form, having no (0%) or little (up to 10%) ribonucleolytic activity, yet which retains its other activities. As such, the term "T2-RNases" is meant to encompass all the anti-proliferation, anti-colonization, anti-differentiation and/or anti-development forms of the protein, regardless of other activities thereof. Thus, in one embodiment, the T2-RNase of the present invention is substantially devoid of ribonuclease activity yet has an actin binding activity. In a preferred embodiment which actin binding activity of the T2 RNase is thermostable. Further, there is to provided a method inactivating a ribonuclease activity, yet maintaining an actin binding activity of a ribonuclease of the T2 family. The method is affected by subjecting the ribonuclease to denaturing conditions sufficient for substantially inactivating the ribonuclease activity, yet maintaining the actin binding activity.

It will be appreciated that utilizing a T2-RNase, either directly or expressed from a polynucleotide, which displays a desired activity and yet is devoid of, or repressed in, ribonucleolytic activity is particularly advantageous since ribonucleolytic activity can produce undesired side effects in a subject.

A polypeptide representing the amino acid sequence of a T2-RNase as defined herein can be produced by any one of several methods well known in the art. For example the polypeptide can be produced synthetically by standard peptide synthesis techniques, for example using either standard 9-fluorenylmethoxycarbonyl (F-Moc) chemistry (see, for example, Atherton, E. and Sheppard, R. C. 1985, J. Chem. Soc. Chem. Comm 165) or standard butyloxycarbonate (T-Boc) chemistry, although it is noted that, more recently, the fluorenylmethoxycarbonyl (Fmoc)/tert-butyl system, developed by Sheppard has found increasingly wide application (Sheppard, R. C. 1986 Science Tools, The LKB Journal 33, 9).

While reducing the present invention to practice, it was uncovered, for the first time, that many ribonucleases of the T2 family, derived from organisms of diverse phylogentic origin from bacteria to yeast (Example 16, FIG. 47a-47b) have actin binding activity, which correlates with the therapeutic character and inhibition of cell motility, abnormal cell proliferation and apoptosis. Thus, the T2-RNase protein can also be isolated and purified by methods well known in the art from organisms known to express this protein. Such organisms include, for example, *Aeromonas hydrophila, Haemophilus influenzae, Escherichia coli, Aspergillus oryzae, Aspergillus phoenicis, Rhisopus niveus, Trichoderma viride, Lentinula edodes, Irpex lacteus; Physarum polycephlum, Arabidopsis thaliana, Lycopersicon esculentum, Nicotiana alata, Malus domestica, Pyrus pyrifolia, Momordica charantia, Gallus gallus, Rana catesbeiana, Drosophyla melanogaster, Crassostera gigus, Todarodes pasificus* and *Homo sapiens*. It is, however, anticipated that other organisms yet not known to produce RNase, once uncovered as such, could also be used as a source for T2-RNase according to the present invention.

It will be appreciated that some therapeutic and diagnostic use of T2 ribonucleases of the present invention will require purified T2 RNases. Thus, simple, inexpensive methods of purification of T2 RNases are advantageous. While reducing the present invention to practice, it was uncovered that recombinant ribonuclease of the T2 family can be isolated and purified by boiling, fractionation by column chromatography (see Example 19, FIG. 54 hereinbelow), and assaying the collected fractions for ribonucleolytic activity. Thus, there is also provided a novel method for isolating T2 ribonuclease protein, the method comprising heat denaturating a T2 containing sample which comprises cells expressing a T2 ribonuclease protein, separating the supernatant, preferably by centrifigation, fractionating the supernatant, identifying a fraction of the supernatant having a T2 ribonuclease protein and purifying the T2 RNase fraction to substantial purity. In one embodiment, fractionating the supernatant is effected by column chromatography, for example, Q SEPHAROSE or other protein separation media well known to one of ordinary skill in the art. Identification of the T2 RNase bearing fractions may be made according to physical characteristics (such as electrophoretic mobility) and functional criteria (ribonucleolytic activity, actin binding activity). Methods for physical and functional assessment of the purified RNase are well known in the art, as described hereinbelow.

Alternatively and preferably a T2-RNase protein can be recombinantly produced by expressing a polynucleotide encoding same, using an appropriate expression vector system. In one embodiment, the expression system is a heterologous expression system selected from a bacterial, yeast, or higher cell expression system, wherein higher cell expression systems include animal or plant expression systems. Preferably, an expression system is selected which provides suitable post translational modifications. Suitable expression vector systems include, but are not limited to, mammalian cells infected with a virus (e.g., adenovirus, retrovirus, herpes simplex virus, avipox virus); insect cells infected with a virus (e.g., baculovirus); genetically modified plants or plant cells transformed with a plasmid, a plant virus or an *Agrobacterium*; transformed microorganisms such as yeasts containing yeast vectors, or bacteria transformed with bacteriophage DNA, plasmid DNA, or cosmid DNA. The expression controlling elements of vectors vary in their strengths and specifications depending on the host-vector system utilized, any one of a number of to suitable transcription and translation elements may be used. A recombinantly produced T2-RNase may be purified from host cells by the methods described hereinbelow, or by affinity chromatography, electrophoresis, high-performance liquid chromatography (HPLC), immunoprecipitation, sedimentation or any other method known to the art.

A purified T2-RNase can be used to prepare a medicament according to the present invention by means of conventional mixing, dissolving, granulating, dragee-making, levigating, emulsifying, encapsulating, entrapping or lyophilizing processes with the addition of the appropriate pharmaceutically acceptable carriers and/or excipients or alternatively it can be linked to appropriate delivery vehicles as described hereinabove.

A polynucleotide according to the present invention can encode a native T2-RNase protein, which term in this context to describe a T2-RNase having both anti-proliferative and ribonucleolytic activities, or alternatively, a polynucleotide according to the present invention can encode a silent or repressed T2-RNase mutant, having no or little ribonucleolytic activity, to be expressed (e.g., transcribed and translated) in vivo into a protein which is substantially free of ribonucleolytic activity.

As such, the term "polynucleotide" when used herein in context of T2-RNases in general, or in context of any specific T2-RNase, refers to any polynucleotide sequence which encodes a T2-RNase active in preventing, inhibiting and/or reversing proliferation, colonization, differentiation and/or development of abnormally proliferating cells, either having or substantially devoid of ribonucleolytic activity. Polynucleotides encoding a T2-RNase devoid of ribonucleolytic activity can be obtained using known molecular biology techniques, such as random mutagenesis, site-directed mutagenesis and enhanced evolution techniques. Site directed mutagenesis can be readily employed because the amino acid residues essential for the ribonucleolytic activity of T2-RNases have been recognized (see Kusano et al., 1998. Biosci. Biothechnol. Biochem. 62:87-94, which is incorporated herein by reference, and Table 3 above).

It will be appreciated that aberrant or excessive or insufficient regulation of actin function and intracellular actin distribution and cellular motility can lead to perturbed cellular functions, which in turn can lead to cellular disorders (or exacerbate to existing cellular disorders). As used herein, a "cellular disorder" includes a disorder, disease, or condition characterized by aberrant or insufficient cellular ability to move or migrate properly in response to certain stimuli (e.g. tissue damage), or inability to properly regulate actin function and distribution within the cell.

While reducing the present invention to practice, it was shown, for the first time, that T2 RNase not only inhibits cell motility, actin filament assembly and reassembly, tube formation and cel proliferation in vivo, but can also directly inhibit the motility and invasiveness of cancer cells, as measured in vitro (Example 12, Table 5). Thus, the T2 RNases having actin binding activity of the present invention, and compositions comprising such, may act as novel therapeutic agents for controlling cellular disorders related to motility, including cancer (e.g. tumor angiogenesis and metastasis), immune regulation, neurodegenerative and inflammatory disease. Additionally, the T2 RNases having actin binding activity may act as novel therapeutic agents for ameliorating certain cellular disorders and conditions through their ability to migrate and to regulate tissue injury response.

Thus, according to the present invention there is provided a method of inhibiting motility of a cell. The method is effected by providing to the cell a ribonuclease of the T2 family having an actin binding activity, or a polynucleotide encoding and capable of expressing in vivo the ribonuclease of the T2 family. Further there is provided a method of treating and/or preventing a disease or condition characterized by excessive cell motility in a subject in need thereof. The method is effected by administering to the subject a therapeutically effective amount of a ribonuclease of the T2 family having an actin binding activity, or a polynucleotide encoding and capable of expressing in vivo said ribonuclease of the T2 family.

Disruption of actin assembly and disassembly affects cell motility, development, growth, proliferation and reproduction. Thus, the compositions and methods of present invention can be used for treating conditions, syndromes or diseases characterized by abnormal accumulation of cells. Diseases or conditions characterized by abnormal accumulation of cells include, but are not limited to, inflammatory diseases, neurodegenerative diseases, and cancer. Further, the compositions and methods of the present invention can be used for inhibiting actin to filament assembly and disassembly in a cell, effected by providing to the cell a ribonuclease of the T2 family having actin binding activity, or a polynucleotide encoding and capable of expressing in-vivo the ribonuclease of the T2 family.

Thus, the present invention can be used for treating conditions, syndromes or diseases characterized by abnormally proliferating cells, such as cancerous or other cells, such as, but not limited to, a malignant or non-malignant cancer including biliary tract cancer; brain cancer; breast cancer; cervical cancer; choriocarcinoma; endometrial cancer; esophageal cancer; gastric cancer; intraepithelial neoplasms; lymphomas; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas, papilloma, blastoglioma, Kaposi's sarcoma, squamous cell carcinoma, astrocytoma, head cancer, neck cancer, bladder cancer, colorectal cancer, thyroid cancer, pancreatic cancer, gastric cancer, hepatocellular carcinoma, leukemia, lymphoma, Hodgkin's disease, Burkitt's disease, arthritis, rheumatoid arthritis, diabetic retinopathy, angiogenesis, restenosis, in-stent restenosis, vascular graft restenosis, proliferative vitreoretinopathy, chronic inflammatory proliferative disease, dermatofibroma and psoriasis.

As used herein the terms "cancer" or "tumor" are clinically descriptive terms which encompass a myriad of diseases characterized by cells that exhibit abnormal cellular proliferation. The term "tumor", when applied to tissue, generally refers to any abnormal tissue growth, characterized in excessive and abnormal cellular proliferation. A tumor may be "benign" and unable to spread from its original focus, or "malignant" or "metastatic" and capable of spreading beyond its anatomical site to other areas throughout the host body. The term "cancer" is an older term which is generally used to describe a malignant tumor or the disease state arising therefrom. Alternatively, the art refers to an abnormal growth as a neoplasm, and to a malignant abnormal growth as a malignant neoplasm.

The T2 RNase having an actin binding activity of the present invention can be used in the preventive treatment of a subject at risk of having a cancer. A "subject at risk of having a cancer" as used herein is a subject who has a high probability of developing cancer. These subjects include, for instance, subjects having a genetic to abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is exposed to the T2 RNase having actin binding activity of the present invention, the subject may be able to prevent any cancer that does form from becoming metastatic.

The T2 RNase having an actin binding activity of the present invention is also useful for treating and/or preventing disorders associated with inflammation in a subject. Immune or hematopoietic cells exposed to T2 RNases having an actin binding activity would have a reduced ability to migrate. Thus T2 RNases having actin binding activity is useful for preventing inflammation associated with immune cell migration and for treating and preventing inflammatory disorders and ischemic diseases.

Inflammatory disorders and ischemic diseases are characterized by inflammation associated with neutrophil migration to local tissue regions that have been damaged or have otherwise induced neutrophil migration and activation. While not intending to be bound by any particular theory, it is believed that excessive accumulation of neutrophils resulting from neutrophil migration to the site of injury, causes the release toxic factors that damage surrounding tissue. When the inflammatory disease is an acute stroke a tissue which is often damaged by neutrophil stimulation is the brain. As the active neutrophils accumulate in the brain an infarct develops.

An "inflammatory disease or condition" as used herein refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil accumulation at a local tissue site. These conditions include but are not limited to meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

An "ischemic disease or condition" as used herein refers to a condition characterized by local inflammation resulting from an interruption in the blood supply to a tissue due to a blockage or hemorrhage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

In some aspects of the invention the T2 RNase of the present invention is provided in an effective amount to prevent migration of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327-336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The T2 RNase or polynucleotide encoding same of the present invention can be used to assay cells for sensitivity to inhibition of cellular motility, for example, in testing their ability to cross a barrier. Preferably the tumor cells are prevented from crossing a barrier. The barrier for the tumor cells may be an artificial barrier in vitro or a natural barrier in vivo. In vitro barriers include but are not limited to extracellular matrix coated membranes, such as Matrigel. Thus, T2 RNase can be provided to cells which can then be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378-383. Matrigel is a reconstituted basement membrane containing type IV collagen, laminin, heparan sulfate proteoglycans such as perlecan, which bind to and localize bFGF, vitronectin as well as transforming growth factor-.beta. (TGF-.beta.), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated herein by reference. An in vivo barrier refers to a cellular barrier present in the body of a subject.

Any ribonuclease of the T2 family which has the actin binding, anti-proliferation, anti-colonization, anti-differentiation and/or anti-development activities described herein and exemplified in the Examples section that follows can be used as a therapeutic agent in accordance with the teachings of the present invention. Similarly, any polynucleotide encoding a ribonuclease of the T2 family which has the anti-proliferation, anti-colonization, anti-differentiation and/or anti-development activities described herein can be used as a therapeutic agent in accordance with the teachings of the present invention. A non exhausting list of ribonucleases of the T2 family is provided in Table 3, above. As is further exemplified by the Examples that follow, RNase B1, which is a member of the T2 family, has anti-proliferation, anti-colonization, anti-differentiation and/or anti-development activities as was determined by in vivo and in vitro assays. In addition, RNase B1 is shown to bind to actin even when treated so as to render it free of ribonuclease activity. Thus, the present invention provides three different assays with which one of ordinary skills in the art could test a given ribonuclease for its actin binding, anti-proliferation, anti-colonization, anti-differentiation and/or anti-development activities, these are an in vitro assay for determining the effect of the tested ribonuclease on cancerous cells, in vivo assay for determining the effect of the tested ribonuclease on tumor development, and another in vitro assay for determining the ability of the tested ribonuclease to bind to cellular and/or free actin. Without limiting the present invention by any theory, it is believed that an ability of a ribonuclease to bind to actin is indicative that such a ribonuclease has anti-proliferation, anti-colonization, anti-differentiation and/or anti-development activities.

A ribonuclease according to the present invention can be administered to an organism, such as a human being or any other mammal, per se, or in a pharmaceutical composition where it is mixed with suitable carriers or excipients.

As used herein a "pharmaceutical composition" or "medicament" refers to a preparation of one or more of the ribonucleases or polynucleotides encoding same as described herein, with other chemical components such as physiologically suitable carriers and excipients. The purpose of a pharmaceutical composition is to facilitate administration of a compound to an organism.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Pharmaceutical compositions may also include one or more additional active ingredients, such as, but not limited to, anti inflammatory agents, antimicrobial agents, anesthetics, cancer therapeutic agents and the like in addition to the main active ingredient. A detailed description of commonly used additional agents suitable for use with the compositions of the present invention is presented hereinbelow.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen.

While reducing the present invention to practice, significant therapeutic effects of the ribonuclease of the T2 family having an actin binding activity were revealed using a broad variety of means of administration, in diverse models of abnormal cell proliferation and accumulation. Intraperitoneal administration, providing rapid systemic uptake and distribution of the T2 RNase, was found effective in suppressing tumor growth and development in subcutaneous tumors in nude mice (Examples 9 and 13, FIGS. 35 and 39*a-b*) and intraperitoneal tumors (Example 8, FIGS. 33*a-d*). Intravenous administration, providing even more rapid systemic uptake of the T2 RNase, was also found effective in suppressing and treating subcutaneous xenografts (Example 13, FIGS. 36*a-b*), and remote (lung) metastatic spread of intravenous tumors (Example 8, FIGS. 34*a-e*). Direct administration of, and preincubation of cells with the T2 RNase has been found effective in preventing tumor growth in breast carcinoma (Example 12, Table 6), colon carcinoma (Example 12, Table 6), melanoma (Example 12, FIG. 38), in-vivo, angiogenic factor induced angiogenesis and microvessel density (Example 10, FIG. 37) and cell tube formation in both plant (Example 1, FIGS. 8 and 9) and human HUVE cells (Example 7, FIGS. 32*a-h*). Oral administration of T2 RNase, in the form of microcapsules, has been found effective in reducing tumor proliferation, tumor size, tumor vascularization and the number of aberrant crypt foci (Example 4, FIGS. 23*a*-23*c*, 24*a*-24*d*, and 25*a*-25*c*) when administered early in colon tumor (DMH model) induction. Similar oral administration of T2 RNase to animals harboring already well developed tumors reduced the degree of vascularization and malignancy of colon cancer tumors in rats (Example 4, FIG. 27*c*), despite exposure of the RNase to digestive processes and low doses presumed delivered intraintestinally. It will be appreciated that encapsulation methods providing effective intestinal release of compositions are well known in the art, and use of such is expected to increase the effectiveness of oral administration of T2 RNase in cases of already established tumors.

Thus, to effect administration the pharmaceutical composition of the present invention includes a suitable pharmaceutical carrier and an effective amount of a T2-RNase or a polynucleotide encoding same, and is administered, for example, topically, intraocularly, parenterally, orally, intranasally, intravenously, intramuscularly, subcutaneously or by any other effective means via methods well known in the art.

For intravenously, intramuscularly or subcutaneously injection, a T2-RNase or a polynucleotide encoding same may be formulated in aqueous solutions, preferably in physiologically compatible buffers such as Hank's solution, Ringer's solution, or physiological saline buffer. For example, a physiologically appropriate solution to containing an effective amount of a T2-RNase or a polynucleotide encoding same can be administered systemically into the blood circulation to treat a cancer or tumor which cannot be directly reached or anatomically isolated. A physiologically appropriate solution containing an effective amount of a T2-RNase or a polynucleotide encoding same may be directly injected into a target cancer or tumor tissue by a needle in amounts effective to treat the tumor cells of the target tissue.

For transmucosal administration, penetrants appropriate to the barrier to be permeated are used in the formulation. Such penetrants are generally known in the art.

For oral administration, the pharmaceutical composition of the present invention can be formulated readily by combining a T2-RNase or a polynucleotide encoding same with pharmaceutically acceptable carriers well known in the art. Such carriers enable a T2-RNase or a polynucleotide encoding same to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Additional pharmaceutical compositions, which can be used orally, include to push-fit capsules made of gelatin as well as soft, sealed capsules made of gelatin and a plasticizer, such as glycerol or sorbitol. The push-fit capsules may contain a T2-RNase or a polynucleotide encoding same in admixture with filler such as lactose, binders such as starches, lubricants such as talc or magnesium stearate and, optionally, stabilizers. In soft capsules, a T2-RNase or a polynucleotide encoding same may be dissolved or suspended in suitable liquids, such as fatty oils, liquid paraffin, or liquid polyethylene glycols. In addition, stabilizers may be added. All formulations for oral administration should be in dosages suitable for the chosen route of administration.

Oral delivery of the pharmaceutical composition of the present invention may not be successful due to the pH and enzyme degradation present in the gastrointestinal tract. Thus, such pharmaceutical compositions must be formulated to avoid undesirable circumstances. For example, enteric coating can be applied to oral solid formulation. Substances with acidic-resistant properties such as cellulose acetate phtalate (CAP), hydroxypropyl methycellulose phtalate (HP-MCP) and acrylic resins are most commonly used for coating tablets or granules for micro encapsulation. Preferably wet granulation is used to prepare the enteric-coated granules to avoid reactions between the active ingredient and the coating (Lin, S. Y. and Kawashima, Y. 1987, Pharmaceutical Res. 4:70-74). A solvent evaporation method can also be used. The solvent evaporation method was used to encapsulate insulin administered to diabetic rats to maintain blood glucose concentration (Lin, S. Y. et al., 1986, Biomater, Medicine Device, Artificial organ 13:187-201 and Lin, S. Y. et al., 1988, Biochemical Artificial Cells Artificial Organ 16:815-828). It was also used to encapsulate biological materials of high molecular weight such as vial antigen and concanavalin A (Maharaj, I. Et al. 1984, J. Phamac. Sci. 73:39-42).

For buccal administration, the pharmaceutical composition of the present invention may take the form of tablets or lozenges formulated in conventional manner.

For rectal administration propositories can be used as is well known in the art.

For administration by inhalation, a T2-RNase or a polynucleotide encoding same for use according to the present invention is conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of a T2-RNase or a polynucleotide encoding same and a suitable powder base such as lactose or starch.

The pharmaceutical composition of the present invention may also be formulated for parenteral administration, e.g., by bolus injection or continuos infusion. A composition for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of a T2-RNase or a polynucleotide encoding same may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of a T2-RNase or a polynucleotide encoding same to allow for the preparation of highly concentrated solutions.

Alternatively, a T2-RNase or a polynucleotide encoding same may be in a powder form for constitution with a suitable vehicle, e.g., sterile, pyrogen-free water, before use.

The pharmaceutical composition of the present invention may also be formulated in rectal compositions such as suppositories or retention enemas, using, e.g., conventional suppository bases such as cocoa butter or other glycerides.

In addition, a cancer or tumor present in a body cavity, such as in the eye, gastrointestinal tract, genitourinary tract (e.g., the urinary bladder), pulmonary and bronchial system and the like, can receive a physiologically appropriate composition (e.g., a solution such as a saline or phosphate buffer, a suspension, or an emulsion, which is sterile) containing an effective amount of a T2-RNase or a polynucleotide encoding same via direct injection with a needle or via a catheter or other delivery tube placed into the cancer or tumor afflicted hollow organ. Any effective imaging device such as X-ray, sonogram, or fiber optic visualization system may be used to locate the target tissue and guide the needle or catheter tube in proximity thereto.

The pharmaceutical composition of the present invention can also be delivered by osmotic micro pumps. The osmotic micro pumps are implanted into one of the body cavities and the drug is constantly released onto the tissue to be treated. This method is particularly advantageous when an immune response to the pharmaceutical composition is experienced. This method has been employed for ONCONASE (Vasandani V. M., et al., 1996, Cancer Res. 15; 56(18):4180-6).

Alternatively and according to another preferred embodiment of the present invention, the pharmaceutically acceptable carrier includes a delivery vehicle capable of delivering a T2-RNase or a polynucleotide encoding same to the mammalian cell of the subject.

Numerous delivery vehicles and methods are known in the art for targeting proteins or nucleic acids into or onto tumors or cancer cells. For example, liposomes are artificial membrane vesicles that are available to deliver proteins or nucleic acids into target cells (Newton, A. C. and Huestis, W. H., Biochemistry, 1988, 27:4655-4659; Tanswell, A. K. et al., 1990, Biochmica et Biophysica Acta, 1044:269-274; and Ceccoll, J. et al., Journal of Investigative Dermatology, 1989, 93:190-194). Thus, a T2-RNase or a polynucleotide encoding same can be encapsulated at high efficiency with liposome vesicles and delivered into mammalian cells. In addition, the T2-RNase protein or nucleic acid can also be delivered to target tumor or cancer cells via micelles as described in, for example, U.S. Pat. No. 5,925,628 to Lee, which is incorporated herein by reference.

Liposome or micelle encapsulated T2-RNase or a polynucleotide encoding same may be administered topically, intraocularly, parenterally, intranasally, intratracheally, intrabronchially, intramuscularly, subcutaneously or by any other effective means at a dose efficacious to treat the abnormally proliferating cells of the target tissue. The liposomes may be administered in any physiologically appropriate composition containing an effective amount of encapsulated T2-RNase or a polynucleotide encoding same.

Alternatively and according to another preferred embodiment of the present invention the delivery vehicle can be, but it is not limited to, an antibody or a ligand capable of binding a specific cell surface receptor or marker. An antibody or ligand can be directly linked to a T2-RNase protein or nucleic acid via a suitable linker, or alternatively such an antibody or ligand can be provided on the surface of a liposome encapsulating a T2-RNase or a polynucleotide encoding same.

For example, a T2-RNase or a polynucleotide encoding same can be fused with specific membranal protein antibodies or ligands for targeting to specific tissues or cells as previously described in the art. It will be appreciated in this respect that fusion of RNase A of the ribonuclease A superfamily with antibodies to the transferrin receptor or to the T cell antigen CD5 lead to inhibition of protein synthesis in tumor cells carrying a specific receptor for each of the above toxins (Rybak, M. et al., 1991, J. Biol. Chem. 266:21202-21207 and Newton D L, et al., 1997, Protein Eng. 10(4):463-70).

Pharmaceutical compositions suitable for use in context of the present invention include compositions wherein the active ingredients are contained in an amount effective to achieve the intended purpose. More specifically, a therapeutically effective amount means an amount of the active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

Toxicity and therapeutic efficacy of the active ingredients described herein can be determined by standard pharmaceutical procedures in cell cultures or experimental animals, e.g., by determining the $IC_{50}$ and the $LD_{50}$ (lethal dose causing death in 50% of the tested animals) for a subject active ingredient. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

While reducing the present invention to practice, it was surprisingly uncovered that administration of the T2 RNase having an actin binding activity has a synergistic effect on the anti-tumor efficacy of the TAXOL treatment (Example 15, FIG. 46). Thus, the T2 RNase having an actin binding activity or polynucleotide encoding same of the present invention can be used to treat diseases or conditions associated with aberrant cellular motility alone or in combination with other established or experimental therapeutic regimen for such disorders. Thus, according to the present invention there are provided methods of enhancing therapeutic treatment of a cancer. The methods are effected by administering to a subject in need thereof, in combination with the therapeutic treatment, a ribonuclease of the T2 family having an actin binding activity, or a polynucleotide encoding and capable of expressing in vivo the ribonuclease of the T2 family. It will be appreciated that such synergistic activity of T2 RNase treatment with additional therapeutic methods or compositions has the potential to significantly reduce the effective clinical doses of such treatments, thereby reducing the often devastating negative side effects and high cost of the treatment.

Therapeutic regimen for treatment of cancer suitable for combination with the T2 RNase of the present invention or polynucleotide encoding same include, but are not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy to and photon beam radiosurgical therapy.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Anti-inflammatory drugs that can be administered in combination with the T2 RNase having an actin binding activity or polynucleotide encoding same of the present invention include but are not limited to Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; to Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

As has already been mentioned hereinabove, according to an aspect of the present invention, the active ingredient of the pharmaceutical composition is a polynucleotide encoding a T2-RNase.

According to this aspect of the present invention the polynucleotide is introduced into the mammalian cell along with a pharmaceutically acceptable carrier, which introduction results in a genetic modification of this cell, enabling the expression of a T2-RNase therein.

As used herein in the specification and in the claims section below, the term "genetic modification" refers to a process of inserting nucleic acids into cells. The insertion may, for example, be effected by viral infection, injection, transfection, particle bombardment or any other means effective in introducing nucleic acids into cells, some of which are further detailed hereinbelow. Following the genetic modification the nucleic acid is either integrated in all or part, to the cell's genome (DNA), or remains external to the cell's genome, thereby providing stably modified or to transiently modified cells.

As such, the pharmaceutical composition according to this aspect of the present invention is usable for gene therapy.

As used herein the phrases "gene therapy" or "genetic therapy" are used interchangeably and refer to a method of therapy in which a stable or transient genetic modification of a proliferative cell(s) such as a cancer cell, leads to the inhibition of proliferation of this cell.

Any one of the polynucleotides identified in Table 3 by its Gene Bank accession number can be employed according to the present invention as a polynucleotide encoding a T2-RNase. In addition, polynucleotides 40% or more homologous and/or hybridizing under mild and/or stringent hybridization conditions with the listed polynucleotides can also be employed as a polynucleotide encoding a T2-RNase, provided that the protein encoded thereby is characterized as a T2-RNase and exhibits the desired activities. Furthermore, it will be appreciated that portions, mutants chimeras or alleles of such polynucleotides can also be employed as a polynucleotide encoding a T2-RNase according to the present invention, again, provided that such portions, mutants chimeras or alleles of such polynucleotides encode a T2-RNase which exhibits the desired activities.

Isolation of novel polynucleotides encoding T2-RNases is also envisaged. Such isolation can be effected using methodologies well known in the art such as, but not limited to, library screening, hybridization, PCR amplification, labeled primers, labeled degenerated primers. Both genomic and cDNA polynucleotides can thus be employed.

A polynucleotide according to the present invention can be fused, in frame, to any other protein encoding polypeptide to encode for a fused protein using methods well known in the art. For example the polypeptide can be fused to a leader sequence or a signal peptide for secretion. Similarly a T2-RNase protein can be fused (conjugated) to other proteins using methods well known in the art. Many methods are known in the art to conjugate or fuse (couple) molecules of different types, including proteins. These methods can be used according to the present invention to couple a T2-RNase to other molecules such as ligands or antibodies to thereby assist in targeting and binding of the T2-RNase to specific cell types. Any pair of proteins can be conjugated or fused together using any conjugation method known to one skilled in the art. The proteins can be conjugated using a 3-(2-pyridyldithio)propionic acid Nhydroxysuccinimide ester (also called N-succinimidyl 3-(2pyridyldithio) propionate) ("SDPD") (Sigma, Cat. No. P-3415), a gluteraldehyde conjugation procedure or a carbodiimide conjugation procedure.

According to a preferred embodiment of the present invention, the polynucleotide includes one or more segments harboring transcription control sequences operatively linked to the T2-RNase encoding sequence. Such transcription control sequences can include, but are not limited to, promoters and enhancers as further detailed hereinbelow. These transcriptional control sequences are typically operatively linked upstream to the coding region and function in regulating the transcription and/or translation thereof.

According to another preferred embodiment of the present invention the polynucleotide encoding a T2-RNase is included within a eukaryotic expression vector. The phrase "expression vector" refers to a nucleic acid sequence which includes a sequence encoding a T2-RNase and transcriptional control sequences and which is capable of expressing a T2-RNase within a mammalian cell.

Numerous methods for the insertion of DNA fragments into a vector, for the purposes of mammalian gene expression are known in the art and may be used to construct a T2-RNase encoding gene expression vector including appropriate transcriptional/translational control sequences and the desired T2-RNase polynucleotide sequences. These methods may include in vitro DNA recombinant and synthetic techniques and in vivo genetic recombination. Expression of a polynucleotide encoding a T2-RNase may be regulated by transcription control sequences so that a T2-RNase is expressed in a host cell infected or transfected with the recombinant DNA molecule. For example, expression of a T2-RNase may be controlled by any promoter/enhancer element known in the art. The promoter activation may be tissue specific or inducible by a metabolic product or administered substance.

Promoters/enhancers which may be used to control T2-RNase expression within target tissues or cells include, but are not limited to, the native RB promoter, the cytomegalovirus (CMV) promoter/enhancer (Karasuyama, H., et al., 1989, J. Exp. Med., 169:13), the human β-actin promoter (Gunning, P., et al., 1987, Proc. Natl. Acad. Sci. USA, 84:4831-4835), the glucocorticoid-inducible promoter present in the mouse mammary tumor virus long terminal repeat (HHTV LTR) (Klessig, D. F., et al., 1984, Mol. Cell. Biol., 4:1354-1362), the long terminal repeat sequences of Holoney murine leukemia virus (MULV LTR) (Weiss, R., et al., 1985, RNA Tumor Viruses, Cold Spring Harbor Laboratory, Cold Spring Harbor, N.Y.), the SV40 early region promoter (Bemoist and Chambon, 1981, Nature 290:304-310), the promoter contained in the 3' long terminal repeat of Rous sarcoma virus (RSV) (Yamamoto et al., 1980, Cell 22:787-797), the herpes simplex virus (HSV) thymidine kinase promoter/enhancer (Wagner et al., 1981, Proc. Natl. Acad. Sci. U.S.A. 78:1441-1445), the regulatory sequences of the metallothionein gene (Brinster et al., 1982, Nature 296:39-42), the adenovirus promoter (Yamada et al., 1985, Proc. Natl. Acad. Sci. U.S.A. 82(11):3567-71), and the herpes simplex virus LAT promoter (Wolfe, J. H., et al., 1992, Nature Genetics, 1:379-384).

Expression vectors compatible with mammalian host cells for use in genetic therapy of tumor or cancer cells, include, but are not limited to, plasmids, retroviral vectors, adenovirus vectors, herpes viral vectors, and non-replicative avipox viruses, as disclosed, for example, by U.S. Pat. No. 5,174, 993, which is incorporated herein by reference.

Several methods can be used to deliver the expression vector according to this aspect of the present invention to the target mammalian cell(s).

For example, a suitable pharmaceutically acceptable carrier such as a physiologically appropriate solution, and which contains an effective amount of an expression vector can be administered topically, intraocularly, parenterally, orally, intranasally, intravenously, intramuscularly, subcutaneously or by any other effective means.

A physiologically appropriate solution containing an effective amount of an expression vector can be administered systemically into the blood circulation to treat a cancer or tumor which cannot be directly reached or anatomically isolated.

For treating tumor masses a physiologically appropriate solution containing an effective amount of an expression vector can be directly injected, via a needle, into a target tumor mass in amounts effective to treat the tumor cells of the target tumor to mass.

Alternatively, a cancer or tumor present in a body cavity such as in the eye, gastrointestinal tract, genitourinary tract (e.g., the urinary bladder), pulmonary and bronchial system and the like can receive a physiologically appropriate composition (e.g., a solution such as a saline or phosphate buffer, which is sterile except for the expression vector) containing an effective amount of an expression vector via direct injection with a needle or via a catheter or other delivery tube placed into the cancer or tumor afflicted hollow organ. Any effective imaging device such as X-ray, sonogram, or fiber optic visualization system may be used to locate the target tissue and guide the needle or catheter tube.

It will be appreciated that since a "naked" expression vector can be actively taken up by mammalian cell, uptake and targeted delivery is enhanced if the expression vector is appropriately packaged or encapsulated.

Thus, according to another preferred embodiment of the present invention the pharmaceutically acceptable carrier includes a delivery vehicle suitable for the delivery of the expression vector into mammalian cells in a targeted manner.

A viral expression vector may be introduced by a delivery vehicle into a target cell in an expressible form by infection or transduction. Such a delivery vehicle includes, but is not limited to, a retrovirus, an adenovirus, a herpes virus and an avipox virus. A delivery vehicle able to introduce the vector construct into a target cell and able to express T2-RNase therein in cell proliferation-inhibiting amounts can be administered by any effective method described hereinabove.

Alternatively, such a delivery vehicle can include, but is not limited to, a liposome, a micelle, an antibody or a ligand as previously described hereinabove.

It will be appreciated that the polynucleotides herein described can be used in the preparation of a medicament useful in inhibiting the proliferation of a mammalian cell of a mammal, by mixing the polynucleotide with an appropriate pharmaceutically acceptable carrier.

As already mentioned hereinabove, polynucleotides encoding a T2-RNase can be obtained by a variety of methods, including, but not limited to, polymerase chain reaction (PCR) amplification of genomic or cDNA libraries screening using T2-RNase specific primers, using reverse transcription PCR along with T2-RNase specific primers to amplify mRNA isolated from organisms known to express T2-RNases, or directly isolating DNA sequences coding for a T2-RNase from the appropriate organisms. It will be appreciated in this case that the above mentioned methods can also be used to isolate or generate any of the active forms of a T2-RNase described hereinabove.

The purified polynucleotide can then be inserted into appropriate expression vectors or provided with the appropriate transcriptional control sequences and prepared as described hereinabove.

As is further exemplified in the Examples section that follows and mentioned hereinabove, an assay for determining the effects of a specific T2-RNase or a polynucleotide encoding same is also provided in accordance with the teachings to the present invention. Such an assay is effected, for example, by exposing proliferating cells to a T2-RNase and following their proliferative behavior over time as compared to control, untreated cells. This assay can be employed not only for selecting for the most potent T2-RNase for any specific application, but also for establishing dose response, which can be translated into initial treatment dosage in in vivo experiments or during treatment of a subject, all as is further exemplified herein for RNase B1 of the T2 family. It will be appreciated that this assay can also be used to determine the anti-proliferative active site or portion or a T2-RNase, or to determine the activity of generated or isolated mutants which do not display ribonucleolytic activity.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well to known in the art and are provided for the convenience of the reader. All the information contained therein is incorporated herein by reference.

Example 1

Characterization of *Aspergillus niger* B1 Rnase and its Inhibitory Effect on Pollen Tube Growth in Fruit Trees

Materials and Methods

Preparation and Purification of *A. Niger* Extracellular RNase:

*Aspergillus niger* B1 (CMI CC 324626) was grown in liquid culture containing 1% (w/v) wheat flour and 0.05% (w/v) ammonium sulfate. The mixture was adjusted to pH 3.5 with hydrochloric acid and autoclaved. An inoculum of about $10^6$ spores was suspended in 100 ml of medium and incubated at 30° C. in an orbital shaker, at 200 rpm for 100 hours. The growth medium was passed through a 0.2-μm membrane and dialyzed three times against 10 volumes of 2 mM sodium acetate pH 6. Two liters of dialyzed solution were loaded onto a Fractogel EMD-TMAE 650 (M) 26/10 (Merck) column, equilibrated with 20 mM sodium acetate pH 6. Bound proteins were eluted with a 500-ml linear gradient of 0-1.0 M sodium chloride in the same buffer, using a fast protein liquid chromatography (FPLC) system (Pharmacia) with a flow rate of 5 ml·min$^{-1}$. The fractions exhibiting the highest RNase activity were pooled and dialyzed against 2 mM sodium acetate pH 6, and a 50-ml aliquot was loaded onto a MONO-Q 5/5 HR (Pharmacia) column, equilibrated with 20 mM sodium acetate pH 6. The elution was performed as with the EMD-TMAE column, except that only 10 ml of a 0-1.0 M salt gradient were used, at a flow rate of 1 ml·min$^{-1}$.

Proteins were monitored at 280 nm and measured according to Bradford (Bradford, M. M. 1976. Anal. Biochem. 72:248-245), using bovine serum albumin (BSA) as a standard. Different fractions were analyzed by a 12.5% sodium dodecyl sulfate-polyacrylamide gel electrophoresis (SDS-PAGE) (Laemmeli, U. K. 1970. Nature 227: 680-685). RNase activity was determined as previously described (Roiz and Shoseyov 1995, Int. J. Plant Sci. 156:37-41).

The purified RNase B1 was enzymatically deglycosylated according to the procedure described by Broothaerts et al. (Broothaerts, W. P. et al. 1991. Sex. Pant Reprod. 4:258-266). The enzyme was mixed with 0.5% (w/v) SDS and 5% (w/v) 13-mercapthoethanol and heated at 100° C. for 5 minutes. Once cooled, the reaction mixture was diluted 2.5-fold with a buffer containing 50 mM sodium phosphate pH 7.5, 25 mM EDTA, 1% (w/v) Triton X-100 and 0.02% (w/v) sodium azide. Peptide-N-glycosidase F (PNGase F, Boehringer-Mannheim) was added to a final concentration of 20 units·ml$^{-1}$ and incubation was performed overnight at 37° C. The sample was then mixed with sample application buffer, heated at 100° C. for 5 minutes, and analyzed by SDS-PAGE using a 12.5% gel.

RNase Assays:

The optimal conditions for RNase activity were determined according to a procedure modified from Brown and Ho (Brown, P. H. and Ho, T. H. D. 1986 Plant Physiol. 82:801-806), using a range of temperatures from 20-100° C. at 10° C. increments, and a range of pH's from 2.5-7 at 0.5 pH units increments, established using 50 and 12 mM phosphate-citrate buffers. Samples of 10 μl were each added to 490 μl of ice-cold buffer, containing 4 mg·ml$^{-1}$ yeast RNA (Sigma). Half of each sample was used as a blank by immediately adding a stop solution containing 50 μl of 0.75% (w/v) uranyl sulfate in 25% (w/v) perchloric acid. The remaining half was incubated for 10 minutes, following which a 50 μl of stop solution was added to each. Following centrifugation at 15,000×g for 5 minutes, the supernatant was diluted 20-fold with distilled water and the absorbance was determined at 260 nm. One unit of RNase activity was determined as the amount of enzyme releasing soluble nucleotides at a rate of one $A.U_{260\,nm}$ per min.

RNase B1 was visualized by an activity gel, as previously described (Roiz and Shoseyov, 1995, Int. J. Plant Scizzz. 156:37-41). An SDS gel containing RNase B1 was renatured by washing twice for 15 minutes each with 20 mM acetate buffer at pH 3.5 containing 25% (v/v) iso-propanol and then twice for 15 minutes each with buffer alone. The renatured gel containing the RNase B-1 was laid over a plate containing 0.1% RNA and 0.8% agarose in 20 mM acetate buffer and incubated at 37° C. for 30 minutes. The gel was then removed and the agarose plate was stained with 0.02% (w/v) toluidine blue in water to visualize RNase activity.

The Effect of RNase B1 on Pollen Tube Growth:

Peach cv. Almog pollen was germinated in vitro in liquid culture, as previously described (Roiz and Shoseyov, 1995, Int. J. Plant Sci. 156:37-41). Pollen grains were suspended in aliquots containing 100 μl of 15% (w/v) sucrose, 100 μg·ml$^{-1}$ boric acid, 200 μg ml$^{-1}$ magnesium sulfate, 200 μg·ml$^{-1}$ calcium nitrate and different concentrations of RNase B1. Following incubation overnight at 25° C. in a dark chamber, germination percentage was recorded. Pollen tube length was examined with an eyepiece micrometer.

The effect of RNase B1 treatment on pollen tube growth was also tested in vivo. Intact flowers of peach and in tangerine (*Citrus reticulata*, Blanco cv. Murcott) were sprayed at the early stages of anthesis with 100 units·ml$^{-1}$ RNase B1 in 20 mM citrate buffer at pH 3.5. In each species additional flowers at the same stage, on different branches, were sprayed with buffer alone or remained untreated as controls. Following exposure to open pollination for 48 hours, the styles were fixed in a 3:1 acetic acid to ethanol (by volume) for 24 hours, washed with distilled water and imbibed overnight in 8 M sodium hydroxide. Following thorough washing in distilled water, the styles were cut longitudinally, immersed each in a drop of 0.1% (w/v) aniline blue in 0.1 M potassium phosphate on a slide and carefully squashed with a cover glass. Pollen tubes were observed by epifluorescence microscopy (Olympus BX40 equipped with WIB cube).

The Effect of RNase B1 on Fruit Set:

Field experiments were done in nectarine (*Prunus persica* var. *Nectarina Fantasia*). Branches of 30-40 cm long, bearing approximately 10% open flowers, were sprayed with different concentrations of RNase B1 in 20 mM citrate buffer pH 3.5 and 0.025% triton-X 100. Untreated branches, and branches sprayed with only buffer and triton-X 100, served as controls. The branches were sprayed at 2- to 3-days intervals during the blooming period (14 days). A month later, the number of fruit per branch was examined. For viability test, seeds were cut longitudinally through the embryo and immersed in 1% 2,3,5-Triphenyl tetrazoluim chloride in water for 4 to hours at 20° C. in a dark room. Red staining indicated viable tissues.

Experimental Results

Purification and Characterization of RNase B1:

*A. niger* grown in liquid culture produced considerable amounts of extracellular RNase B1. A temperature of 60° C. and a pH of 3.5 were found optimal for RNase activity, and were adopted as the standard conditions for subsequent RNase assays.

RNase B1 purification included three steps (Table 4). In a first step a crude filtrate contained 1000 units·ml$^{-1}$ and 0.05 mg·ml$^{-1}$ protein was obtained. The crude filtrate was passed through an EMD-TMAE column and the pooled active fractions (FIG. 1, graph A) contained 0.1 mg·ml$^{-1}$ protein, with an RNase activity of 40,000 units·ml$^{-1}$. In the final step, the pooled fractions were passed through a MONO-Q column and the active RNase fraction was eluted (FIG. 1, graph B). This fraction contained a protein concentration of 1.05 µg·ml$^{-1}$ and RNase activity of 543,000 units·ml$^{-1}$. Two major protein bands, of 40 and 32 kDa, were observed following SDS-PAGE of the purified RNase B1 fraction (FIG. 2). An RNase activity gel showed active bands corresponding to the 32 and the 40 kDa proteins. When subjected to PNGase F, a single protein band appeared at 29 kDa. RNase activity was retained after PNGase digestion (not shown).

TABLE 4

| Purification step | Total units | Protein concentration (mg/ml) | Recovery (%) | Specific activity (units/mg protein) |
|---|---|---|---|---|
| Crude filtrate | 2,000,000 | 0.05 | 100 | 20,000 |
| EMD-TMAE column | 1,120,000 | 0.1 | 56 | 400,000 |
| MONO-Q column | 652,200 | 1.05 | 32.6 | 517,143 |

The Effect of RNase B1 on Pollen Tubes and Fruit Set:

In in vitro, experiments 75% of the control pollen grains germinated and the pollen tubes reached about 0.5 mm in length. Addition of RNase B1 to the growth medium reduced the percentage of germination and the length of the pollen tubes, in a dose responsive manner (FIG. 3). RNase B1 had a pronounced inhibitory effect, 50 units·ml$^{-1}$, representing 0.1 µg·ml$^{-1}$ protein, were lethal, whereas 125 µg·ml$^{-1}$ of BSA reduced only half of pollen germinability and tube growth.

In vivo, control pollen tubes of peach were observed growing through the stigmatic tissue directed into the style 48 hours after pollination (FIG. 4a). A similar effect was observed in styles treated with buffer only. In contrast, pollen grains germinated on stigmas treated with RNase B1 produced short pollen tubes, which appeared to lack any growth orientation, and failed to penetrate the stylar tissue (FIG. 4b). In tangerine only a small portion of the stigmatic tissue, the diameter of which was 2-3 mm, was captured by the view field of the microscope. Therefore, only few pollen tubes were observed, as shown in FIG. 5. However, the difference between the normal growth of the control pollen tubes (FIG. 5a) and the irregular growth of the RNase-treated pollen tubes (FIG. 5b), was clearly evident.

In nectarine cv. Fantasia, RNase B1 caused a reduction in fruit set (Table 5). In branches that remained untreated or sprayed with buffer with triton X-100, fruit set was 48.3% and 36.3%, respectively. It seemed that the low pH-buffer had some inhibitory effect on fruit set, however branches treated with 500 and 1000 units·ml$^{-1}$ of RNase B1 set 23.3% and 18.4% fruits, respectively, indicating a significant thinning effect of the RNase, in a dose dependent manner.

TABLE 5

| Treatment | Flowers (total number) | Fruit set (%) |
|---|---|---|
| Control untreated | 169 | 48.3 a* |
| Control buffer | 143 | 36.3 ab |
| 500 units/ml RNase B1 | 148 | 23.3 bc |
| 1000 units/ml RNase B1 | 106 | 18.4 c |

*values not sharing a common letter are significantly different at P = 0.05.

In RNase B1 treated branches many undeveloped fruitlets were observed. Viability tests showed that in the control flowers (either untreated or sprayed with buffer only), embryo tissues were stained red, (FIG. 6a), whereas the tissues of embryos developed in RNase-treated flowers, stained brown indicative of necrosis (FIG. 6b).

*Aspergillus niger* B1 extracellular RNase (RNase B1) was purified to to homogeneity. It was found to contain two isoforms of 32- and 40-kDa glycoproteins, sharing a 29-kDa protein core. The optimal RNase activity was observed at a temperature of 60° C. and a pH of 3.5. In peach (*Prunus persica* cv. Almog) and tangerine (*Citrus reticulata*, Blanco cv. Murcott) the enzyme inhibited pollen germination and tube growth in vitro as well as in vivo. In field experiments, the RNase caused a reduction in nectarine (*Prunus persica* var. *nectarina Fantasia*) fruit set and inhibited normal embryo development.

Example 2

Inhibition of Pollen Germination and Tube Growth by T2-RNase is Mediated Through Interaction with Actin The inhibition of pollen germination and tube growth by RNase is well recognized, yet the mechanism by which this enzyme interferes with the elongation process is still unclear. As such, this study set out to decipher the role of RNase B1 in interfering with the elongation process of pollen tubes.

Materials and Experimental Methods

The Effect of RNase B1 on Pollen Tubes Growth:

Anthers of lily (*Lilium grandiflorum* L. cv. Osnat) were let to dehisce for 24 hours at room temperature and than either used fresh or stored at –20° C. RNase B1 was produced and purified from *Aspergillus niger* growth medium filtrate as described in Example 1. Pollen was germinated in vitro in aqueous cultures of 100 µl each, containing 7% sucrose, 1.27 mM CaNO$_3$, 0.16 mM H$_3$BO$_3$, 1 mM K$_2$NO$_3$ and 3 mM KH$_2$PO$_4$ in water (Yokota and Shimmen 1994). Some cultures were supplemented with RNase B1 having 100 units/ml of RNase activity to a final protein concentration of 16 µg/ml. Additional cultures were supplemented with RNase that was previously boiled for 30 minutes which produced the loss of 50% of activity, or with autoclaved RNase lacking any catalytic activity. Following 2 hours of incubation at 25° C. in the dark, pollen tube length was measured under the microscope eyepiece micrometer. The pollen tubes were stained with IKI (0.3% I$_2$ and 1.5% KI in water) to detect starch bodies.

Actively extending 1-hour pollen tubes were transferred to glass cells on the microscope stage. The pollen tubes growth pattern and organelle movement were video recorded as modified from Heslop-Harrison and Heslop-Harrison (Heslop-Harrison, J. and Heslop-Harrison, Y. 1990. Sex Plant Reprod. 3:187-194), using Applitec MSV-800 video presenter. Images were captured at 0.8 frames/sec for 8 seconds by Scion LG-3 frame grabber and then digitized and integrated by NIH image software. The photographs were processed using Adobe Photoshop (Adobe Systems Inc., Mountain View, Calif.) and Power-Point (Microsoft Co.) softwares.

The Effect of RNase on Pollen Tube Actin Filaments:

Pollen was germinated in vitro in aqueous cultures with or without RNase.

Following incubation overnight, the pollen tubes were gently pelleted and the growth medium was replaced with 10$^{-6}$ M tetramethylrhodamine B isothiocyanate (TRITC)-labeled phalloidin (Sigma) in PBST buffer (150 mM NaCl, 3 mM KCl, 10 mM $Na_2HPO_4$, 2 mM $KH_2PO_4$ and 0.02% Tween-20). For in vivo observations, lily cv. Stargazer flowers were emasculated at the onset of anthesis and 0.5 ml of a growth medium containing 100 units/ml RNase were injected through the stigma into the stylar canal. Flowers into which growth medium without RNase was injected were used as a control. The liquids were absorbed into the stylar tissue for 5 hours at 25° C., following which the stigmas were hand-pollinated by lily cv. Osnat pollen. Following 48 hours of incubation at 25÷C, each pistil was cut longitudinally and the pollen tubes were carefully excised and removed into TRITC-TBST solution and incubated for 1 hour. The incision at the stigma did not affect the pollen tubes, since their vital protoplasts were located at the distal part, protected by callose plugs. In both the in vitro and in vivo experiments the stained pollen tubes were rinsed in TBS (TBST lacking Tween-20), placed on a glass slide and observed with an epifluorescent light microscope (Olympus BX40 equipped with USH-102D mercury to lamp).

Binding of Actin to RNase B1:

The interaction between RNase B1 and actin was quantified as modified from Simm (Simm, F. C. et al., 1987. Eur. J. Biochem. 166:49-54). Rabbit muscle globu(G-) actin (Sigma Co.) was polymerized to filamentous (F-) actin in Buffer F (10 mM Tris pH 8, 0.1 mM ATP, 0.2 mM $CaCl_2$, 0.1 M KCL and 2 mM $MgCl_2$) for 30 minutes at room temperature. Samples of 50 µl containing each 30 µM F-actin were incubated overnight at 4° C. with 1-33 µM RNase B1. As a control, each concentration of RNase was incubated with buffer F alone. The samples were centrifuged at 15,000 g for 40 minutes and RNase activity of the supernatant was determined (Roiz, L., Goren, R. and Shoseyov, 0.1995, Physiol. Plant. 94:585-590.).

Immunogold Silver Staining of RNase B1 on Pollen Tubes:

Immunogold silver stain (IGSS) was used to detect RNase attachment to lily pollen tubes. Polyclonal antibodies were raised against RNase B1 in rabbit (Aminolab). In vitro 2-hours lily pollen tubes were fixed overnight in 2.5% gluteraldehyde in PBST at 4° C. The pollen tubes were washed for 1 hour in PBST, blocked for 1 hour in PBST containing 1% BSA and 2% skim-milk and incubated for 1 hour in anti-RNase B1, diluted 1:500 in PBST. Rabbit pre-immune serum (PIS) was used as control. The pollen tubes were washed three times, 10 minutes each, in PBST and then incubated for 1 hour in goat anti-rabbit IgG conjugated with 5-nm gold particles, diluted 1:100 in PBST. Following two 10 minutes-washes in PBST and one 10 minutes-wash in water, a silver-stain kit (BioCell Research Laboratories) was used for the final development of the reaction. The pollen tubes were soaked in the combined kit solutions for 10-15 minutes, washed in excess distilled water and observed under a light microscope (Olympus BX40).

Experimental Results

A control sample of lily pollen tubes, germinated in vitro in a growth medium without RNase, reached about 300 µm in length (FIG. 7). Cultures that were treated with RNase under the same conditions, reached only 160 µm in length. Boiling or autoclaving the RNase yielded pollen tubes of 130 and 170 µm in length, respectively. The differences between the three RNase-treated groups of pollen tubes were deemed to insignificant.

Starch-staining showed that amylioplasts of the control sample were observed spreading along the pollen tube, except at the tip zone (FIG. 8a). On the other hand, in RNase-treated pollen tubes IKI-stained bodies accumulated at the tip zone (FIG. 8b).

The integrated video images of actively extending pollen tubes displayed the cytoplasmic flow lines (FIGS. 9a and 9b). In the control sample a continuous longitudinal movement characteristic of normal pollen tube development was most common, as was acropetal flow at the tube periphery and basipetal flow at the center, forming an "inverse fountain" pattern beneath the tip zone (FIG. 9a). The tip zone itself was occupied by much smaller bodies, mainly P-particles, the movement pattern of which was hardly observed. In RNase-inhibited pollen tubes the disruption of actin filament assembly is evident. The stunted growth tip appeared swollen, with well-visible starch and lipid particles reaching the tip zone (FIG. 9b). No continuous movement could be detected, but instead extended irregular images indicated cytoplasmic bodies rotating randomly.

The effect of RNase on the actin filaments distribution was examined in 1-hour in vitro and 48-hours in vivo pollen tubes. The in vivo pollen tubes reached about 3-4 cm long, and their TRITC-phalloidin staining was more intensive than in the in vitro tubes. However, the mode of the RNase effect was similar in both experiments. In the control, actin microfilaments were assembled longitudinally along the tube axis, forming a fine network in the tip zone (FIG. 10a). On the other hand, in RNase-treated pollen tubes masses of actin were accumulated at the tip cell wall (FIG. 10b).

The interaction between RNase B1 and actin was quantified using Scatchard analysis. In the actin-RNase B1 binding experiment a regression line, intersecting with the abscissa at 0.45 (FIG. 11) indicated that the RNase:actin molar ratio was 0.45, implying that two actin molecules bind to each RNase molecule.

Pollen germinated in the presence of RNase B1 were prepared for light microscopy and the location of RNase was determined by IGSS, using anti-RNase antibodies (FIGS. 12a-c). In pollen tubes grown without RNase (FIG. 12a) or with to RNase but treated with PIS (FIG. 12b), the cell wall external surface was devoid of silver staining. On the other hand, in pollen tube treated with RNase B1, a clear immunogold silver stain appeared, accumulating upon the tip zone (FIG. 12c).

In this study Lily (*Lilium grandiflorum*) pollen germination and tube elongation were specifically inhibited by *A. niger* RNase B1. Boiled or autoclaved RNase, lacking most of the original catalytic activity, showed a similar inhibitory effect. The results demonstrate that *A. niger* RNase is a protein having an actin-binding activity clearly related to the inhibitory effect of the T2 RNase on pollen tube elongation. This actin binding activity, which is unrelated to the catalytic activity of RNase B1, deforms the pollen tube actin filaments arrangement to thereby disrupt cytoplasmic streaming, cell motility and growth.

Example 3

The Effect of RNase B1 on Human Colon Cancer Cells

Since the actin binding activity uncovered for RNase B-1 in pollen tubes hinted at a possible cytotoxic activity it was decided to examine the cytotoxic effect of RNase B1 on human colon cancer cells.

Materials and Experimental Methods and Results

Cell Culture:

All the experiments were performed in vitro. Human colon adenocarcinoma (HT29) cells were grown in DMEM medium (Biological Industries, Bet Haemek), supplemented with 10% fetal calf serum, 1% glutamine and 10% Antibiotic-Antimicotic solution (Biolab). The cells were incubated at 37° C. in a humidified atmosphere containing 5% $CO_2$. RNase B1 solutions were made in PBS buffer, pH 6.8.

Preliminary Cell Viability Assay:

Cells were incubated with 50-ml flasks. Each flask contained $2 \times 10^5$ cells in 7 ml medium, in the absence or presence of different concentrations ($10^{-8}$-$10^{-6}$ M) of RNase B1. The cells were grown for 48 hours or 72 hours, and then viable and non-viable cells were differentially counted using trypan blue staining.

In all treatments the total number of cells grown for 72 hours ($55$-$60 \times 10^5$) exceeded to by about twofold the number of cells obtained after 48 hours culture ($25$-$30 \times 10^5$) (FIG. 13a). The presence of RNase B1 in the growth medium did not have a significant effect on cell growth. However, a small but significance effect of the RNase B1 on the number of dead cells was found at both 48 hours and 72 hours of incubation (FIG. 13b).

Clonogenicity Assay I:

The long-term survival of tumor cells is characterized by their ability to divide and produce clones. Cells were preincubated for 48 hours in growth medium containing $10^{-6}$ M RNase B1, then trypsinized, washed and resuspended in growth medium lacking RNase B1. Prior to plating into 96-well microtiter plates, the cells were diluted to serial 5-fold dilutions ranging between 50-to-$10^5$ cells in each well (200 ml). The plates were incubated for 14 days in the conditions described above, without adding fresh growth medium following which the colonies were fixed and stained with methylene blue. The clonogenic cells in each well were numbered following clones visualization. Control cells were treated as above, but preincubated during the first 48 hours in medium lacking RNase B1.

In both treatments a similar number of colonies was observed in wells in which 100 cells were plated (FIG. 14). The cytotoxic effect of the RNase B1 appeared in wells containing higher densities of cells. In wells plated with 500 cells each, the control and the RNase B1-treated cells produced 180 and 100 colonies per well, respectively. Furthermore, in wells plated with 1000 cells each the RNase B1-treated cells formed about 250 colonies per well, whereas the control cells formed numerous colonies that fused to a continuous layer, thus could not be counted and illustrated in FIG. 14. Cells plated at higher densities did not survive the culture without changing media.

Clonogenicity Assay II:

The ability of the tumor cells to proliferate and to colonize was examined in short vs. continuous exposure to RNase B1. The experiment was performed as described in Clonogenicity assay I using (i) control cells, (ii) cells preincubated with medium containing $10^{-6}$ M RNase B1 and then allowed to colonize in RNase B1-free growth medium, and (iii) cells preincubated as in (ii) and then incubated during the colonization assay in growth medium containing $10^{-6}$ M RNase B1. In these experiments the initial densities ranged between 250-1000 cells per well and the colonization period was 7 days.

The shorter period of incubation used in this experiment (7 days) compared to a 14 day preincubation resulted in non defused colonies, which could be distinguished even in wells containing high densities of cells. In all densities, 48 hours of preincubation in RNase B1 led to a reduction of 20-30% in the ability of the cells to colonize, compared to the control (FIG. 15). However in each density a continuous exposure to RNase B1 led to a dramatic reduction of 90% in clonogenicity. FIGS. 16a-c Show that the continuous RNase B1-treated cells (FIG. 16c) were smaller and less stainable than the cells that were preincubated for 48 hours in RNase B1 (FIG. 16b) or the control cells (FIG. 16a). This result indicate that RNase B1 affected the colonies growth rate.

Thus as is clearly shown from the results presented herein A. niger RNase B1 has a clear cytotoxic effect on human adenocarcinoma HT29 cancer cells. The cytotoxic effect of RNase B1 is expressed via reduction of cell clonogenicity, rather than reduction of cell viability. It is possible that the RNase B1 has a long-term effect on the tumor cells. The RNase B1 causes a reduction in the colonies growth rate compared to the control, indicating that it may affect the ability of the cells to proliferate.

Example 4

The In Vivo Effect of RNase B1 on Tumor Development in a Rat Model

For further studying the anti-cancer effect of RNase B1, an in vivo experiment was conducted in rats.

Materials and Experimental Methods

Charles-River derived 4-weeks old male rats were divided into groups of 6. In some groups, the rats were induced to develop colon cancer by five weekly injections of Dimethylhydrazine (DMH). In this experiment, two modes of RNase B1 administration were examined. RNase B1 was applied directly into the colon by osmotic micro-pumps, or given orally using enterocoated microcapsules. The full set of treatments each rats group received is described by the scheme of FIG. 1. During the experiment, the rats were weighted weekly to monitor the effect of DMH and/or RNase B1 on their growth rate. In groups treated with RNase B1 feces was collected weekly from each cage and dried at 60° C. A sample of 250 mg dry feces was grounded and re-dissolved in phosphate buffer saline (PBS). Following centrifugation, RNase activity in the upper solution was examined as described in Roiz et al. (Roiz, L. et al., J. Amer. Soc. Hort. Sci. 125(1):9-14. 2000).

Administration of RNase B1 to the Colon Via Osmotic Micro-Pumps:

RNase B1 was loaded into osmotic micro-pumps (ALZET). The pumps were implanted subcutaneously into the rats abdomen. The osmotic pumps allowed a constant release of RNase B1 directly into the colon via a catheter, at a calculated concentration of $10^{-6}$ M in the colon for at least 6 weeks, assuming that the rat colon is about 4 ml in volume. Rats were treated as follows: Rats of one group were implanted with pumps containing "live" RNase B1 (RNase B1), having full RNase activity. Rats of a second group were implanted with pumps containing autoclave-inactivated RNase B1 (1-RNase B1), lacking any RNase activity. Whereas, rats of a third group were implanted with pumps containing PBS, which was used as the RNase B1 vehicle in the first two groups, and served as controls.

To examine a possible preventive effect of RNase B1, selected DMH-treated rats received RNase B1-9 weeks after the first DMH injection. Then, the rats were sacrificed and their colons excised and washed with PBS and then with PBS containing 0.1 M dithiothreitol (DTT). The colons were thereafter opened longitudinally and fixed for at least 1 hour in 4% formaldehyde in PBS over a filter paper. Following staining with 0.025% methylene blue in PBS, the colon mucosa was observed via a microscope under low magnification for aberrant crypt foci (ACF). ACF were counted in the distal (5 cm) colon.

To examine a therapeutic effect of RNase B1, the rest of the rats received RNase B1 from 12 to 17 weeks after first DMH injection. The colons were excised and fixed as described above and the tumors counted and measured. For histopathological examinations, each tumor was embedded in paraffin. Thin (10 μm) sections were stained and the degree of malignancy was evaluated.

Oral Administration of RNase B1:

Preparation of Microcapsules:

Microcapsules were prepared with a modified procedure described by Lin et al. (Lin J. J., et al., 1994, Biochem. Biophys. Res. Commun. 14; 204(1):156-62). A mixture of 0.6 grams lyophilized RNase B1 and 2.4 grams glucose was well powdered by a mortar and pestle. The fine powder was poured into a 1 L beaker containing 200 ml liquid paraffin and 2 ml Span-80 and stirred at 600 rpm for 20 min. Acetone-ethanol-cellulose acetate phthalate (CAP) solution was carefully added to the above stirring mixture (3.2 grams CAP in 40 ml of 9:1 acetone: 95% ethanol) and let stir for further 2 h in a hood, to remove traces of acetone. The microcapsules were hardened by adding 30 ml ether and dried on filter paper using Buchner funnel and traces of liquid paraffin were removed by two additional washes with 30 ml ether. The microcapsules were then let dry overnight and pass through a fine mesh. Most microcapsules were between 200 and 500 μm.

In a preliminary experiment (FIG. 18), CAP microcapsules were found insoluble in acidic pH, representing the stomach environment. However, after 1 hour in alkaline pH maximum RNase activity was reached, indicating that the microcapsules could easily release their content in the intestines.

Oral Administration of the RNase B1 Microcapsules:

The microcapsules containing RNase B1 or glucose as placebo, were mixes with ground Purina chows. Each RNase B1-treated rat received a daily dose of 1.6 mg RNase B1, to gain a final concentration of $10^{-5}$ M in the colon. The experimental details for oral administration were as described above for the micro-pumps administration, except for a delayed termination (11 weeks) while evaluating the preventive effect of RNase B1 (FIG. 17).

Experimental Results

The Effect of the Different Treatments on Rat Growth Rate:

The rats initial weight was about 200 grams. The experiment ended at different time for each treatment, as described above. Generally, the rats reached a final body weight of about 400-500 grams, with no significant differences between the different treatments (FIG. 19a-d). However, DMH-treated groups showed a slight decrease in to body weight comparing to RNase B1-treated groups, in the presence or absence of DMH.

RNase Activity in Rat Feces:

FIGS. 20a-c show changes in RNase activity in feces of rats implanted with osmotic pump containing RNase B1, I-RNase B1 or PBS in a preventive mode (FIG. 1) during 8 weeks. In rats treated with RNase B1 (FIG. 20a) RNase activity in feces was 5-fold higher than in rats treated with I-RNase B1 (FIG. 20b) or with PBS (FIG. 20c). This activity was maintained high for 5 weeks and then decreased gradually, as the reservoir of RNase B1 in the pumps exhausted. A basal endogenous RNase activity was detected in feces of the two latter groups.

Similar pattern was observed in rats fed with microencapsulated RNase B1, but an 8-fold higher RNase activity was detected as is compared to rats fed with microcapsules containing glucose only (FIG. 21). In this experiment, the gradually decrease in RNase activity may be explained as a result of increase in the rats body weight and as a consequence, the colonic volume.

The Effect of RNase B1 as a Preventive Agent:

The pump-implanted rats were sacrificed after 8 weeks, since infection at the pump sites was observed. At this stage only ACF were apparent. ACF are surrogated biomarkers of carcinogenic changes in the rat colon during the initiation phase of carcinogenesis. Goblet cells in cryptae become larger and were intensively stained comparing to the normal mucosal cells. ACF counts were dramatically reduced due to RNase B1 or I-RNase B1 treatments (FIG. 22). No damaging effect on colon mucosa was observed in rats treated with RNase B1 or I-RNase B1 in the absence of DMH.

In rats fed with microencapsulated RNase B1, the experiment continued for 11 weeks following the first DMH administration. At that time, both tumors and ACF were present. RNase B1 caused a reduction in the number of tumors per colon FIG. 23a), in tumor size (FIG. 23b) as well as in the number of ACFs (FIG. 23c) as is compared to control.

Figure 24A:
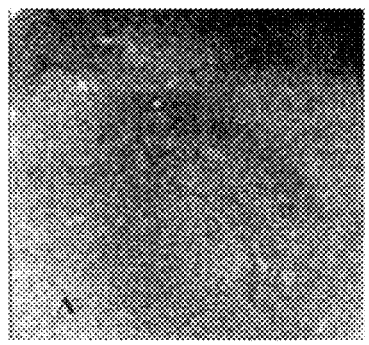
Figure 24B:
Figure 24C:
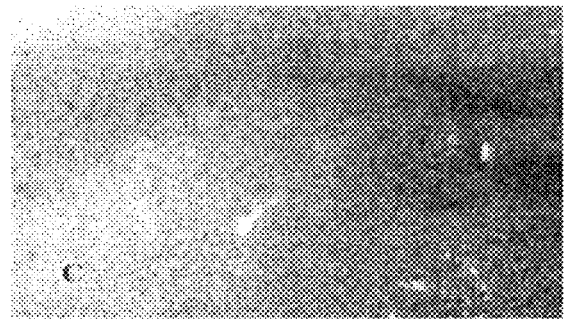
Figure 24D:
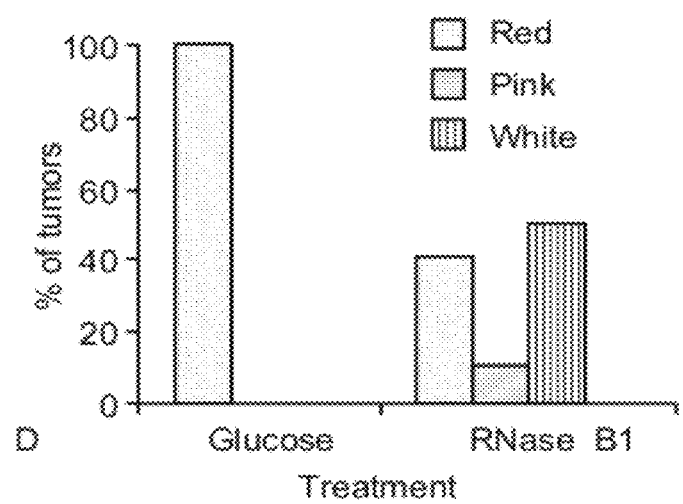

In addition, a color diversity of colon tumors was observed; red tumors that had intensive blood supply (FIG. 24a), white tumors almost devoid of blood vessels (FIG. 24b), and "pink" tumors with only few blood vessels (FIG. 24c). In glucose-treated rats all the tumors were red. On the other hand, in RNase B1-treated rats a significant reduction in the number of reddish tumors was observed (FIG. 24d); 10% and 50% of the tumors were pink and white, respectively. These results clearly indicate an anti-angiogenic effect of RNase B1.

Tumors could also be distinguished by histopathological parameters, as benign or malignant. A benign tumor termed adenoma (FIG. 25a) can be defined by a propagated mucosal layer, and sometimes by development of adenopapilloma, however the submucosa is intact and well distinguished from the other colon layers. In a malignant tumor, termed adeno-cacinoma, mucosal cells penetrate beneath the submucosa and eventually lead to a loss of tissue arrangement (FIGS. 25b and 25c). Examinations of the distribution of the different types of tumors in rats treated preventively with glucose or RNase B1 showed that RNase B1 clearly reduced the degree of malignancy (FIG. 9d).

The Effect of RNase B1 as a Therapeutic Agent:

In both modes of application, either directly by osmotic pumps or orally, the well-developed tumors were exposed to RNase B1 during weeks 12-17 of the experiment. In rats treated by osmotic pumps, RNase B1 caused a reduction in the number of tumors per colon (FIG. 26a). The inhibitory effect, about 50% relative to the control, was most significant in rats treated with I-RNase B1.

RNase B1 affected also tumor growth, as demonstrated by size distribution (FIG. 26b). In general, most tumors had a diameter of 3-5 mm, however in PBS-treated rats exceptionally large tumors, of more than 9-12 mm, appeared. This result implies that RNase B1 inhibits or arrests the development of pre-existing tumors. Nonetheless, no significant differences between the effects of RNase B1 and I-RNase B1 were observed.

As in the experiment of RNase B1 preventive effect, the pattern of angiogenesis was also affected by RNase B1 applied via osmotic pumps (FIG. 26c). In PBS-treated rats most of the tumors, about 80%, were red in color. In contrast, in both RNase B1 and I-RNase B1 treated rats only 30% of the tumors were red, whereas the other were pink or white. It appears that RNase B1 reduces angiogenesis also in pre-existing tumors.

In rats fed with encapsulated RNase B1, the effect of the treatment was less significant than that obtained by osmotic pumps (FIGS. 27a-c). This result is explained by assuming that a very small proportion of the protein reaches to the colon. As mentioned before, the microcapsules indeed pass the stomach, but they still have a long route through the small intestine and the cecum. An experiment to test this hypothesis was therefore conducted using CAP microcapsules loaded with a fluorescent protein and given to rats. The rats were sacrificed after 6 hours and the content of their gastrointestinal tract was observed under a fluorescent microscope. It was found that in the duodenum the microcapsules started to dissolve. The dissolution further processed in the ileum and jejunum. When the microcapsules reached into the cecum, most of the fluorescence was diffused into the cecum content. Since the microcapsules were damaged, RNase B1 effect may be reduced due to proteases present in the intestine and cecum.

Despite the fact that orally administered RNase B1 did not decrease the number and size of pre-existing tumors, the distribution among tumor types of color was slightly affected (FIG. 27c). Glucose- and RNase B1 treated rats had about 60% and 40% red tumors, respectively. It appears that orally administrated RNase B1 in the present formulation also affect angiogenesis, but in a moderate way.

Example 5

The Effect of RNase B1 on Human Ht-29 Colon Cancer Cells In Vitro

Material and Experimental Methods

Cell Growth Conditions:

All experiments were performed in human colon adenocarcinoma (HT-29) cells. The cells were grown in 50-ml flasks containing DMEM medium (Biological Industries, Bet Haemek), supplemented with 10% fetal calf serum, 1% glutamine and 1% Antibiotic-Antimicotic solution (Biolab). The cells were trypsinized, and 2 ml medium containing $5 \times 10^4$ cells were plated in each well of a 6-wells plate. Some to plates were supplemented with RNase B1, to a final concentration of $10^{-6}$ M. The cells were incubated at 37° C. in a humidified atmosphere containing 5% $CO_2$. After 48 hours the medium in the presence or absence of RNase B1 was replaced in each well respectively, to maintain a constant supply of ingredients and RNase B1. After four days the medium was removed and the cell cultures were fixed in 4% formaldehyde in PBS (150 mM NaCl, 3 mM KCl, 10 mM $Na_2HPO_4$, 2 mM $NaH_2PO_4$) pH 7.2 for 15 mM on ice. The cells were stained aiming different purpose, as follows.

Direct Staining for Intracellular Actin:

The cells were washed in PBS and permeabilized in PBS containing 0.02% Tween-20 (PBST) for 1 hour in room temperature. Following 3 washes with PBS, the cells were stained for actin with $10^{-6}$ M tetramethylrhodamine β isothiocyanate (TRITC)-labeled phalloidin (Sigma) for 1 hour and let stand in PBS overnight at 4° C. to remove any excess of staining material. The cells were spread in water on a glass slide and visualized using Confocal Laser Scanning Microscope (LSM) 510 (Zeiss).

Immunostaining for Membranal Actin:

The cells were fixed with formaldehyde and washed with PBS as described above, and then incubated with rabbit anti-actin antibodies (Sigma) diluted 1:500 in PBS for 1 hour at room temperature and washed three times with PBS. The cells were then incubated with goat anti-rabbit IgG conjugated to fluorescein isothiocyanate (FITC) diluted 1:100 in PBS for another 1 hour at the same conditions, washed again and visualized as described above.

Immunostaining of RNase B1 on Cell Surface:

Polyclonal antibodies (Aminolab, Israel) were raised in rabbit against purified RNase B1. Anti-RNase B1 was used as primary antibody in HT-29 immunostaining, according to the procedure describe above.

Experimental Results

Direct Staining for Intracellular Actin:

In control cells growing without RNase B1, a fine actin network was observed stained with TRITC, filling the cell cytoplasm. A light stain was observed at the membrane surface (FIG. 28a). In contrast, in RNase B1-treated cells the membrane and the peripheral zone of the cytoplasm in each cell was intensively stained (FIG. 28b), indicating rearrangement of actin network as a response to external addition of RNase B1.

Immunostaining for Membranal Actin:

The FITC-immunostaining showed fine fluorescent spots of actin at the membranal zone in control cells (FIG. 29a). This result coincides with the TRITC staining shown in FIG. 28a. In this experiment, no detergent was used, thus the antibody hardly penetrated into the cells cytoplasm. Therefore, it appears that in these cells, membranal actin interacts with the external environment. In RNase B1-treated cells a much weaker immunostaining was observed (FIG. 29b), implying that RNase B1 previously bound to membranal actin interfered with the binding of the anti-actin antibodies.

Additional cells, not treated with RNase B1, were incubated with the previously mixed rabbit anti-actin and 1 µM actin. A similar faint fluorescence was observed, as described in FIG. 29b (not shown). To eliminate the possibility of spontaneous FITC fluorescence, cells were treated as describe, except anti-actin was omitted. No fluorescent staining was detected.

Immunostaining of RNase B1 on Cell Surface:

Very faint FITC-fluorescence appeared in control cells incubated with anti-RNase B1 (FIG. 30a). However, RNase B1-treated cells exhibited an intense fluorescent response (FIG. 30b). This result indicates a significant presence of RNase B1 over the cell surface, especially on the cells edges and extensions. Treatment with rabbit pre-immune serum (PIS) instead of anti RNase B1 resulted in a very faint fluorescence (FIG. 30c).

Example 6

The Effect of IAc-RNase B1 on Lily Pollen Tubes Growth

Materials and Experimental Methods

Iodoacetylation of RNase B1:

Iodoacetylation of RNase B1 was performed according to Irie et al (Irie M, et al. 1986 J. Biochem. 99(3):627-33). RNase B1 was dissolved in 2.5 ml of 0.1 M acetate buffer, containing 0.1 M iodoacetate, to a final concentration of 10 nM. Following incubation overnight at 37° C., the protein was desalted on a Sephadex G-15 column. The fractions containing the protein were collected and intensively dialyzed against water. After lyophilization, 10 mg of protein were obtained. The iodoacetylated (IAc-) RNase B1 RNase activity was compared to the non-modified RNase B1.

The Effect of IAc-RNase B1 on Lily Pollen Tubes:

Lyophilized IAc-RNase B1 was dissolved to a final concentration of 1 or 5 µM in lily pollen tube growth medium containing 7% sucrose, 1.27 mM Ca(NO$_3$)$_2$, 0.16 mM H$_3$BO3, 1 mM KNO$_3$ and 3 mM KH$_2$PO$_4$ in water (Yokota, E. and Shimmen, T. 1994. Protoplasma 177: 153-162). Lily (*Lilium longiflorum*) pollen grains were germinated in vitro in tubes containing 100 µl of growth medium, in the presence or absence of 10$^{-6}$ M IAc-RNase B1. As additional controls, lily pollen was germinated in the same concentrations of RNase B1 or BSA in growth medium. Following 1.5 hour incubation at 25° C. in darkness, pollen tube length was measured in each treatment under light microscope.

Experimental Results

Iodoacetylation of RNase B1:

Iodoacetate leads to the inhibition of RNase activity, via binding to histidine residues in the active site of RNase. RNase activity of IAc-RNase B1 was 90% less, compared with non-treated RNase B1.

The Effect of IAc-RNase B1 on Lily Pollen Tubes Growth:

Control lily pollen tubes reach a length of 0.26 mm (FIG. 31). In this experiment, BSA was used as a control, since it does not have any cytotoxic effect on pollen tubes. Indeed, at a concentration of 10$^{-6}$ M, BSA did not have a significant effect on pollen tube growth. The inhibitory effect of 5×10$^{-6}$ M BSA may be explained as a result of the fact that pollen tubes are sensitive to changes in the growth medium osmotic potential. Both RNase B1 and IAc-RNase B1 exhibited a clear inhibitory effect on pollen tube growth. In both concentrations IAc-RNase B1 was more effective than RNase B1, however the differences were not significant. Thus, in lily pollen tubes, IAc-RNase B1 inhibits pollen tubes growth in a similar manner of non-modified RNase B1, showing that loss of RNase activity does not reduce its inhibitory effect.

Example 7

Members of the T2 RNase Family Exhibit Anti-Angiogenic and Anti-Cancer Properties Ribonucleases of the T2 family have been shown to share fundamental characteristics, e.g. complete homology of catalytic active site, optimal RNase activity at high temperature and low pH, molecular weight of at least 24 kDa (twice that of RNase A family) and the presence of glycan chains. To determine if members of the T2 RNase proteins have anti-angiogenic properties the human umbilical vein endothelial cell (HUVEC) tube formation assay was employed, as follows.

Materials and Methods

The human umbilical vein endothelial cell (HUVEC) tube formation assay—Generally, the experiment was conducted as previously described for RNase B1 in Ponoe, M. L., 2001 (In vitro matrigel angionesis assays. In Murray, J. C. (ed.) Methods in molecular medicine: Angiogenesis protocols. Humana Press, Totowa, N.J., vol. 46, pp. 205-209). Briefly, Freshly isolated human umbilical vein endothelial cells (HUVEC) were maintained in M199 medium supplemented with 20% FCS, 1% glutamine, 1% antibiotic-antimycotic solution, 0.02% ECGF and 50 U/100 ml heparin. Wells of 96-well plates were coated with growth factor-depleted Matrigel | (Ponoe M L. 2001. In: Murray J C, editor. Methods in molecular medicine. Vol. 46: Angiogenesis protocols. Totowa (NJ): Humana Press. p. 205-9) in M199 media containing 5% FCS and 0.005% ECGF, supplemented with 1 µg/ml angiogenin (to induce tube formation), and were plated with 14,000 HUVECs per plated/well. The various RNases i.e., *Aspergillus niger* RNase B1, *Aspergillus oryzae* RNase T2 (Sigma, 29 kDa) or *E. coli* RNase I (Ambion, 27 kDa) were added at a final concentration of 2 µM. For controls, cells were plated under the same conditions, in the absence or in the presence of any of the above RNases, but in the absence of angiogenin. The 96-well plate was incubated for 24 hours at 37° C. under a humidified atmosphere and 5% carbon dioxide. Three replications were performed for each treatment.

Experimental Results

RNase B1 exhibits a significant anti-angiogenic effect on the HUVEC tube formation—The capacity of various RNases (i.e., *Aspergillus niger* RNase B1, *Aspergillus oryzae* RNase T2 and *E. coli* RNase I) was determined using the HUVEC tube formation assay (FIGS. 32*a-h*). As is shown in FIGS. 32*a-b* while HUVECs incubated in medium in the absence of angiogenin and RNase (Control, FIG. 32*a*), formed only few delicate tubes on the Matrigel surface, in HUVECs incubated in the presence of angiogenin (Positive Control) massive tubes appeared (FIG. 32*b*). In addition, while *Aspergillus niger* RNase B1 and *Aspergillus oryzae* RNase T2 did not have any effect on the cells when given alone (Negative Control, FIGS. 32*c* and 32*e*, respectively), these RNases clearly inhibited angiogenin-induced tube formation (FIGS. 32*d* and 32*f*, respectively). Moreover, RNase T2 was found to have weaker inhibitory effect than the RNase B1 (compare FIG. 32*f* with FIG. 32*d*). Nonetheless, a complete inhibition of tube formation was obtained with 10 µM of RNase B1 or 50 µM of RNase T2 (data not shown). On the other hand, RNase I exhibited a significant inhibitory effect on tube formation in the absence (Negative Control, FIG. 32*g*) or presence of angiogenin (FIG. 32*h*).

Thus, these results clear demonstrate the anti-angiogenic properties of the T2 RNases from highly divergent sources. These results are unique to the instant invention since, up to the present, no publication has shown or suggested the anti-angiogenic activity of RNases of diverse phylogenetic origin belonging to the T2 family.

Example 8

RNase B1 Inhibits the Growth of B16F1 and B16F10 Melanoma Cells-Induced Tumor

To test the anti-cancer properties of RNase B1, an in vivo melanoma mouse model was generated, as follows.

Materials and Experimental Methods

Mice and tumor cells used for the systemic intraperitoneal melanoma mouse model—CD BDF1 and Balb/c mice were used for tumor induciton. Mouse melanoma B16F1 (low metastatic) were obtained from INSIGHT to BIOPHARMACEUTICALS LTD. (Rehovot, Israel).

Generation of a melanoma systemic i.p. mouse model—The melanoma mouse model was generated essentially as described (Geran et al. 1972. Protocol for screening chemical agents and natural products against animal tumors and other biological systems. In: Cancer Chemotherapy Reports Part 3 Vol 3 No 2). Briefly, 2×10$^6$ B16F1 low metastatic cells were injected into the intraperitoneal (i.p.) cavity of each mouse and the presence of cancer tumors was evaluated at day 14 following melanoma cell injection by an overall view of the mouse and/or histopathology examinations.

RNase B1 i.p. administration to the melanoma systemic i.p. mouse model—Twenty-four hours and 5 days following B16F1 melanoma cells injection RNase B1 (5 mg/mouse in 100 μl PBS) or PBS alone was injected into the intraperitoneal cavity.

Mice and tumor cells used for the systemic intravenous (i.v.) melanoma mouse model—Balb/c mice were used for intravenous administrations of mouse B16F10 (highly metastatic) melanoma cells.

Generation of a melanoma systemic i.v. mouse model—B16F10 melanoma cells ($5 \times 10^5$ or $5 \times 10^6$ cells/mouse) were injected into the lateral tail vein of Balb/c mice and the presence of cancer tumors was evaluated at day 14 following melanoma cell injection by an overall view of the mouse and/or histopathology examinations.

RNase B1 i.v. administration to the melanoma systemic i.v. mouse models—RNase B1 (10 mg RNase B1 in 100 μl PBS) or PBS was i.v. injected into the lateral tail vein of the melanoma mouse model starting 24 hour after cells injection and in four days intervals with a total of three injections. At the end of experiment, the lungs were removed, weighed and surface metastases were quantified.

Experimental Results

RNase B1 significantly inhibits tumor growth in melanoma systemic i.p. mice models—The effect of RNase B1 in the i.p./i.p. (i.e., intraperitoneal injection of both melanoma cells and RNase B1) melanoma mouse model was scored 14 days post melanoma cell injection by qualitative tumor observations at the abdomen cavity of the treated mice. As is shown in FIGS. 33a and c, in both BDF1 and Balb/c mice the melanoma cells induced massive tumors filling the abdominal cavity and spreading over the intestinal gut. On the other hand, in RNase B1-treated mice only few small tumors were observed (FIG. 33b, d), demonstrating the tumor growth-inhibitory effect of RNase B1. In this experiment the total amount of RNase B1 was 10 mg/mouse. Similar results were obtained when mice were treated by a single injection of 10 mg RNase B1 or by 10 daily injections of 1 mg RNase B1 (data not shown).

RNase B1 significantly inhibits metastasis/colonization and growth of highly metastatic malignant melanoma tumors in melanoma systemic i.v. mice models—In the i.v./i.v. (i.e., intravenous injection of both melanoma cells and RNase B1) melanoma mouse model the melanoma cells injected in the tail vein lead to development of lung metastases in about two weeks. As is shown in FIGS. 34a-c, two weeks following $5 \times 10^5$ B16F10 melanoma cell injection multiple metastases were observed in the PBS-injected mice (FIG. 34a) as compared with only few metastases in the RNase-treated mice (FIG. 34b). A quantitative determination of the number of metastases revealed a significant decrease 76% ($P<0.001$, FIG. 34c) in the RNase B1-treated mice. When the initial bolus of $5 \times 10^6$ cells/mouse was used, the metastases in the PBS-injected mice were highly intense and too dense to be counted (data not shown). In these mice measurements of the lung weight (FIG. 34d) and tumor size (FIG. 34e) revealed significant reductions of 25% in lung weight ($P<0.01$, FIG. 34d) and tumor size ($P<0.001$, FIG. 34e) in the RNase B1-treated mice as compared with the PBS-treated mice.

These results therefore convincingly demonstrate that RNase B1 can be used to efficiently inhibit the growth and metastasis of highly metastatic malignant melanoma tumors.

Example 9

RNase B1 Inhibits Tumor Growth, Lung Metastases and MMP-2 Production in A375SM-Injected Melanoma Mouse Models To further substantiate the capability of RNase B1 to inhibit the growth of cancer tumors, the RNase B1 was injected into A375SM melanoma cells—induced mouse models, as follows.

Materials and Experimental Methods

Mice used for generating melanoma mouse model—Male athymic Balb/c nude mice were purchased from the Animal Production Area of the National Cancer Institute, Frederick Cancer Research Facility (Frederick, Md.). The mice were housed in laminar flow cabinets under specific pathogen-free conditions and used at 7-9 weeks of age.

Melanoma cells—The highly tumorigenic and metastatic human melanoma A375SM cell line was obtained from MD Anderson Cancer Center, Houston, Tex. To prepare tumor cells for inoculation, the cells in exponential growth phase were harvested by brief exposure to a 0.25% trypsin/0.02% ethylenediaminetetraacetic acid solution (w/v). The flask was sharply tapped to dislodge the cells and supplemented medium was added. The cell suspension was pipetted to produce a single-cell suspension. The cells were washed and resuspended in $Ca^{2+}/Mg^{2+}$-free Hanks' balanced salt solution (HBSS) to the desired cell concentration. Cell viability was determined by trypan blue exclusion, and only single-cell suspensions of >90% viability was used.

Generation of melanoma mouse models—Subcutaneous (s.c.) tumors were produced by injecting $10^5$ tumor cells/0.1 ml HBSS over the right scapular region of the mice. Growth of subcutaneous tumors was monitored by weekly examination of the mice and measurement of tumors with calipers. The mice were sacrificed 5 weeks following the melanoma cell injection, and tumors were frozen in OCT compound (Sakura Fineter, Torrance, Calif.), or formalin fixed and then processed for immunostaining and Hematoxylin and Eosin (H&E) staining.

Generation of experimental lung metastasis—To form lung metastases $10^6$ tumor cells in 0.1 ml of HBSS were injected into the lateral tail vein (i.v.) of nude mice. The mice were sacrificed 60 days following melanoma cell injection, and the lungs were removed, washed in water, and fixed with Bouin's solution for 24 hours to facilitate counting of tumor nodules. The number of surface tumor nodules was counted under a dissecting microscope.

RNase B1 administration—Both the subcutaneous and intravenous melanoma to cell injected mice were treated every other day with either 1 mg/100 μl of RNase B1 aqueous solution or with phosphate-buffered saline (PBS) by intraperitoneal (i.p.) injection.

CD31 and MMP-2 immunohistochemical analysis—Sections of frozen tissues were prepared from tumor xenografts. The tissue section slides were rinsed twice with PBS, and endogenous peroxidase was blocked by the use of 3% hydrogen peroxide in PBS for 12 minutes. The samples were then washed three times with PBS and incubated for 10 minutes at room temperature with a protein-blocking solution consisting of PBS (pH 7.5) supplemented with 5% normal horse serum and 1% normal goat serum. Excess blocking solution was drained and the samples were incubated for 18 hours at 4° C. with a 1:100 dilution of monoclonal rat anti-CD31 (1:800) antibody or a 1:200 dilution of anti-MMP-2 (PharMingen, San Diego, Calif.). The samples were then rinsed four times with PBS and incubated for 60 minutes at room temperature with the appropriate dilution of peroxidase-conjugated anti-mouse IgG1, anti-rabbit IgG, or anti-rat IgG. The slides were rinsed with PBS and incubated for 5 minutes with diaminobenzidine (Research Genetics, Huntsville, Ala.). The sections were then washed three times with distilled water and counterstained with Gill's hematoxylin (Sigma-Aldrich Co. St Louis, Mo.). For the quantification of microvessel density (MVD), ten fields of the CD31 stained samples were counted at 100× magnification. Sections (4 μm thick) of formalin-fixed, paraffin-embedded tumors were also stained with H&E for routine histological examination.

Experimental Results

RNase B1 treatment significantly reduced tumor size in A375SM melanoma cells-injected mice—The effect of RNase B1 on the tumor growth of human melanoma cells was determined in two sets of nude mice. In the first set of nude mice (n=5), A375SM melanoma cells ($5 \times 10^5$) were injected subcutaneously and three days later, animals injected with tumor cells were subsequently i.p. injected every other day for 30 days with 1 mg of RNase B1 or control PBS. Tumor cells in the animals treated with PBS grew progressively and produced large tumors reaching the size up to 700 mm$^3$ mean volume (FIG. 35, Control). In contrast, treatment with to RNase B1 reduced tumor growth to maximum 100 mm$^3$ mean volume during the same periods of time (FIG. 35, RNase B1). In the second set of nude mice (n=8) the mice were injected and treated exactly as described for the first set and showed exactly the same effects of RNase B1 on tumor growth (data not shown).

RNase B1 treatment significantly reduced the incidence and number of lung metastasis in A375SM melanoma cells-injected mice—To determine the effect of RNase B1 on metastasis of human melanoma cells, A375SM 10$^6$ cells were injected intravenously into nude mice to produce experimental lung metastasis. Five days later, animals injected with tumor cells were also i.p. injected with 1 mg of RNase B1 or control PBS every other day for 60 days. It was found that both the incidence and number of lung metastasis of A375SM cells were reduced in RNase B1-treated mice, when compared with the control group. In control mice, A375SM cells produced numerous lung metastases (median, 65; range, 16 to 200), whereas treatment with RNase B1 significantly inhibited the ability of A375SM cells to form metastasis in nude mice (median, 10; range, 0 to 75; $P<0.05$).

RNase B1 treatment decreases the expression of MMP-2 in A375SM melanoma mouse models—To determine whether RNase B1 suppresses the expression of MMP-2 in vivo, tissue sections of tumor xenografts were subjected to immunohistochemical analysis using an MMP-2 specific antibody. MMP-2 staining was observed in control-injected A375SM tumors, but was significantly decreased in RNase B1-treated tumors (data not shown). Thus, RNase B1 significantly inhibited the expression of MMP-2 in vivo in melanoma cells.

Altogether, these data demonstrate that treatment of mice with RNase B1 leads to suppression of tumor growth and metastasis, and to inhibition of synthesis of angiogenesis factors such as MMP-2.

Example 10

Local Subcutaneous Administration of RNase B1 Inhibits Angiogenesis

Since MMP-2 is an important angiogenic factor, the present inventors have determined whether RNase B1 could affect angiogenesis in vivo, as follows.

Materials and Experimental Methods

Local induction of angiogenesis—Gel foams impregnated with 100 ng/sponge angiogenin were subcutaneously implanted in both sides of a nude mouse and following 2 days the mice were intraperitoneally injected 7 times, every two days, on one side with RNase B1 (250 μM RNase B1 in 100 μl) and on the other side with PBS.

Immunofluorescent staining of CD31/PECAM-1—Frozen gelfoam specimens (obtained from Pharmacia & Upjohn, Peapack, N.J.) were sectioned (10-12 μm), mounted on positively charged slides and air-dried for 30 minutes. The sections were then fixed for 5 minutes in cold acetone following by a 5-minutes incubation in a solution of 1:1 acetone:chloroform and an additional 5-minutes incubation in acetone alone. The samples were then washed three times with PBS, incubated for 20 minutes at room temperature with a protein-blocking solution containing 4% fish gelatin in PBS, and incubated for 18 hours at 4° C. with a 1:800 dilution of rat monoclonal anti-mouse CD31 antibody (Pharmingen, San Diego, Calif.). Following antibody incubation the slides were rinsed three times with PBS (3 minute each) and incubated for 1 hour in the dark at room temperature with a 1:200 dilution of a secondary goat anti-rat antibody conjugated to Goat anti-rat Alexa 594 (Molecular Probes Inc., Eugene, Oreg.). Samples were then washed three times with PBS (3 minute each) and then mounted with Vectashield mounting medium for fluorescence with Hoechst 33342, trihydrochloride, trihydrate 10 mg/mL solution in water (Molecular Probes Inc., Eugene, Oreg.). Immunoflorescence microscopy was performed using a Zeiss Axioplan microscope (Carl Zeiss, New York, N.Y.) equipped with a 100-W HBO mercury bulb and filter sets from Chroma, Inc. (Burlington, Vt.) to individually capture red, green, and blue fluorescent images. Images were captured using a C5810 Hamamatsu color chilled 3CCD camera (Hamamatsu, Japan) and digitized using Optimas imaging software (Silver Springs, Md.). Images were further processed using Adobe PhotoShop software (Adobe Systems, Mountain View, Calif.). Endothelial cells were identified by red fluorescence.

TUNEL assay—For terminal deoxynucleotidyl transferase-mediated dUTP-nick end-labeling (TUNEL) assay, a Klenow-FragEl kit (Oncogene Cambridge, Mass.) was used. Sections (10 μm) were deparaffinized in xylene, followed by rehydration in to gradual ethanol solutions (100, 100, 95 and 70% ethanol—5 min each). The preparations were subjected to a proteinase K treatment for 15 min, extensively washed in PBS, and preincubated at room temperature in an equilibration buffer supplied by the manufacturer. After tapping off excess liquid, terminal deoxynucleotide transferase and digoxigenin-11-dUTP were applied to the preparations. The slides were incubated at 37° C. for 1 hour, washed in prewarmed stop/wash buffer at 37° C. for 30 minutes, and then washed three times in PBS. Specific staining was achieved by the addition of antidigoxigenin antibody carrying peroxidase as the reporter conjugate. After counterstaining, the slides were mounted under a glass coverslip, and the brown apoptotic cells were visualized by light microscopy.

Experimental Results

RNase B1 inhibits angiogenin-induced development of blood vessels—To test the capacity of RNase B1 to inhibit angiogenesis in vivo, angiogenin impregnated gel foams were subcutaneously implanted at both sides of a nude mouse, followed by i.p. injections of RNase B1 or PBS. As is shown in FIG. 37, while angiogenin-PBS treatment resulted in massive development of blood vessels (FIG. 37, Angiogenin), the angiogenin-RNase B1 treatment resulted in a significant reduction in the blood vessels (FIG. 37, Angiogenin and RNase B1).

These results demonstrate the ability of RNase B1 to inhibit angiogenesis in vivo.

RNase B1 reduces the tumor MVD in A375SM-induced tumor—Tumor-associated neovascularization as indicated by microvessel density (MVD) was determined by immunohistochemistry using an anti-CD31 antibody. A significant reduction in tumor MVD per field was observed following treatment with RNase B1 as compared with control tumors. The mean number of MVD was 12±5 in RNase B1-treated A375SM tumors as compared with 43±7 for control, untreated A375SM-induced tumors (data not shown). Moreover, the number of TUNEL-positive tumor cells was inversely correlated with MVD in the studied tumors. The number of tumor cells undergoing apoptosis was higher in the RNase B1-treated animals than in tumors in control mice. Thus, the percentage of apoptotic cells was 31.2±7.3% in RNase B1-treated A375SM melanoma tumors. In contrast, the percentage of apoptotic cells to was 2.2±1.1% for control A375SM tumors.

Thus, these results demonstrate that RNase B1 treatment significantly decreased melanoma tumor-associated neovascularization and increased apoptosis of tumor cells.

Example 11

RNase B1 Reduces Microvessel Density in DMH Model

Materials and Experimental Methods

Rats—Male Wistar rats aged 6 weeks and weighing about 160 g were obtained from the Charles River-derived outbred male rat.

DMH—1,2-Dimethylhydrazine (DMH) was purchased from Sigma (St. Louis, Mo., USA). DMH was dissolved immediately before use in a solution of 1.5% EDTA in PBS and the pH of the solution was brought to pH 6.5.

Generation of DMH-models—DMH was intramuscularly (i.m.) injected to rats (40 mg/kg body weight). At injection time rat weighted 250 gr.

Tumors were induced in rats using dimethylhydrazine (DMH) administered in subcutaneous injections of DMH (15 mg/100 g body weight, once a week for 5 weeks). Control groups received injections of PBS plus the vehicle (EDTA).

Analysis of DMH-models—The rats were first anesthetized with ether and then sacrificed. From each rat, the colon was excised and the aberrant crypt foci (ACF) or tumors were counted and measured. Tumors from control and from RNase B1-treated rats were fixed and embedded in paraffin and the tumor sections were further analyzed by histopathology (H&E staining), immunostaining with anti-CD-31 antibody for blood vessel monitoring or TUNEL assay for apoptosis.

Immunofluorescent staining of CD31/PECAM-1—was performed as described in Example 10, hereinabove. Briefly, paraffin sections (10-μm) from tumors generated in DMH or DMH+RNase B1-treated mice were subjected to CD31 immunostaining using the PECAM-1 (H-300) antibody (sc-8306, Santa Cruz Biotechnology, Inc. Santa Cruz, Calif.). Blood vessels in median tumor cross sections were counted and their diameters were measured. In each tumor, the ratio between blood vessel total area and tumor-section area was calculated. The experiments were to repeated twice, and each treatment was applied to 6-to-10 rats.

Experimental Results

Tumor-associated neovascularization decreased in RNase B1-DMH treated mice—CD31 immunostaining revealed the presence of blood vessels within the tumor and served as a basis for calculation of the microvessel density (MVD). As is shown in FIGS. 42a-b, RNase B1 administration was found to significantly reduce the number of blood vessels (angiogenesis) per tumor.

Example 12

RNase B1 Inhibits Invasiveness/Colonization Capacity of Melenoma, Colon and Mammary Carcinoma Cells In Vitro Since RNase B1 was shown to affect cancer cell's morphology and actin organization the present inventors have further examined whether RNase B1 also affects cell motility, as follows.

Material and Experimental Methods

Colon carcinoma (HT-29) or breast cancer cells (ZR-75-1) invasion/colonization assay—HT-29 colon cancer cells or ZR-75-1 cells were treated in the presence or absence of 1 and 10 μM RNase B1 for 4 days. Wells and Matrigel-coated inserts of a commercially available 24-well invasion chamber (Becton Dickinson, Bedford, Mass.) were rehydrated in 0.5 ml of serum free medium overnight and processed according to the manufacturer's instructions. Half ml of HT-29 control (i.e., in the absence of RNase B1) or RNase B1-treated cell suspensions containing $2.5 \times 10^4$ cells each was added to the top of the chambers and 0.750 ml of DMEM media containing 10% FCS were added to the lower chamber. The invasion chambers were incubated for 22 hours in a 37 degrees centrigrade cell culture incubator. The non-invading cells on the upper surface of the membrane of the insert were removed by scrubbing. The cells on the lower surface of the membrane were stained with Diff-Quik™ stain. The membranes were fixed and the cells were counted at ×200 magnification under a light microscope. The assay was carried out in triplicate.

Matrigel-coated filter invasion assay—A375SM cells were treated in the presence or absence of RNase B1 and following 22 hours the number of cells invaded the Matrigel-coated filter was counted.

MMP-2 release from A375SM cells—Metastatic A375SM cells ($5 \times 10^3$) were grown in Complete Eagle's minimum essential medium (CMEM), were plated in six-well plates and allowed to attach for 24 hours. Cells were treated for 4 days with 1 or 10 μM RNase B1, or PBS. Treatment for 4 days was found to be optimal for the RNase B1 to affect MMP-2 release. On day 5, CMEM was removed and replaced with serum-free medium overnight. The supernatant was collected and centrifuged and media aliquoted in 500 μl samples and stored at −20° C. Total MMP-2 was determined by the quantikine MMP-2 immunoassay kit (R&D Systems Inc, Minneapolis, Minn.). Samples were diluted 10-fold in a diluent supplied by the kit. MMP-2 was measured according to the supplier instructions and the results were adjusted to cell number.

MMP-2 Collagenase activity (Zymograms)—MMP-2 activity was determined on substrate-impregnated gels. HUVECs cells or metastatic A375SM cells ($5 \times 10^3$) were plated in six-well plates and allowed to attach for 24 hours. Cells were treated for 4 days with 1-5 or 10 μM RNase B1, or PBS. Treatment for 4 days was found to be optimal for the RNase B1 to affect MMP-2 activity. On day 5, CMEM was removed and replaced with serum-free medium overnight. The supernatant was collected, the volume adjusted for cell number, loaded, and separated on gelatin-impregnated (1 mg/ml; Difco, Detroit, Mich.) sodium dodecyl sulfate/8% polyacrylamide gels under nonreducing conditions, followed by 30 minutes of shaking in 2.5% Triton X-100 (BDH, Poole, UK). The gels were then incubated for 16 hours at 37° C. in 50 mmol/L Tris, 0.2 mol/L NaCl, 5 mmol/L $CaCl_2$ (w/v) at pH 7.6. At the end of the incubation, the gels were stained with 0.5% Coomassie G 250 (Bio-Rad, Richmond, Calif.) in methanol/acetic acid/$H_2O$ (30:10:60). The presence of MMP-2 Collagenase activity is seen as a white band on blue gels.

Experimental Results

RNase B1 reduces HT-29 or ZR-75-1 invasiveness in vitro—As is shown in Table 6, hereinbelow, HT-29 and ZR-75-1 cells were able to penetrate the Matrigel-coated filters. Surprisingly, RNase B1 was found to significantly and dose-dependently (1 and 10 μM) inhibit the invasiveness/colonization capacity of colon carcinoma cells.

TABLE 6

The effect of RNase B1 on HT-29 or ZR-75-1 invasiveness

| Cell lines | Control | RNase B1 concentration | |
|---|---|---|---|
| | | 1 μM | 10 μM |
| HT-29 | 963.7 ± 95.7 | 623.3 ± 104.2 | 223.7 ± 13.1 |
| ZR-75-1 | 1297.7 ± 62.5 | 784.0 ± 51.5 | 271.7 ± 16.6 |

Table 6: The Effect of RNase B1 on ZR-75-1 breast cancer and HT-29-colon cancer cell invasiveness through Matrigel-coated filters. In HT-29 and ZR-75-1 cells, RNase B1 at 1 μM ($P < 0.05$ and $P < 0.01$, respectively) and 10 μM ($P < 0.01$ and $P < 0.001$, respectively) inhibited cell invasiveness in a dose-responsive manner.

RNase B1 reduces A375SM invasiveness in vitro—A375SM cells were treated in the presence or absence of 1 or 10 μM RNase B1 and the degree of cell invasiveness was measured in matrigel-coated filters. As is shown in FIG. 38, a significant dose-dependent effect of RNase B1 on the inhibition of A375SM invasiveness was observed. While in untreated A375SM cells (control) 1216±68 cells penetrated Matrigel-coated filters, 725±59 or 211±14 A375SM cells treated with 1 or 10 μM RNase B1 penetrated the Matrigel-coated filters.

RNase B1 significantly inhibits the secretion of MMP-2—The level of MMP-2 release was determined in vitro from A375SM cells. As is shown in FIG. 48, a dose-dependent effect of RNase B1 in inhibiting total MMP-2 release was obtained, with the maximal inhibitory effect observed in the presence of 10 μM RNase B1.

MMP-2 collagenase activity reduces following RNase B1 treatment—Zymograms of the supernatant of A375SM or HUVEC cells were used to determine MMP-2 activity. As is shown in FIG. 49a-b, while both untreated A375SM (FIG. 49a) and HUVEC (FIG. 49b) cells exhibit a strong MMP-2 activity, RNase-treated cells exhibited a dose-dependent decrease in band intensity of the 72 kDa MMP-2, suggesting decreased MMP-2 activity. Similarly, a dose-dependent decrease was also observed in MMP-9 activity in the RNase B1-treated cells (FIG. 49b).

Altogether, these results clearly demonstrate the anti-angiogenic/anti-cancer characteristics of RNase B1.

Example 13

Intravenous and Intraperitoneal Administrations of RNase B1 Reduce Tumor Size in HT-29 Colon Cancer Models Materials and Experimental Methods Generation of an s.c./i.v. colon cancer xenograft model—Tumors of human colon cancer origin (HT-29) were grafted into 4-5 week old nude mice (CD-1 nu/nu) males, weighing 18-20 grams at onset of experiment. HT-29 cells ($2 \times 10^6$/mouse) were injected subcutaneously (s.c.) into the mice, at the left hip. T2 RNase (RNase B1, 5 mg in 100 μl PBS) or PBS alone was injected intravenously (i.v.) into the tail vein 24 hours, 5 days, and 10 days after administration of the colon cancer cells. After 15 days, the mice were sacrificed and the tumors or the area of injection were assessed by histopathological examination.

Paraffin sections of control and T2 RNase-treated tumors were stained with hematoxylin and eosin (H&E) and with Klenow-FragEl kit (Oncogene, Cambridge, Mass.) for evidence of apoptosis.

Generation of an s.c./i.p. colon cancer xenograft model—Colon cancer cells (HT-29) and nude mice (CD-1 nu/nu) were as for the s.c./i.v. model. At the $1^{st}$ day of experiment, cells were injected into the left hips of mice ($10^6$ cells/mouse). RNase B1 was injected into the peritoneal cavity, starting from day 2 and every other day. Two experiments were performed. In the first experiment, RNase B1 at doses of 1 and 5 mg/injection in 100 μl PBS was applied. In the second experiment, doses of RNase B1 ranged between 0.01-1 mg/injection were used. PBS alone was injected as control. The tumors were excised at day 30 of experiment, for size measurements and histopathological examinations. Tumor volume was calculated using the equation (length×width)/2.

Experimental Results

Intravenous administration of RNase B1 can efficiently reduce tumor weight—In RNase B1-treated mice, a 60% reduction in tumor weight was observed compare to control (FIGS. 36a-b). These results show that the intravenous administration of RNase B1 is highly effective in inhibiting colon carcinoma tumor growth.

Intraperitoneal administration of RNase B1 efficiently reduces tumor size—In the sc/ip mice model, RNase B1 significantly inhibited the growth of HT-29 derived-carcinoma (FIGS. 39a-b). At the therapeutic doses of 1 and 5 mg/injection (50 and 250 mg/kg), tumor volume was reduced by 44% and 41% respectively (P<0.05, FIG. 39b). At 0.001, 0.01, 0.1, 0.5 and 1 mg/injection (0.05, 0.5, 5, 25 and 50 mg/kg, respectively), tumor volume was reduced by 3% 41.5%, 34.4%, 51.1% and 62.2% respectively (FIG. 39a), as compared to control (P<0.05). These results are consistent with the previous in vitro experiments with HT-29 cells, in which RNase B1 at concentrations ranged between 1-4 μg/100 μl (0.25-1 μM) had similar inhibitory effect on the rate of clonogenicity. Thus, these results demonstrating the preventing (FIG. 39a) as well as the therapeutic (FIG. 39b) effect of RNase B1 on colon tumor size.

RNase B1 accumulates in the peritoneum of the treated mice—As is shown in FIGS. 40a-c, immunohistochemial staining using rabbit anti-RNase B1 and FITC-conjugated goat anti rabbit revealed the presence of RNase B1 in the RNase B1-treated mice (FIG. 40b) but not the PBS treated mice (FIG. 40c). In addition, RNase B1 immunostaining of the cross sections of the treated mice revealed the accumulation of RNase B1 onto the basal membrane of the tumor blood vessel (FIGS. 41a-c).

Thus, these results demonstrate that RNase B1 enters the peritoneum and then finds its way towards the basal membrane of tumor blood vessels.

It is worth mentioning that in the intraperitoneal mode of administration appears to be non-toxic to the nude mice, since

Example 14

RNase B1 Enhances Apoptosis in Cancer Animal Models

Materials and Experimental Methods

TUNEL assay—was performed as described in Example 10, hereinabove.

Melanoma mouse models—B 16F1-induced melanoma mouse models were to generated as described in Example 8, hereinabove.

Colon cancer mouse models—DMH and HT-29 colon cancer models are described in Examples 11 and 13, hereinabove, respectively.

Experimental Results

RNase B1 enhances apoptosis in B16F1-induced melanoma cell tumors—To determine the rate of apoptosis within the tumors, tumor tissue sections from RNase B1-treated or untreated melanoma mouse models were subjected to a TUNEL assay. As is shown in FIGS. 43a-b, in the RNase B1-treated mice the apoptosis rate was significantly increased as compared with the untreated melanoma mouse model.

Enhanced apoptosis rate in RNase-treated DMH-colon cancer rat model—As is shown in FIG. 44a, tumors obtained from the DMH colon cancer model exhibited negligible levels of apoptosis. On the other hand, tumors obtained from RNase B1-treated rats exhibited a significant level of apoptosis (FIG. 44b). When 10 different microscopic fields at ×200 magnification were counted in three different tissue sections the number of apoptotic cells was found to be 2.01±0.2/microscopic field in control, untreated tumors and 37±5/microscopic field in tumors of the RNase B1-treated animals.

High proportion of apoptotic cells in HT-29 colon carcinoma-induced mice which were treated with RNase B1—As is shown in FIGS. 45a-d, while untreated HT-29-induced colon carcinoma mice exhibited vital and actively dividing nuclei (FIGS. 45a and c), the RNase-treated mice displayed condensed cytoplasm and nuclei (FIG. 45b) and high proportion of apoptotic cells (FIG. 45d).

Altogether, these results demonstrate the significant apoptosis effect of RNase B1 on the various cancer-induced animal models, and suggest the use of RNase B1 in treatment of disorders of apoptosis and abnormal accumulation of cells, such as cancer and inflammatory/ischaemic disease.

Example 15

RNase B1 and Taxol Exhibit A Synergistic Effect on Inhibiting Relative Tumor Volume in Colon Cancer Xenograft Models To test whether RNase B1 can inhibit tumor growth on established tumors and to determine whether RNase B1 displays an additive or synergistic effect with Taxol, a common colon cancer cytotoxic drugs, RNase B1 was employed together with Taxol on colon cancer xenograft models, as follows.

Materials and Experimental Methods

The following protocol is based on Fujii T., et al. Anticancer Res. 23:2405-2412 (2003).

Animals—Nude male mice (balb/c nu/nu), 7 week old, weigh 22 gram each.

Cancer cells—Human colon cancer LS174T. LS174T cancer cells ($1×10^6$ cells per mouse per 100 µl medium) were subcutaneously injected into the nude mice.

RNase B1 administration—started when tumors are palpable (10-13 days after cell injection), and consisted of 15 i.p. injections every other day. RNase B1 doses were 10 and 1000 micrograms/100 µl/injection (0.5 and 50 mg/kg, respectively).

Taxol preparation and administration—Fifty mg Taxol were dissolved in 18 ml propylene glycol and 3 ml ethanol, following which 9 ml of water were added. Taxol was administered by i.p. injections for 5 consecutive days out of 7 days over a period of 3 weeks, starting when tumors are palpable (13 days after cell injection).

Treatments—The combined treatment was applied as followed:

Control: PBS or propylene glycol+ethanol–3 mice for each vehicle.

RNase B1: 50 mg/kg RNase B1 (1000 µg/injection).

RNase B1+Taxol: 50 mg/kg RNase B1 and 5 mg/kg Taxol.

Taxol: 5 mg/kg TAXOL (100 µg/injection).

During the experiment, the tumors were measured twice a week using a caliper. Tumor volume was calculated using the equation (length×$width^2$)/2. Each mouse was tagged and monitored individually. Relative tumor volume (RTV) was defined as $RTV=V_i/V_0$, where $V_i$ was tumor volume at any given time and $V_0$ was that at the time of initial treatment. At the end of experiments, samples were taken to histology.

Experimental Results

The highly angiogenic LS174T cell line was used in the combined RNase B1 and Taxol treatment. As is clearly shown in FIG. 46, while Taxon displays only marginal effect on the relative tumor volume (RTV), RNase B1 exhibits a significant effect in inhibiting tumor growth. However, when RNase B1 and Taxol were concomitantly injected into the mice, a significant inhibition of tumor growth was observed, demonstrating a synergistic, rather that additive effect of RNase B1 to taxol treatment. Moreover, the RTV at endpoint were 158.2, 195.3, 61.4 and 13.43 in control, Taxol, RNase B1 and RNase B1+Taxol treatments, respectively (FIG. 46), demonstrating, for the first time, an efficient suppression of tumor growth.

These results indicate that combined treatment has a greater potential for inhibiting tumor growth rate than each drug alone. These results further demonstrate the ability of RNase B1 to inhibit the growth of pre-established tumors.

Example 16

Actin-Binding in Diverse Rnase B1

The actin-binding activity of diverse RNase of the T2 family was investigated.

Materials and Experimental Methods

Actin-Western Blot—This assay is based on the method described by Hu et al. 1993 (Actin is a binding protein for angiogenin. Proc Natl Acad Sci USA. 90:1217-21). Briefly, RNase B1, Angiogenin, RNase I (1 µg of each protein) and actin (as a positive control) were subjected to SDS-PAGE, followed by Western Blot analysis. The nitrocellulose membrane was blocked overnight with BSA and incubated for another overnight in 5 ml buffer containing 25 µg G-actin, following which a monoclonal mouse anti-actin IgM was applied followed by HRP-conjugated goat anti mouse IgM Actin (Ab-1) Kit, CAT #CP01-1EA (Oncogene)]. The HRP-derived signals were detected by the Super-Signal® enhanced-chemiluminescence system (ECL, Pierce).

Experimental Results

Actin-binding properties of bacterial and *A. niger* T2 RNase—As is shown in FIGS. 47*a-b*, the actin-Western Blot analysis revealed a strong association of RNase B1 to G-actin, demonstrating its actin-binding capacity.

Example 17

Cellular Localization of Rnase B1

Materials and Experimental Methods

Immunocytochemistry staining of cultured Cells—A375SM or HUVEC cells were cultured on chamber slides and fixed with cold acetone for 20 minutes. The slides were rinsed and then blocked with 4% gel fish for 20 minutes at room temperature. The chamber slides were incubated with primary antibody overnight at 4° C. After being washed with 0.01 M pH 7.4 PBS three times, the cells were incubated for 60 minutes with FITC-conjugated antirabbit secondary antibody diluted with 4% gel fish in PBS. For HUVEC CD31 immunostaining, the specimens were incubated for 18 hour at 4° C. with a 1:800 dilution of rat monoclonal anti-mouse CD31 antibody (Pharmingen, San Diego, Calif.). After the samples were rinsed with PBS three times for 3 minutes each, the slides were incubated for 1 hour in the dark at room temperature with 1:200 dilution of secondary goat anti-rat antibody conjugated to Goat anti-rat Alexa 594 (Molecular Probes Inc., Eugene, Oreg.). Samples were washed three times with PBS, 3 minutes each, and mounted with Vectashield mounting medium for fluorescence with Hoechst 33342, trihydrochloride, trihydrate 10 mg/mL solution in water (Molecular Probes Inc., Eugene, O). The slides were viewed on Zeiss laser scanning confocal microscope. Z-sections and XZ-sections were obtained from 3D scanning by using LSM510 software.

Experimental Results

RNase B1 is localized within the HUVEC cells—As is shown in FIGS. 50*a-s*, RNase B1 gradually penetrates the cell membrane which is detected by the red label of CD31 immunostaining and enters into the cell.

RNase B1 reaches the nucleus of A375SM melanoma cells—As is shown in FIGS. 51*a-c*, while within two hours of exposure to RNase B1 the cell morphology changes and becomes round (FIG. 51*a*), after four hours the RNase B1 is seen within the cytoplasm of some cells (FIG. 51*b*) and following eight hours reaches the cell nuclei (FIG. 51*c*). It is worth mentioning that many of the melanoma A375SM cells exhibit apoptotic characteristics following 8 hours of exposure to RNase B1 (FIG. 51*c*).

Thus, these results demonstrate that RNase B1 enters both HUVEC and melanoma A375SM cells and induces apoptosis in the melanoma cells. The results also clearly demonstrate that RNase B1 penetration into the cells is a slow process lasting several hours, in contrast to the immediate response seen in pollen tubes.

Example 18

Cloning the Gene Encoding Rnase B1

The mechanism by which RNase B1 is produced by the fungus *Aspergillus niger* is not known yet. The genes coding *Aspergillus oryzae* RNase $T_2$ (Ozeki et al. 1991. Cloning and nucleotide sequence of the genomic ribonuclease T2 gene (mtB) from *Aspergillus oryzae*. Curr Genet. 19:367-73) and *Rhizopus* niveus RNase Rh (Horiuchi et al. 1988. Primary structure of a base non-specific ribonuclease from *Rhizopus niveus* J Biochem 103:408-18), which are RNase T2-family members, have been cloned. Understanding the genetics of RNase B1 is of great importance, since the potential for recombinant protein production would be augmented. To study the amino acid sequence of RNase B1, it was first digested with trypsin and chymotrypsin and fragments were analyzed by Liquid Chromatography Mass Spectra (LC-MS) and compared against database. Some peptide sequences were found to be 100% homologous to *A. saitoi* RNase M (Accession No: P19791; Watanabe et al. 1990. Primary structure of a base non-specific and adenylic acid preferential from *Aspergillus saitoi*. J. Biochem. 10:303-310) and together they comprised 60% of the protein sequence (data not shown). It is interesting to mention that the taxons saitoi and phoenicus were previously classified as variants of the *A. niger* group (Al-Musallam, A. 1980. Revision of the black *Aspergillus* species. PhD. Thesis, State University, Utrecht, Netherlands). The identified amino acid sequences enabled the design of DNA oligonucleotide primers which can be used on genomic DNA. Since most amino acids are encoded by at least two nucleotide codons, the present inventors used degenerate primers having low degeneracy, according to *A. niger* codon usage, as follows: Forward primer -5'-TTYTGGGAR-CAYGARTGGAAY-3' (for amino acids F107-N112) (SEQ ID NO:1) and reverse primer -5'-CCYTTIACRTTRAAR-TARTARTA-3' (reverse complement for amino acids Y200-K206) (SEQ ID NO:2). The letter "Y" refers to any of the nucleotides C or T and the letter "R" refers to any of the nucleotides A or G. Deoxyinosine (I) replaces any of the four nucleotides.

Experimental Results

The major 400-bp band obtained after PCR amplification (FIG. 52) was excised from the gel and cloned into pGEM-T vector (Promega) for DNA sequence analysis. The 300 nucleotides that were obtained (SEQ ID NO: 4) created an open reading frame for 100 amino acids (SEQ ID NO: 5, FIG. 53), which matched the F107-K206 of RNase M almost completely (except position 123 where glutamic acid replaced aspartic acid in RNASE B1 and RNase M, respectively). This sequence makes the mid region of the gene. Further experiments are currently being conducted to complete the full gene sequence of RNase B1 from *Aspergillus niger* B1 (CMI CC 234626).

Example 19

Cloning and Purification of the Human RNase 6PL Protein

Deletion of a region of chromosome 6 in humans (6q27) has been considered to be associated with several human malignancies (Cooke et al. 1996. Genes Chromosomes Cancer 15:223-233; Saito et al. 1992. Cancer Res 52:5815-5817). It was found that this region contains the putative tumor suppressor RNase6PL gene which shares homology with the RNase T2 family (Trubia et al. 1997. Genomics 42:342-344; Acquati et al. 2001. Meth Mol Biol 160:87-101), including RNase B1. Due to the anti-cancer capacities of T2-family RNases, human RNase T2 represents a highly advantageous agent for treating cancer by virtue of its being of endogenous human origin, and thereby being optimally non-immunogenic and non-toxic when administered to humans. To test the possibility that the human RNAse 6PL protein can be used as an anti-cancer agent, the human RNAse 6PL protein was synthesized, as follows.

Materials and Experimental Methods

Expression of human RNAse6PL protein in *Pichia pastoris*—The sequence of the gene for the RNase6PL was identified in the human genome project (genomic sequence: GenBank Accession No. NT_007422; cDNA sequence: GenBank Accession No. NM_003730). Out of 28,751 bp of the full gene, only 719 bp form the open reading frame. To produce a recombinant RNAse6PL protein the synthetic 719 bp cDNA (GenArt GmbH, Germany) was ligated into the pPIC9K plasmid and was to further transformed into the *Pichia pastoris* yeast. The recombinant yeasts were grown under inductive conditions (i.e., in the presence of 0.5% methanol), and the obtained colonies were tested for the presence of the RNAse6PL insert.

Purification of the human RNase6PL protein from the yeast clone—To purify the recombinant RNase6PL protein a positive colony (i.e., a colony containing the RNAse6PL insert cDNA) was fermented according to manufacturer's instructions (Invitrogen Inc.) and the medium supernatant was heat treated (10 minutes at 90° C.) followed by buffer exchange by dialysis using 20 mM Tris-HCl pH 7. The relatively pure protein was loaded on a Q Sepharose column in a Fast Protein Liquid Chromatography (FPLC) (Amersham Pharmacia Biotech, Buckinghamshire, U.K.), using a 5-ml column at a flow rate of 5 ml/min. To elute the active RNase6PL protein, an NaCl gradient from 0 to 1 M was applied to the column (for a time period of 20 minutes) and eluted proteins were collected in 0.5 ml fractions.

Experimental Results

The structure of the human RNase 6PL gene—The sequence of the gene for RNase6PL was identified in the human genome project. Out of 28,751 bp of the full gene, only 719 bp (arranged in 9 exons) form the open reading frame.

Identification of an RNAse6PL yeast clone—The coding region of RNase6PL was cloned into the pPIC9K plasmid of the *Pichia pastoris* yeast and one colony was found to contain a gene insert of about 750 bp, demonstrating the cloning of a recombinant RNase6PL in yeast.

Recombinant RNase6PL is produced in the *Pichia pastoris* yeast—The positive colony was cultured under adequate conditions to over-express the recombinant RNase6PL. The yeast protein extract was passed through a Q Sepharose column in a Fast Protein Liquid Chromatography (FPLC) (Amersham Pharmacia Biotech, Buckinghamshire, U.K.). The eluted protein was tested on an SDS-PAGE for the presence of an RNase6PL protein. As is shown in FIG. 54, a 27-kDa protein was obtained from the eluted fraction, consisting of 15 mg of purified RNase6PL protein.

The purified recombinant RNase6PL protein is thermostable at varying temperatures—The thermostability of the recombinant protein was evaluated on an SDS-PAGE following the incubation for 10 minutes of the RNase6PL at increasing to temperatures from 55-100° C. The recombinant RNase6PL was stable at all temperatures tested.

Recombinant human RNase6PL is catalytically active at various temperatures—The catalytic activity of the recombinant RNase6PL was tested in vitro by its ability to degrade RNA. The recombinant protein was capable of degrading RNA following the incubation of the protein (for 10 minutes) at varying temperatures from 55-100° C.

Altogether, these results demonstrate the simple and efficient purification of recombinant RNase6PL protein by denaturation by high temperature and subsequent isolation and purification on a column. In addition, the thermostability and activity at increasing temperature demonstrate that the recombinant protein exhibits the characteristic properties typical to members of the RNase T2 family.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by an accession number mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

What is claimed is:

1. A method of preventing, inhibiting and/or reversing proliferation, colonization, differentiation and/or development of cancer cells in a subject in need thereof, the method comprising administering to the subject a therapeutically effective amount of a ribonuclease of the T2 family wherein the ribonuclease T2 binds actin in either its active or non-active ribonucleolytic form.

2. The method of claim 1, wherein said proliferation, colonization, differentiation and/or development of said cancer cells is a transformation of a benign tumor to a malignant tumor.

3. The method of claim 1, wherein said preventing, inhibiting and/or reversing proliferation, colonization, differentiation and/or development of said cancer cells is preventing or inhibiting metastatic spread of tumor cells.

4. The method of claim 1, wherein said proliferation, colonization, differentiation and/or development of said cancer cells is tumor angiogenesis.

5. The method of claim 1, wherein said ribonuclease of the T2 family comprises a T2 ribonuclease protein having a molecular weight of between 24-36 kDa.

6. The method of claim 1, wherein said ribonuclease of the T2 family is devoid of ribonuclease activity.

7. The method of claim 1, wherein an actin binding activity of said ribonuclease protein is boiling stable.

8. The method of claim 1, wherein administering to the subject said therapeutically effective amount of said ribonuclease of the T2 family is effected by parenteral administration.

9. The method of claim 1, wherein said cancer cells are or are associated with a disease selected from the group consisting of blastoglioma, Kaposi's sarcoma, melanoma, lung cancer, ovarian cancer, prostate cancer, squamous cell carcinoma, astrocytoma, head cancer, neck cancer, bladder cancer, breast cancer, colorectal cancer, thyroid cancer, pancreatic cancer, gastric cancer, hepatocellular carcinoma, leukemia, lymphoma, Hodgkin's disease and Burkitt's disease.

10. The method of claim 1, wherein administering is by an administration mode selected from the group consisting of oral administration, topical administration, transmucosal administration, parenteral administration, rectal administration and by inhalation.

11. The method of claim 1, wherein said ribonuclease of the T2 family is *A. niger* B1 RNase.

12. The method of claim 1, wherein said ribonuclease of the T2 family is selected from the group consisting of RNase T2, RNase Rh, RNase M, RNase Trv, RNase Irp, RNase Le2, RNase Phyb, RNase LE, RNase MC, RNase CL1, RNase Bsp1, RNase RCL2, RNase Dm, RNase Oy and RNase Tp, RNase HI0526, RNase I, Rnase Irp1, RNS2, RNase 3, RNase 1, RNase LX, RNase 6PL.

13. The method of claim 1, wherein said ribonuclease is a T2 ribonuclease from an organism selected from the group consisting of *Aeromonas hydrophila, Haemophilus influenzae, Escherichia coli, Aspergillus oryzae, Aspergillus phoenicis, Rhisopus niveus, Trichoderma viride, Lentinula edodes, Irpex lacteus; Physarum polycephlum, Arabidopsis thaliana, Lycopersicon esculentum, Nicotiana alata, Malus domestica, Pyrus pyrifolia, Momordica charantia, Gallus gallus, Rana catesbeiana, Drosophyla melanogaster, Crassostera gigus, Todarodes pasificus* and *Homo sapiens*.

* * * * *